(12) United States Patent
Odland

(10) Patent No.: US 11,925,808 B2
(45) Date of Patent: Mar. 12, 2024

(54) CHARACTERISATION OF CARDIAC DYSSYNCHRONY AND DYSSYNERGY

(71) Applicant: PACERTOOL AS, Oslo (NO)

(72) Inventor: Hans Henrik Odland, Oslo (NO)

(73) Assignee: PACERTOOL AS, Oslo (NO)

(*) Notice: Subject to any disclaimer, the term of this patent is extended or adjusted under 35 U.S.C. 154(b) by 0 days.

(21) Appl. No.: 18/357,890

(22) Filed: Jul. 24, 2023

(65) Prior Publication Data
US 2023/0405337 A1  Dec. 21, 2023

Related U.S. Application Data

(63) Continuation of application No. 17/514,750, filed on Oct. 29, 2021, which is a continuation-in-part of (Continued)

(30) Foreign Application Priority Data

Apr. 30, 2019 (GB) ..................................... 1906064

(51) Int. Cl.
*A61N 1/368* (2006.01)
*A61B 5/349* (2021.01)
(Continued)

(52) U.S. Cl.
CPC ............ *A61N 1/3682* (2013.01); *A61B 5/349* (2021.01); *A61N 1/0502* (2013.01);
(Continued)

(58) Field of Classification Search
CPC .. A61N 1/3682; A61N 1/0502; A61N 1/3614; A61N 1/3627; A61N 1/36528; A61N 1/36585; A61N 1/36843
See application file for complete search history.

(56) References Cited

U.S. PATENT DOCUMENTS

2006/0293714 A1  12/2006  Salo et al.
2007/0299479 A1  12/2007  Saksena
(Continued)

FOREIGN PATENT DOCUMENTS

| WO | 2010052303 A1 | 5/2010 |
| WO | 2014055692 A2 | 4/2014 |
| WO | 2015073927 A2 | 5/2015 |

OTHER PUBLICATIONS

Search Report dated Oct. 28, 2019, directed to GB Application No. GB1906064.9; 5 pages [Cited in Parent].
(Continued)

*Primary Examiner* — William J Levicky
(74) *Attorney, Agent, or Firm* — Michele V. Frank; Venable LLP

(57) ABSTRACT

A method for identifying reversible cardiac dyssynchrony (RCD) of a patient and treating the RCD measures an event relating to a rapid increase in the rate of pressure increase within the left ventricle. The method calculates a first time delay between the event and a first reference time. If the first time delay is longer than a set fraction of electrical activation of the heart, then the presence of cardiac dyssynchrony in the patient is identified. Pacing is applied to the heart, and a second time delay between the event following pacing and a second reference time following pacing is calculated. If the second time delay is shorter than the first time delay, the method identifies a shortening of a delay to onset of myocardial synergy, OoS, thereby identifying the presence of RCD in the patient. Treatment of the RCD is performed.

22 Claims, 40 Drawing Sheets

Related U.S. Application Data application No. PCT/EP2021/078365, filed on Oct. 13, 2021, and a continuation-in-part of application No. PCT/EP2020/062149, filed on Apr. 30, 2020.

(51) Int. Cl.
  *A61N 1/05* (2006.01)
  *A61N 1/36* (2006.01)
  *A61N 1/362* (2006.01)
  *A61N 1/365* (2006.01)
  *G06T 17/20* (2006.01)

(52) U.S. Cl.
  CPC ......... *A61N 1/3614* (2017.08); *A61N 1/3627* (2013.01); *A61N 1/36528* (2013.01); *A61N 1/36585* (2013.01); *A61N 1/36843* (2017.08); *G06T 17/20* (2013.01); *G06T 2210/41* (2013.01); *G06T 2219/2004* (2013.01)

(56) References Cited

U.S. PATENT DOCUMENTS

| | | |
|---|---|---|
| 2010/0121397 A1 | 5/2010 | Cholette |
| 2012/0109244 A1 | 5/2012 | Anderson et al. |
| 2012/0109247 A1* | 5/2012 | Rajan ................. A61N 1/36842 607/28 |
| 2014/0039333 A1 | 2/2014 | Min |
| 2014/0107507 A1* | 4/2014 | Ghosh ................. A61N 1/3684 607/18 |
| 2015/0142069 A1 | 5/2015 | Sambelashvili |

OTHER PUBLICATIONS

Search Report dated Jan. 18, 2021, directed to GB Application No. GB1906064.9; 5 pages [Cited in Parent].

International Search Report and Written Opinion dated Jul. 30, 2020, directed to International Application No. PCT/EP2020/062149; 13 pages [Cited in Parent].

Examination Report Under Section 18(3) dated Sep. 14, 2020 in Great Britain Application No. GB1906064.9.

Intention to Grand under Section 18(4) dated Jun. 8, 2021 in Great Britain Application No. GB1906064.9.

Notification of Grant dated Jan. 4, 2022 in Great Britain Application No. GB1906064.9.

1 Non-Final Office Action dated Sep. 29, 2023, directed to U.S. Appl. No. 17/514,750; 17 pages.

Examination Report dated Dec. 19, 2023, directed to IN Patent Application No. 202127055436; 7 pages.

Final Rejection dated Jan. 18, 2024, directed to U.S. Appl. No. 17/514,750; 14 pages.

* cited by examiner

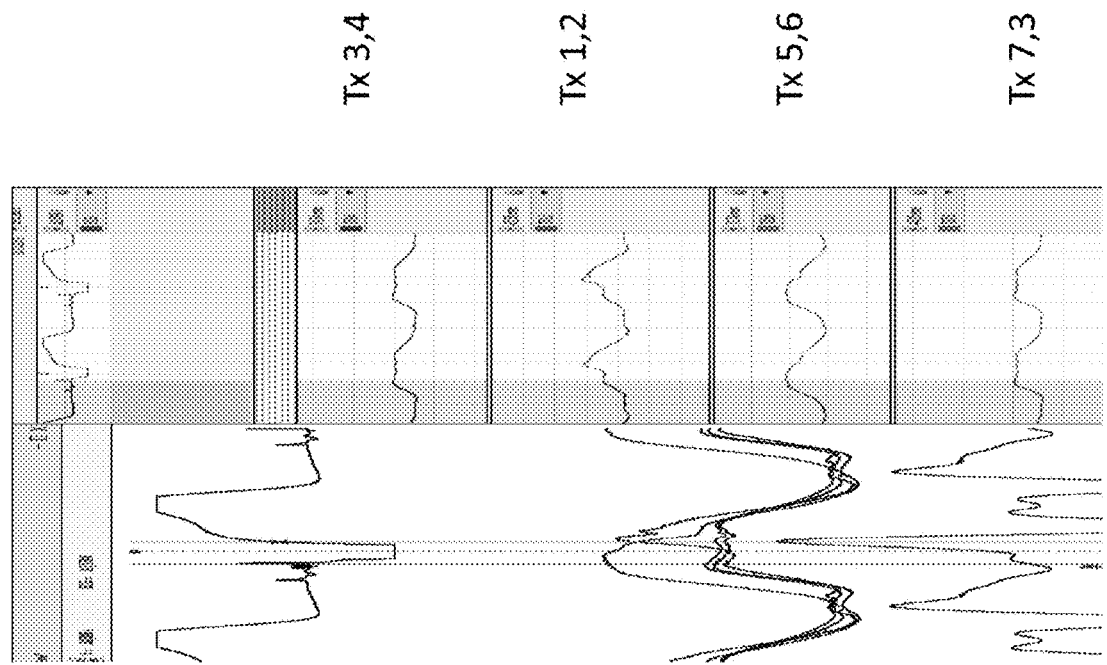
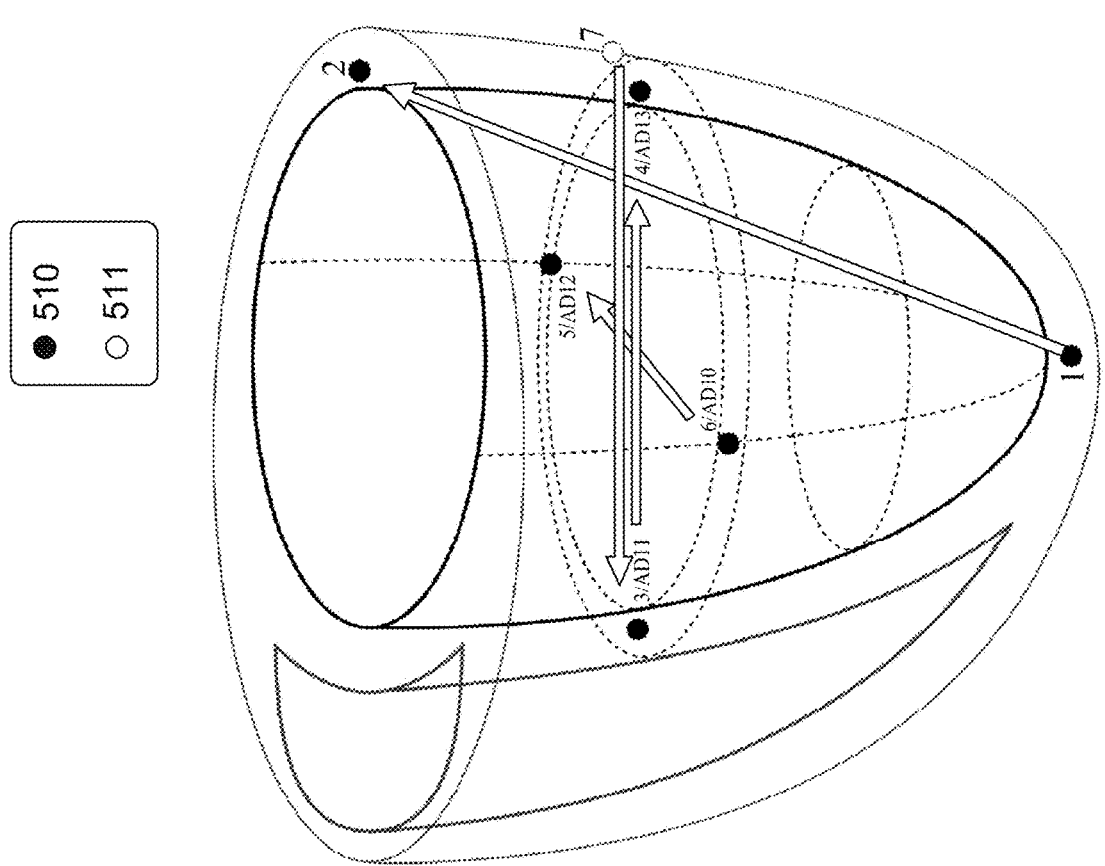
Figure 5b

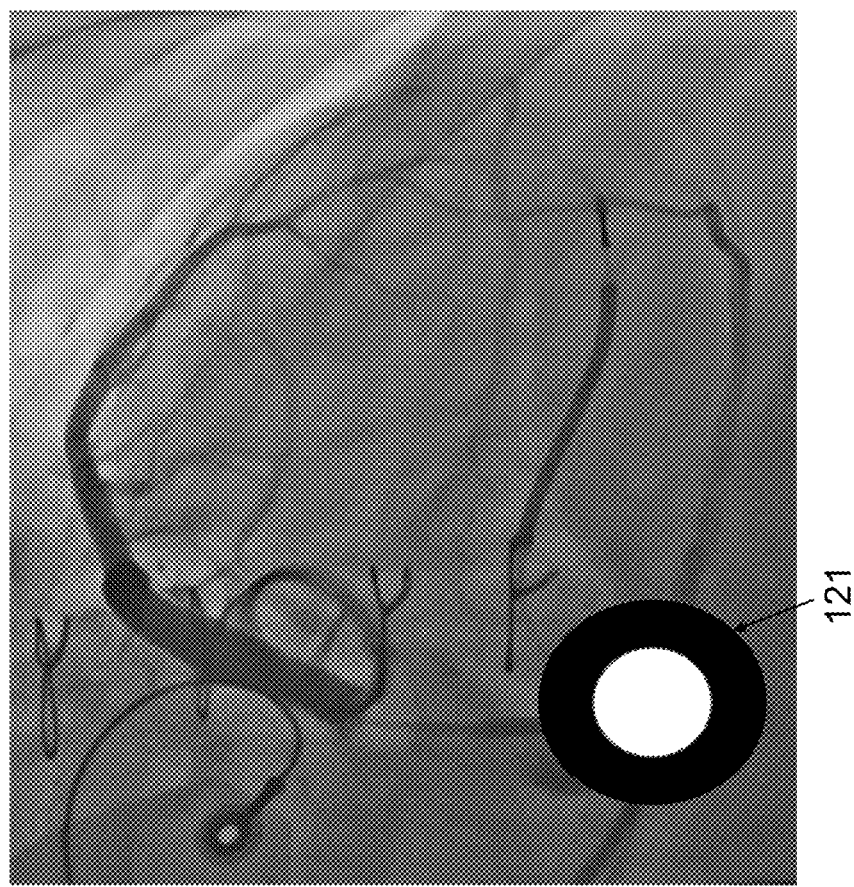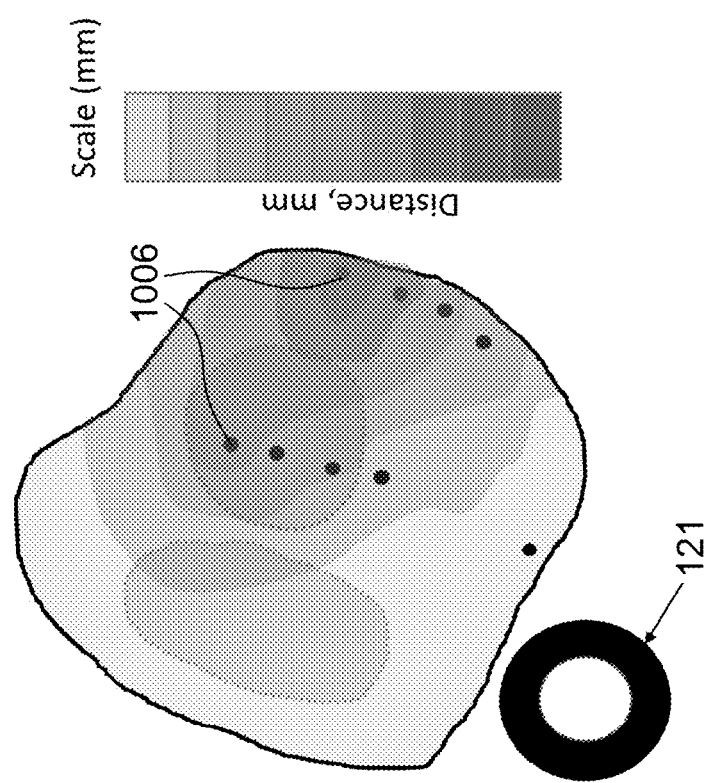
Figure 15

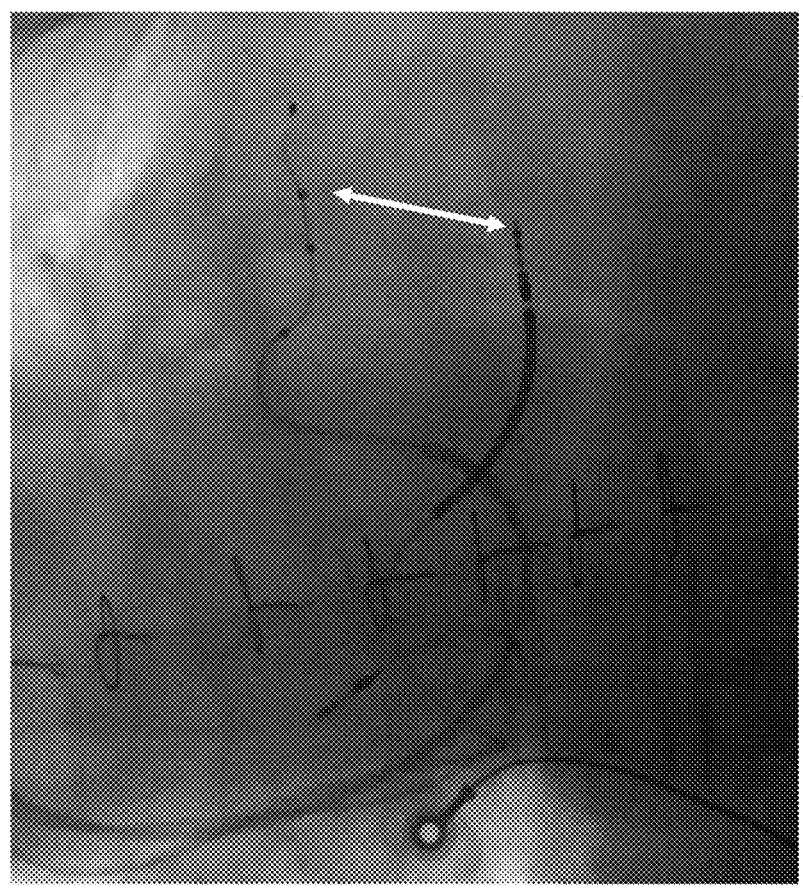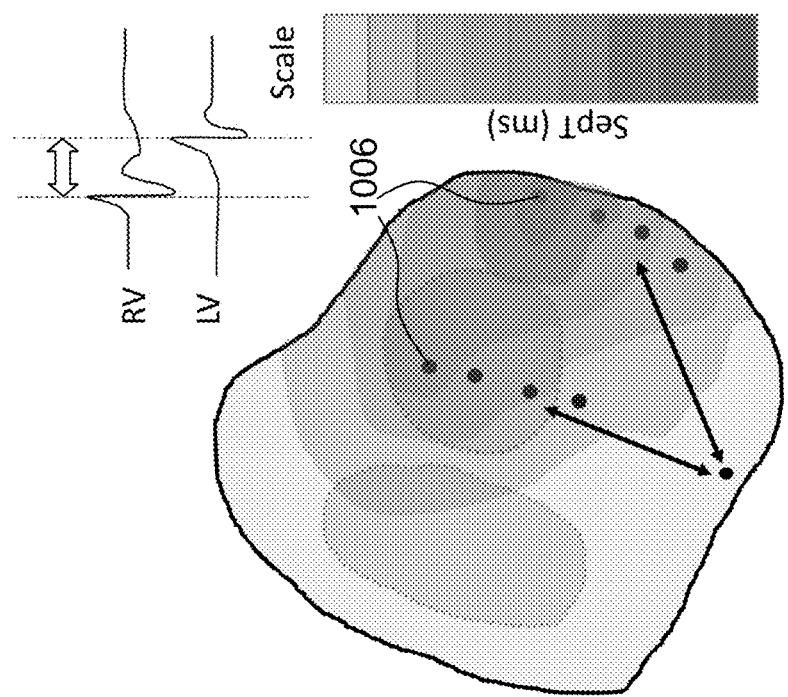
Figure 17

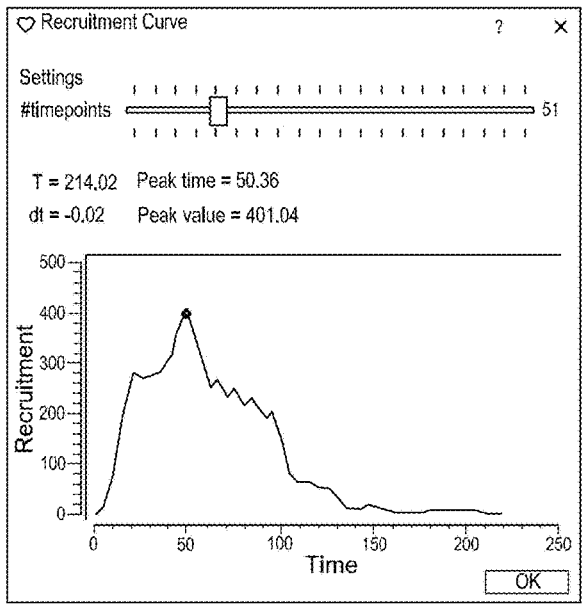
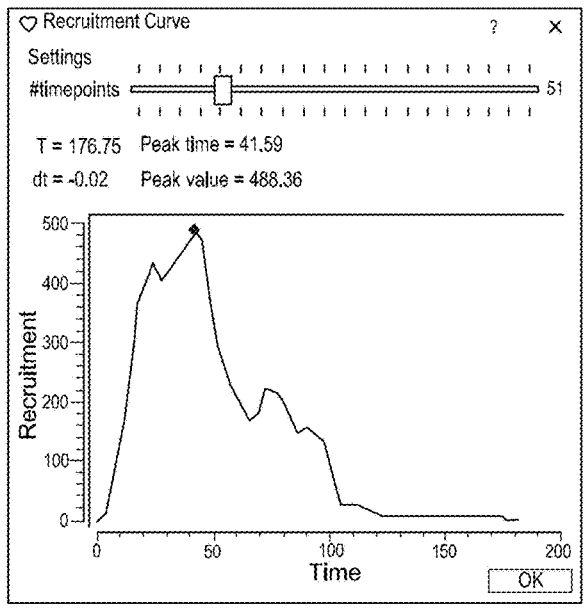
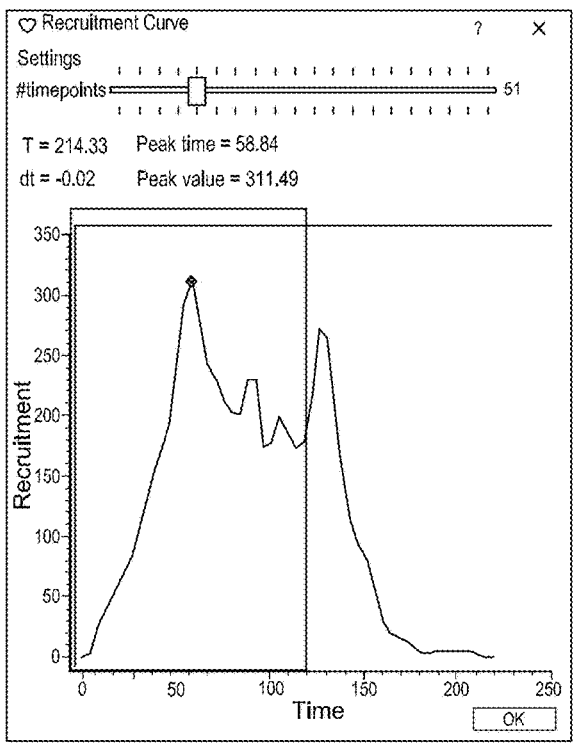
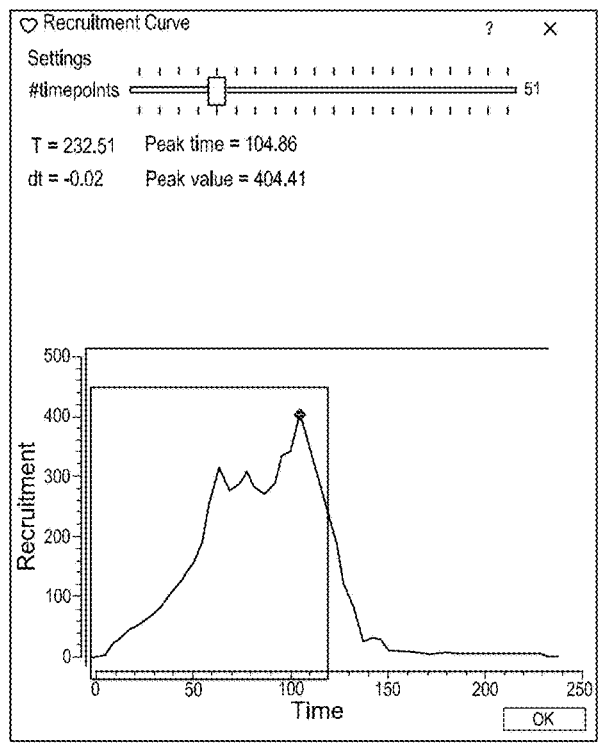
Figure 24 continued

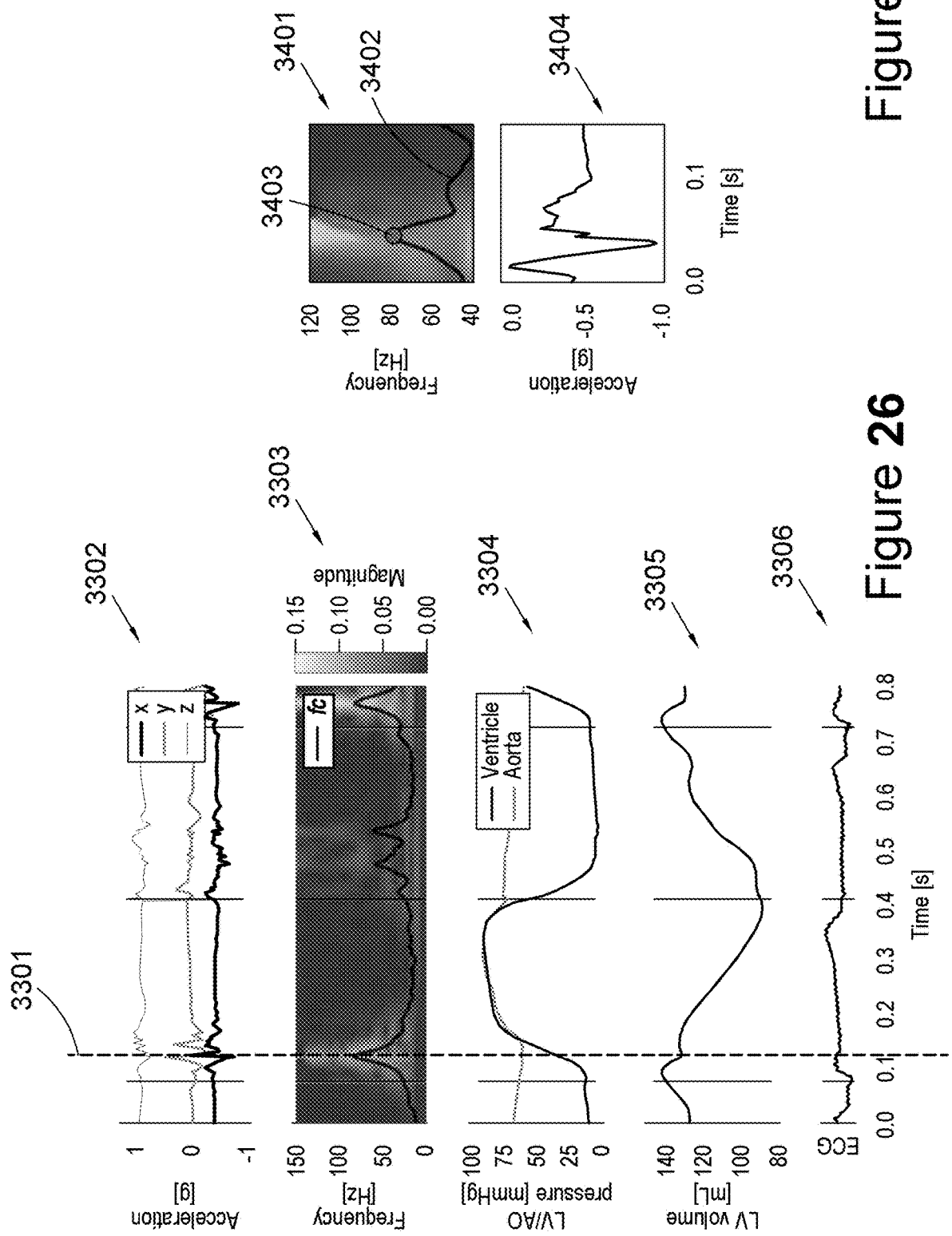

CHARACTERISATION OF CARDIAC DYSSYNCHRONY AND DYSSYNERGY

CROSS-REFERENCE TO RELATED APPLICATIONS

The present application is a continuation of U.S. patent application Ser. No. 17/514,750, filed Oct. 29, 2021, which is a continuation-in-part of International Application Number PCT/EP2020/062149, filed Apr. 30, 2020, which claims priority to GB Application No. 1906064.9, filed Apr. 30, 2019, the entire contents of both of which are hereby incorporated by reference in their entireties. U.S. patent application Ser. No. 17/514,750, is also a continuation-in-part of International Application Number PCT/EP2021/078365, filed Oct. 13, 2021, the entire contents of which is hereby incorporated by reference in its entirety.

TECHNICAL FIELD

The present invention is concerned with a method and system for identifying cardiac dyssynchrony and resulting cardiac dyssynergy of a patient. Thus, the invention may be used in relation to patient's suffering dyssynchronous heart failure, and more specifically can apply to the identification of patients who are likely to respond to resynchronization therapy, as well as optionally determining optimal locations for placement of electrodes to stimulate the heart.

BACKGROUND OF THE INVENTION

Cardiac resynchronization therapy (CRT) is consistently provided according to recognized medical standards and guidelines provided by international medical societies in order to treat patients suffering from various conditions such as a widened QRS complex, (left or right) bundle branch block and heart failure. There are some minor differences between the medical guidelines regarding the specific conditions that should occur before CRT is utilized, such as how wide the QRS complex is, what type of bundle branch block is being suffered and the degree of heart failure.

CRT is associated with a reduction in mortality and morbidity; however, not all patients benefit from such therapy. In fact, some patients may experience deterioration after treatment, some experience devastating complications, and some experience both.

In this regard, it would be beneficial to provide a unifying strategy that reduces the number of non-responders to CRT and optimize the treatment of potential responders, and therefore increases the effectiveness of therapy.

SUMMARY OF THE INVENTION

Broadly, the present disclosure provides, amongst other things, in one aspect, there is provided a method of identifying reversible cardiac dyssynchrony of a patient by:

Calculating a first time delay between a reference time and the rapid increase in the pressure within the left ventricle [the onset of synergy]

Comparing this to the duration of electrical activation in the heart, and if it is longer, then Calculating a second time delay between a reference time and the rapid increase in the pressure within the left ventricle following pacing [the onset of synergy following pacing], then If the second time delay is shorter than the first time delay, then identifying a shortening in the onset of synergy, which indicates that there is presence of reversible cardiac dyssynchrony.

Viewed from a first aspect, the present invention provides a method for identifying reversible cardiac dyssynchrony of a patient by detecting a shortening of a delay to onset of myocardial synergy, using measurements of an event resulting from the onset of myocardial synergy, the method comprising:

calculating a first time delay between the event resulting from the onset of myocardial synergy and a reference time by:
  using data received from one or more sensor(s) to measure the time of an event resulting from onset of myocardial synergy;
  processing signals from the same sensor(s), or one or more other sensor of the one or more sensor(s), to determine the first time delay between the measured time of the event resulting from the onset of myocardial synergy and the reference time;
measuring biopotentials representing electrical activation of the heart;
comparing the first time delay between the measured time of the event resulting from the onset of myocardial synergy and the reference time with the duration of electrical activation of the heart; and
if the first time delay is longer than a set fraction of electrical activation of the heart, then identifying the presence of cardiac dyssynchrony in the patient;
applying pacing to the heart of the patient;
calculating a second time delay between the event resulting from the onset of myocardial synergy following pacing and the reference time following pacing by:
  using the at least one sensor to measure the event resulting from the onset of myocardial synergy following pacing; and
  processing signals from the one or more sensor(s) to determine the second time delay between the determined time of the event resulting from the onset of myocardial synergy and the reference time following pacing;
comparing the first time delay and the second time delay; and
if the second time delay is shorter than the first time delay, then identifying the presence of reversible cardiac dyssynchrony in the patient.

Said another way, the first aspect provides a method for identifying reversible cardiac dyssynchrony of a patient, using measurements of an event relating to a rapid increase in the rate of pressure increase within the left ventricle, the method comprising:

calculating a first time delay between the event relating to the rapid increase in the rate of pressure increase within the left ventricle and a first reference time by:
  using data received from one or more sensor(s) to measure the time when an event relating to the rapid increase in the rate of pressure increase within the left ventricle occurs by identifying a characteristic response in the data received from the one or more sensors, the event relating to the rapid increase in the rate of pressure increase within the left ventricle being identifiable in each contraction of the heart;
  processing signals from the same sensor(s), or one or more other sensor of the one or more sensor(s), to determine the first time delay between the measured time of the identified characteristic response relating to the rapid increase in the rate of pressure increase within the left ventricle and the first reference time;

measuring biopotentials representing electrical activation of the heart;

comparing the first time delay between the measured time of the identified characteristic response relating to the rapid increase in the rate of pressure increase within the left ventricle and the first reference time with the duration of electrical activation of the heart; and if the first time delay is longer than a set fraction of electrical activation of the heart, then identifying the presence of cardiac dyssynchrony in the patient;

applying pacing to the heart of the patient;

calculating a second time delay between the identified characteristic response relating to the rapid increase in the rate of pressure increase within the left ventricle following pacing and a second reference time following pacing by:

using the at least one sensor to measure the timing of the identified characteristic response relating to the rapid increase in the rate of pressure increase within the left ventricle following pacing; and processing signals from the one or more sensor(s) to determine the second time delay between the determined time of the identified characteristic response relating to rapid increase in the rate of pressure increase within the left ventricle and the second reference time following pacing;

comparing the first time delay and the second time delay; wherein if the second time delay is shorter than the first time delay, identifying a shortening of a delay to onset of myocardial synergy, indicating that the time period until the point where all segments of the heart begin to actively or passively stiffen has shortened, thereby identifying the presence of reversible cardiac dyssynchrony in the patient.

As discussed further below, this method allows for an assessment of cardiac dyssynchrony that is not available using existing techniques, and which can enable improved assessment of the patient including in relation to cardiac resynchronisation therapy. By characterising cardiac synchronicity using measurements resulting from the onset of myocardial synergy, for example via measurement of electrical activation or by the measuring of events that reflect mechanical action within the heart, it becomes possible to devise strategies to shorten the onset of synergy, such as by optimising the identification of pacing zones. It should be noted that the method of this aspect is carried out using data from the at least one sensor, and hence the method steps carried out using data outside of the body. The data that is processed outside of the body can include data already obtained from the body for other purposes. This data may be obtained using at least one sensor of any suitable known type, including sensors commonly used for measurements of the heart, both non-invasively and via implanted sensors, with examples including pressure sensors, ECG electrodes, accelerometers and ultrasound sensors as discussed further below. Additionally, the identification of cardiac dyssynchrony may be achieved using data that has already been measured both before, and after pacing, and therefore method considered herein is equally applicable on pre-existing data sets, to determine whether such data is characteristic of cardiac dyssynchrony.

The onset of myocardial synergy relates to the point in time when all segments of the heart either passively or actively stiffen with resulting increase in total force development. This occurs after the earliest electromechanical interval and within the isovolumic phase and before aortic valve opening. This is reflected in several measures, for example by the beginning of an exponential pressure rise within the heart, a rapid increase in the rate of change of pressure in the heart, a beginning of pressure rise above the pressure floor in a filtered pressure signal, the peak of the 2nd order derivative or the onset of pressure rise in the low-pass filtered (below 4 Hz or similar) pressure trace. The peak or onset should be the last peak or onset before aortic valve opening or maximum pressure. Whilst this point in time can be difficult to measure directly, by measuring the time at which an event that occurs as a result of the onset of synergy, it is also possible to obtain an indirect measure of such a time. In reversible cardiac dyssynchrony, a reduction of time to onset of myocardial synergy may be seen with pacing. Therefore, by pacing the heart and measuring the resultant effect on the time of onset of synergy (through an indirect measure), it is possible to identify reversible cardiac dyssynchrony, and therefore identify people who may respond well to CRT treatment.

When discussing an exponential pressure rise, the skilled person would understand the meaning in the context of measure pressure data. In this way, whilst there may be an initial small pressure rise resulting from dyssynchronous contraction (wherein segments of the heart are passively stretched), an exponential pressure rise would, for example, be seen to reflect the last point at which there is an identifiable change in the rate of pressure rise increase before ejection. Such a pressure rise could, for example be measured in the frequency range, as the frequencies contained in the pressure trace increase when there is a step change in the pressure change. This occurs beyond the low order harmonics of the frequency spectrum, and the onset of synergy may become evident when low order harmonics are filtered with a low pass filter or band pass filter. Filtering at, for example 4-removes the low, slow frequencies that are associated with dyssynergy and the onset of synergy may be seen as the onset of the pressure increase that leads to, or is directly prior to aortic valve opening or maximum pressure. This onset of pressure rise is similar to the peak second order derivative of pressure rise in the left ventricle. Both of these measures will reflect onset of synergy.

Similarly a rapid increase in the rate of pressure change would also be well understood in a similar way, as referring to the point at which the rate of pressure change begins to increase at a maximum rate, prior to ejection. This may be reflected in, for example, the final peak in the second order derivative of the pressure of the pressure of the left ventricle prior to aortic valve opening, or maximum pressure.

The first and second reference times may relate to different marker points within the measured data. For example, the first reference time may be taken as the beginning of the QRS curve in an un-paced trace. The second reference time may be taken as the time of the onset of pacing. In this case the step of comparing the first time delay and the second time delay further comprises: compensating for a time delay between the first reference time and the second reference time. This allows for the different measurements to be compared whilst accommodating for any intrinsic differences resulting from the different reference points.

The step of measuring biopotentials representing electrical activation of the heart may further comprise measuring surface biopotentials of the patient to produce an electrocardiogram, ECG, and determining the reference time from the point of onset, offset or the full duration of a QRS signal measured from the ECG. The duration of the QRS complex may then be determined. The step of comparing the first time delay between the measured time of the event resulting from onset of myocardial synergy and the reference time with the duration of electrical activation of the heart may further comprise comparing the first time delay between the measured time of the event resulting from the onset of myocardial synergy and the reference time with the duration of the QRS complex; and if the first time delay is longer than a set fraction of the QRS complex duration, then identifying the presence of dyssynchrony in the patient.

When identifying potentially reversible dyssynchrony in a patient, the method may further comprise modifying the pacing of the heart, and repeating the measurements of an additional time delay to determine whether the time delay may be reduced with a modified pacing regime. Specifically, the method may further comprise applying modified pacing to the heart of the patient, and calculating a third time delay between the event resulting from onset of myocardial synergy following modified pacing and the reference time following modified pacing by using the at least one sensor to measure the event resulting from the onset of myocardial synergy following modified pacing. Signals from the one or more sensor(s) to may then be processed to determine the third time delay between the determined time of the event resulting from onset of myocardial synergy following modified pacing and the reference time following modified pacing. Then, the second time delay and the third time delay may be compared; and if the third time delay is shorter than the second time delay, then reversible cardiac dyssynchrony in the patient may be identified. Any number of alternate pacings (and associated time delays) may be assessed in this way to determine whether the time delay can be shortened, and therefore whether reversible dyssynchrony is present.

The method may include selecting the optimal pacing mode and electrode numbers and positions for cardiac resynchronization therapy or pacing therapy. For example, this may be done by comparing one pacing site to the other, and number of electrodes to other number of electrodes. This may furthermore be suggested by measurements of distance between electrodes, either geodesic or linear distance or electrical time separation or electrical delays to certain zones of the heart, or anatomical positions or any combination of these that would provide a location that should be tested and compared. Again measurements of parallelity, as mentioned below, may be calculated. Anatomical models, either patient-specific or other, may be used for visualization.

The method may comprise measuring surface biopotentials of the patient to produce an electrocardiogram, ECG; and determining the reference time from the point of onset, offset or the full duration of a QRS signal measured from the ECG.

Optionally, the one or more sensor(s) includes an accelerometer or piezo-resistive sensor, and the method may hence comprise: receiving data from the accelerometer or piezo-resistive sensor, which may be within, or connected to the surface of the patient; and determining the reference time from the point of onset, offset, full duration and matched template of the acceleration data or piezo-resistive sensor data.

In some examples, the one or more sensor to measure the time of event resulting from the onset of myocardial synergy includes an accelerometer, and this may be the accelerometer referenced above. The one or more sensor to measure the time of event resulting from the onset of myocardial synergy may include an ultrasound sensor.

The one or more sensor may be configured to detect heart sounds corresponding to the event resulting from the onset of myocardial synergy.

The method may involve injecting current through surface skin electrodes; measuring impedance between electrodes within or close to the heart and its vessels; and producing a complex impedance waveform and an amplitude waveform; wherein the event resulting from the onset of myocardial synergy is the time at which the heart muscle shortens and blood is ejected from the heart, and wherein the time of event resulting from the onset of myocardial synergy is determined where the complex impedance and the amplitude waveform meet and deviate. Thus, the one or more sensors may include surface skin electrodes and electrodes within the body.

The one or more sensor may be a pressure sensor (piezoresistive, fibreoptic and similar) mounted on a catheter located in the left ventricle, and in that case the event resulting from the onset of myocardial synergy may include events detectable by the use of such a pressure catheter, such as the peak pressure rise in the time domain, trajectory advancement, or trajectory delay compared to any trajectory in either the time derivative of a pressure curve trajectory or in the pressure curve trajectory itself.

In some examples, when utilizing an external or internal ultrasound probe to measure cardiac tissue motion, the event resulting from the onset of myocardial synergy includes one of the onset of S-wave velocity, onset of S-wave strain rate, onset of global ejection, aortic valve opening, the onset of aortic flow, myocardial wall velocity, strain or any other measure to measure onset of synergy In order to provide effective pacing, any atrioventricular (AV) delay should preferably be calculated so that the atrioventricular delay (AV-delay) of the pacing is calculated so that Atrial Pace-Ventricular Pace time (AP-VP) is shorter than the shortest of Atrial Pace-Right Ventricular sensing (AP-RVs) and Atrial Pace-QRS complex onset (AP-QRSonset). The AV-delay of the pacing may be calculated as 0.7*(AP-RVs), or if AP-QRSonset is known as or in any other way calculated not to allow any intrinsic conduction to occur through the His-Purkinje system resulting from an atrial stimulus.

The method may include applying modified pacing to the heart of the patient utilizing additional positions of pacing and/or additional electrodes and then further steps to assess the effectiveness of the modified pacing. Such further steps may include calculating an additional time delay between the event resulting from the onset of myocardial synergy following modified pacing and the reference time following pacing by: using the at least one sensor to measure the event resulting from the onset of myocardial synergy following pacing; and processing signals from the at least one sensor to determine the additional time delay between the determined time of the event resulting from the onset of myocardial synergy and the reference time following pacing. The method may then include comparing the additional time delay and the second time delay; and, if the additional time delay is shorter than the second time delay, identifying the presence of less cardiac dyssynchrony with the modified pacing in the patient.

Viewed from a second aspect, the invention provides a system for carrying out the method described above. Thus, the system is for detecting onset of myocardial synergy, as a means of measuring reversible cardiac dyssynchrony of a patient, and the system may comprise;

one or more sensor(s) to measure the time of the event resulting from onset of myocardial synergy;

one or more sensor(s) to measure biopotentials representing electrical activation of the heart;
at least one electrode configured apply pacing to the patient; and
a data processing module configured to:
  use the same sensor(s), or one or more other sensor of the one or more sensor(s), to measure the time of an event resulting from the onset of myocardial synergy by;
    processing signals from the at least one sensor to determine the first time delay between the measured time of the event resulting from the onset of myocardial synergy and the reference time;
    comparing the first time delay between the measured time of the event resulting from the onset of myocardial synergy and the reference time with the duration of electrical activation of the heart;
    if the first time delay is longer than a set fraction of electrical activation of the heart, then identify the presence of cardiac dyssynchrony in the patient;
  apply pacing to the heart of the patient;
  calculate a second time delay between the event resulting from the onset of myocardial synergy following pacing and the reference time following pacing by:
    using the at least one sensor to measure the event resulting from the onset of myocardial synergy following pacing; and
    processing signals from the at least one sensor to determine the second time delay between the determined time of the event resulting from the onset of myocardial synergy and the reference time following pacing;
  compare the first time delay and the second time delay; and
  if the second time delay is shorter than the first time delay, identifying the presence of reversible cardiac dyssynchrony in the patient.

The system may be configured to carry out the method including any or all optional features as above. Thus, the sensor(s) may be as discussed above and the processor may be configured to perform steps as set out above. The system may be provided as a kit including sensors as required along with a processor having the required function. This kit may optionally include the sensors being in place at the patient in order to obtain the required data, or it may be a kit arranged to be used with a patient as required.

The system may comprise a screen for visualization of a heart model with any fiducials and representations of the at least one sensor connected.

Viewed from a third aspect, the invention provides a computer programme product containing instructions that, when executed, will configure a computer system to perform the method of the first aspect and optionally other features as discussed above. The computer system may be the system of the second aspect, and thus may include the one or more sensor as well as the processor, which is configured to perform method steps as set out above.

Thus, the instructions of the computer programme product may configure the computer system to:
  calculate a first time delay between the event resulting from the onset of myocardial synergy and a reference time by:
    using data received from one or more sensor(s) to measure the time of an event resulting from the onset of myocardial synergy;
    processing signals from the same sensor(s), or one or more other sensor of the one or more sensor(s), to determine the first time delay between the measured time of the event resulting from the onset of myocardial synergy and the reference time;
  measure biopotentials representing electrical activation of the heart;
  compare the first time delay between the measured time of the event resulting from the onset of myocardial synergy and the reference time with the duration of electrical activation of the heart; and
  if the first time delay is longer than a set fraction of electrical activation of the heart, then identify the presence of cardiac dyssynchrony in the patient;
  apply pacing to the heart of the patient;
  calculate a second time delay between the event resulting from the onset of myocardial synergy following pacing and the reference time following pacing by:
    using the at least one sensor to measure the event resulting from the onset of myocardial synergy following pacing; and
    processing signals from the one or more sensor(s) to determine the second time delay between the determined time of the event resulting from the onset of myocardial synergy and the reference time following pacing;
  compare the first time delay and the second time delay; and
  if the second time delay is shorter than the first time delay, then identify the presence of reversible cardiac dyssynchrony in the patient.

The above methods, systems and computer programme product may further benefit from combination with the methods, systems, and computer programme product discussed below in connection with determining electrode number and position with reference to the level of parallel activation of the heart. The below aspects are also seen as novel and inventive in their own right.

Viewed from a fourth aspect, the present invention provides a method for determining optimal electrode number and positions for cardiac resynchronization therapy on a heart of a patient, the method comprising;
  generating a 3D mesh of at least part of the heart from a 3D model of at least part of the heart of the patient, or using a generic 3D model of the heart to obtain a 3D mesh of at least a part of the heart, the 3D mesh of at least a part of the heart comprising a plurality of nodes;
  aligning the 3D mesh of at least part of a heart to images of the heart of the patient;
  placing additional nodes onto the 3d mesh corresponding to a location of at least two electrodes on the patient;
  calculating a propagation velocity of the electrical activation between the nodes of the 3D mesh corresponding to the location of the at least two electrodes;
  extrapolating the propagation velocity to all of the nodes of the 3D mesh;
  calculating the degree of parallel activation of the myocardium for each node of the 3D mesh; and
  determining the optimal electrode number and position on the heart of the patient based on the node(s) of the 3D mesh with a calculated degree of parallel activation of the myocardium above a predetermined threshold.

In accordance with this method it becomes possible to identify one or more optimal zones for placement of electrodes by using a model of the patient's heart. This may be done as a part of the method of the first aspect, in order to determine the best placement for electrodes to treat the patient. In effect, this method may find "hotspots" where an electrode is expected to have the most impact, by mapping the regions of the heart with higher degrees of parallel activation. The method may be used to determine an optimal pacemaker configuration. The method may include determining regions with the highest degree of parallel activation, and thus the predetermined threshold may be set based on the highest determined degree of parallel activation. Alternatively, the method may include finding multiple possible regions having a suitably high degree of parallel activation, for example by setting a threshold based on a set minimum number of regions required to be identified, such as four or more proposed nodes. The user can then choose between the regions that are thereby identified. Alternatively, the method may include adding electrodes to the model and calculating the degree of parallel activation for each added electrode to determine added benefits for each electrode based on degree of parallel activation.

Optionally, the step of determining the optimal electrode position on the heart of the patient based on the node of the 3D mesh with the calculated highest degree of parallel activation of the myocardium further comprises determining the node of the 3D mesh with the highest acceleration of propagation from onset to a determined peak of the curve.

The model of the heart may be a model that is already in existence and/or it may be build using data already in existence, such as a 3D model that has been obtained for other purposes aside from the present method. Alternatively, the method may include obtaining the data required to build the 3D model, such as by non-invasive measurements including CT and/or MRI measurements. The method may include providing characteristics to the 3D model of at least a part of the heart of the patient using an MRI scan and/or echocardiography for calculation of geodesic propagation velocity.

The method may comprise generating the 3D model of at least part of the heart of the patient from an echocardiographic and/or a CT and/or a MRI scan of the heart of the patient.

The step of generating a 3D mesh of at least part of the heart from the 3D model may comprise fitting a mesh model to the surface of the 3D model of at least part of the heart of the patient.

Optionally, the step of calculating a geodesic propagation velocity of the electrical activation further comprises utilising a geodesic distance between the additional nodes of the 3D mesh of at least part of the heart of the patient in combination with electrical measures from the at least two electrodes.

The step of extrapolating the geodesic propagation velocity to all of the nodes of the 3D mesh may comprise visualising time propagation of electrical activation throughout the heart at a given time after activation, to calculate the area of the 3D mesh that is activated at said given time utilizing geodesic propagation velocity of the nodes.

The method may include updating the 3D model to reflect determined tissue characteristics for use in simulations.

After a proposed electrode position has been determined, then in order to determine placement for a further electrode, the method may include calculating the node of the 3D mesh with the largest geodesic distance and/or electrical distance and/or a combination of both from the additional node of the 3D mesh corresponding to an electrode.

The step of calculating parallel activation velocity may comprise marking the area of the left ventricle on the 3D mesh of the at least part of the heart that should be part of the calculation, and using tissue characteristic velocity and print out x-axis time and y-axis area when propagating from electrodes.

In some examples, the electrodes are surface electrodes configured to acquire surface biopotentials, and the step of calculating a propagation velocity of the electrical activation between the nodes of the 3D mesh corresponding to the location of the at least two electrodes may comprise: using an inverse solution method to calculate the electrical propagation on the 3D mesh of the heart; and calculating propagation velocity in the model using electrical propagation together with geodesic distance.

The method can include determining the degree of parallel activation of the heart via any suitable measurement or calculation method. One preferred method is set out below. This method is considered to be novel and inventive in its own right, and therefore, viewed from a fifth aspect, the invention provides a method for determining the degree of parallel activation of a heart undergoing pacing, the method comprising:

calculating a vectorcardiogram, VCG, or electrocardiogram, ECG, or cardiac electrograms, EGM, waveforms from right ventricular pacing, RVp, and left ventricular pacing, LVp;

generating a synthetic biventricular pacing, BIVP, waveform pacing by summing the VCG of the RVp and the LVp, or by summing the ECG of the RVp and the LVp;

calculating a corresponding ECG or VCG waveform from real BIVP;

comparing the synthetic BIVP waveform and the real BIVP waveform;

calculating time to fusion by determining the point in time in which the activation from RVp and LVp meets and the synthetic and the real BIVP curves start to deviate;

wherein a delay in time to fusion indicates that a larger amount of tissue is activated before wave fronts for electrical activation meet, thereby indicating a higher degree of parallel activation.

This method may be used by itself as a means to find a measure of "parallelity" of the heart. Alternatively, it may be combined with the method of the first aspect and optionally may be used to validate the optimal position electrode position by determining the degree of parallel activation of the heart.

Viewed from a sixth aspect, the invention provides a system for determining optimal electrode numbers and positions for cardiac resynchronization therapy on a heart of a patient, the system comprising;

a 3D mesh generating module for generating a 3D mesh of at least a part of the heart comprising a plurality of nodes based on a 3D model of at least part of a heart of the patient, wherein the plurality of nodes include additional nodes corresponding to the locations of at least two electrodes on the patient;

an imaging module for providing images of at least part of the heart of the patient;

an aligning module configured to align the images of the at least part of the heart of the patient with the at least part of the heart of the patient;

an electrode data receiving module for receiving data from the least two electrodes on the patient, with these electrodes being represented on the 3D model by the additional nodes; and a data processing module configured to:

calculate a propagation velocity of the electrical activation between the nodes of the 3D mesh;

extrapolate the propagation velocity to all of the nodes of the 3D mesh;

calculate the degree of parallel activation of the myocardium for each node of the 3D mesh; and determine the optimal electrode numbers and position on the heart of the patient based on the node of the 3D mesh with a calculated degree of parallel activation of the myocardium above a predetermined threshold.

The system may be configured to carry out the method of the fourth aspect including any or all optional features as above. In a further system aspect, a system is provided that is configured to carry out the method of the fifth aspect above. Thus, the electrodes may be as discussed above and the data processing module may be configured to perform steps as set out above. The system may be provided as a kit including electrodes as required along with a data processing module having the required function. This kit may optionally include the electrodes being in place at the patient, or it may be a kit arranged to be used with a patient as required.

The at least two electrodes may be surface potential electrodes and/or the at least two electrodes may be situated in the myocardium of the patient.

Viewed from a seventh aspect, the invention provides a computer programme product containing instructions that, when executed, will configure a computer system to perform the method of the fourth aspect and optionally other features as discussed above.

The computer system may be the system of the sixth aspect, and thus may include the electrodes as well as the data processing module, which would be configured to perform method steps as set out above.

Thus, the instructions of the computer programme product may configure the computer system to:
provide a 3D model of at least part of the heart of the patient;
generate a 3D mesh of at least part of the heart from the 3D model, the 3D mesh of at least a part of the heart comprising a plurality of nodes;
align the 3D mesh of at least part of a heart to images of the heart of the patient;
place additional nodes onto the 3D mesh corresponding to a location of at least two electrodes on the patient;
calculate a propagation velocity of the electrical activation between the nodes of the 3D mesh corresponding to the location of the at least two electrodes;
extrapolate the propagation velocity to all of the nodes of the 3D mesh;
calculate the degree of parallel activation of the myocardium for each node of the 3D mesh; and
determine the optimal electrode number and position on the heart of the patient based on the node of the 3D mesh with the calculated highest degree of parallel activation of the myocardium.

In a further computer programme product aspect the invention provides a computer programme product containing instructions that, when executed, will configure a computer system to perform the method of the fifth aspect and optionally other features as discussed above. The computer system may be the system above, and thus may include the electrodes as well as the data processing module, which would be configured to perform method steps as set out above.

Thus, the instructions of the computer programme product may configure the computer system to:
calculate a vectorcardiogram, VCG, or electrocardiogram, ECG, waveforms from right ventricular pacing, RVp, and left ventricular pacing, LVp;
generate a synthetic biventricular pacing, BIVP, waveform pacing by summing the VCG of the RVp and the LVp, or by summing the ECG of the RVp and the LVp;
calculate a corresponding ECG or VCG waveform from real BIVP;
compare the synthetic BIVP waveform and the real BIVP waveform;
calculate time to fusion by determining the point in time in which the activation from RVp and LVp meets and the synthetic and the real BIVP curves start to deviate;
wherein
a delay in time to fusion indicates that a larger amount of tissue is activated before wave fronts for electrical activation meet, thereby indicating a higher degree of parallel activation.

BRIEF DESCRIPTION OF THE DRAWINGS

Certain preferred embodiments will now be described by way of example only and with reference to the accompanying drawings, in which:

FIG. 5b shows the placement of sonomicrometric crystals in the heart for subsequent measurements of myocardial segmental lengths and stiffness;

FIG. 15 shows the use of an object of known size to calibrate the heart model for distance between vertices;

FIG. 17 shows a similar process to FIG. 16 but using separation time based on natural pacing of the heart;

FIG. 26 shows various traces that can be extracted from accelerometer data from an accelerometer sensor positioned within the heart.

FIG. 27 shows in more detail selected traces of FIG. 26.

FIG. 30b shows a more detailed view of the traces of FIG. 30a.

DETAILED DESCRIPTION

Figures 1A, 1B:
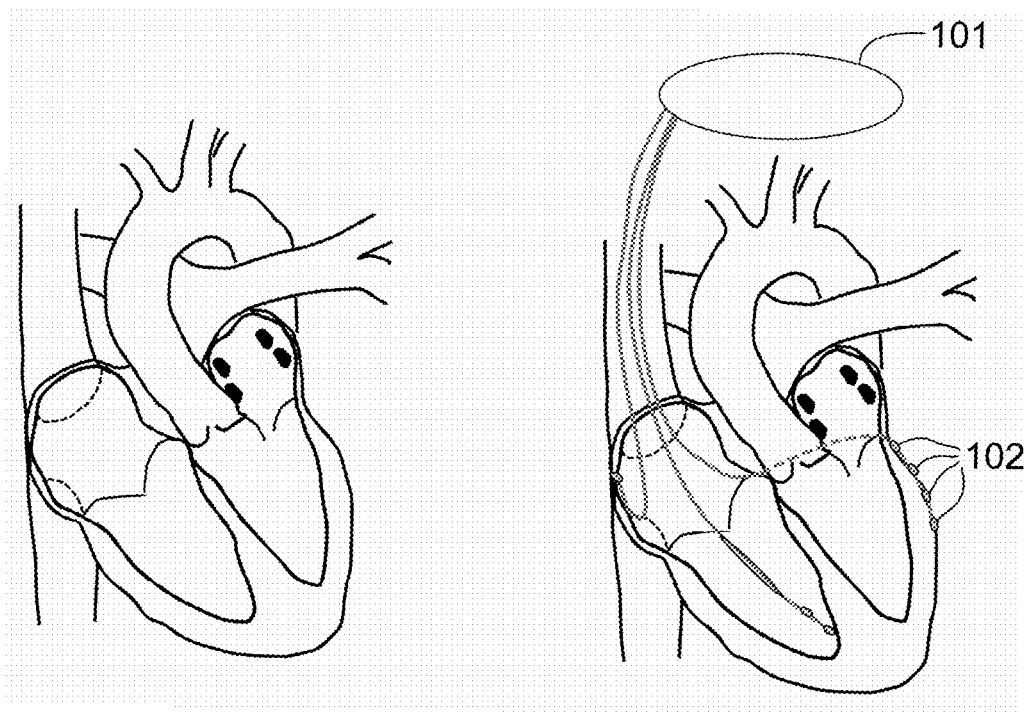
FIG. 1a shows a representation of a normal heart.
FIG. 1b shows a heart undergoing CRT and hence being implanted with atrial and biventricular electrodes.

Generally, a first aspect relates to dyssynchronous heart failure, and more specifically to the identification of patients who are likely to respond to therapy such as cardiac resynchronisation therapy (CRT), and determining optimal locations for placement of electrodes in the heart. CRT aims at reducing heart failure associated with dyssynchrony.

Dyssynchrony is the deviation of activation and/or contraction patterns from that of the normal activation and/or contraction patterns. Normal activation patterns are typically seen in a normal heart with a normal ECG and QRS complex following normal synergic contraction patterns. However, normal activation and contraction patterns may occur in parts of the heart despite presence of dyssynchrony in other parts. Dyssynchrony can typically be described as electrical and mechanical dyssynchrony. However, more specifically and as proposed by the inventors, dyssynchrony can be characterized by the way electrical dyssynchrony is linked to mechanical dyssynergy.

Electrical Dyssynchrony

Dyssynchrony may be classified as electrical dyssynchrony. For example, in such a case, the activation pattern may appear normal in the left chamber when right bundle branch block (RBBB) is present, and similarly the activation pattern may appear normal in the right chamber with left bundle branch block (LBBB). However, normal activation is blocked in the presence of bundle branch block, which forces downstream activation of the heart muscle (myocardium) from cell to cell with a slower propagation than when activated from within the conduction system.

Such a delayed electrical activation results in a delayed contraction of the myocardium at the site of delayed activation. This contraction pattern may be characterized as dyssynchronous in several ways, such as with imaging as MRI or echocardiography, or utilizing ultrasound crystals implanted within the heart walls. Dyssynchronous contractions are typically characterized by regional different timing of electrical activation and contraction.

The extent of dyssynchrony is dependent on the amount of the muscle fibres of the myocardium (sarcomeres) that are activated (contracting) at a time compared to the total amount of sarcomeres. In this regard, preexcitation of a thick heart wall may manifest as a lower degree of dyssynchrony than preexcitation of a thin heart wall, as directional propagation towards the surface of the wall is limited in a thin wall when compared to a thick wall. This results in the excitation of fewer sarcomeres within a certain distance from the origin of activation longer than the distance to the surface of the thin wall (effect of thickness of a wall).

The origin of activation within a transverse of the wall may have a profound effect on the degree of dyssynchrony. Activation of a sarcomere at the centre of a thick region of myocardium will allow for activation in all directions in that segment and thereby results in less dyssynchrony (i.e. less sequential activation in series, rather more synchronous activation in parallel) than activation from the outer border of that thick region (which would result in less parallel activation, but more in series).

Activation of a myocardial wall at its border will similarly result in more activation in series than activation from the centre of that wall (i.e. more activation in parallel), effect of origin of activation within the length of the wall.

QRS Duration

The QRS duration is the sum of the electrical vectors of heart activation. The time duration of the QRS complex reflects the duration of cardiac depolarization. With pacing, the pacing site determines the duration of depolarization as depolarization distributes relative to the pacing site until the myocardium is fully depolarized. RV septum activates the heart bidirectionally, activation towards the right and left once the activation of the septum reaches the free walls of the heart. This is even true with an RV apical position, however, one may note that from the apex activation may become tridirectional; into the septum and the right and left free wall. In this way, with septal activation, activation of the left ventricle starts at a location at the left ventricle and once the RV free wall is reached simultaneous with the activation of the RV. The ventricle that is completely activated last determines the QRS duration. With bidirectional activation QRS is narrower than with unidirectional activation from the free wall, either RV or LV. Septal mid-wall activation that spreads out in all directions in the septum and then bidirectional towards right and left should be reflected in the narrower QRS complex or the shortest duration of activation of the heart when paced. This can furthermore be compared to intrinsic activation to determine whether the exit from the His-Purkinje system is more free wall or more septum and if shorter than with RV septal pacing.

The QRS duration with RV and LV free wall activation should be similar, however dependent on whether pacing is from the base or mid-wall of either site.

When analyzing time to fusion with EGM or VCG, and parallelity, one should make this consideration. The shortest recruitment will occur from the septum and left lateral free wall when unopposed by scar or barriers. Shortest recruitment will occur when pacing from the RV is at the site with the shortest QRS. With pacing the RV from this position QRS has the potential to narrow to the largest extent when the concordant LV position is found. Time to fusion should be as close to 50% of the shortest QRS from RV septum pacing when corrected for Stim to QRS differences between left and right.

Issues with Electrical Measures and Additive Value of Tissue Propagation Velocity Electrical measures are in part hampered by being delayed in scar areas, so that measurements between electrodes and at electrodes might not be representative of the global electrical properties of the cardiac muscle, rather that of the region in which it is measured. A long interval may indicate that there is a conduction block between the two electrodes or in the region of one electrode, but it will not reveal where in the tissue the block is located.

In a typical left bundle branch block, the region of electrical block may be found proximal in the conduction system, while in the presence of scar and non-specific intraventricular conduction delay (IVCD) the block is within the myocardium or in the distal part of the conduction system.

The presence of fibrosis (diffuse disease) may delay conduction in both specific and non-specific conduction tissue. However, without the knowledge of the distance between electrodes, it is not possible to calculate the tissue propagation velocity between electrodes.

The propagation velocity between electrodes, if different, may reveal an area of conduction block between different sites. When geodesic distance is measured between electrodes, then geodesic velocity can be calculated as well to reveal cardiac conduction disease, whether distal or proximal block and/or diffuse disease (such as fibrosis, amyloidosis++).

Mechanical Dyssynergy

Regardless of activation, each sarcomere will contract according to known physiological conditions, which mainly depends on the prestretch of the sarcomere and the load. The action of an isolated sarcomere is termed sarcomeric function, and the action of the heart muscle as whole is termed cardiac function. Whilst measurements of cardiac function have previously been thoroughly studied and described, it has not thus far been useful to determine responders to CRT.

Myocardial function (contractility) has been described in many ways. Typically, contractility has been described with the pressure-volume relationship, represented by the elastance curve or the $E_{max}$. Myocardial functions have also been described with respect to the time intervals of the cardiac phases, either alone or in combination (as a Myocardial Performance Index, or Tei-index). This cardiac function can be quantified by different invasive measures, such as cardiac phase time intervals, $dP/dt_{max}$, as well as pressure-volume relationships with the load-independent elastance curve $E_{max}$. Such cardiac function measures can also be quantified non-invasively with echocardiography or MRI.

The measurement of $dP/dt_{max}$ is used for the measurement of cardiac function to determine the effects of resynchronization therapy (particularly in biventricular pacing).

Resynchronization is the utility of multiple electrodes for stimulation, or additional electrodes when intrinsic conduction is utilized for simultaneous activation. The measure dP/dt max is, however, dependent on load and heart rate and does not change with BIVP compared to LVP only.

In this way, the measure of dP/dt max in itself does not reflect resynchronization but instead reflects changes in cardiac function that depends on multiple factors among contractility, like preload and heart rate (heterometric and homeometric regulation of contractility). Similarly, resynchronization does not change the cardiac function (heterometric and homeometric regulation of contractility), but rather provides synchronization of activation of the myocardium that again may result in changes in stroke volume, afterload and preload that change contractility through heterometric and homeometric regulation mechanisms.

The maximum value of the time-varying elastance E(t) curves, $E_{max}$, does not reflect dyssynchrony. However, the offset in time between the $E(t)_{max}$ with and without dyssynchrony reflects the delayed onset of synergy with dyssynchrony, Therefore, a measure of cardiac function should ideally be a number that is both independent of the loading condition of the heart, and independent of dyssynchrony. Measurements of cardiac function such as the pressure-volume relationship or the force-frequency relationship do not reflect differences in dyssynchrony.

On the other side, a measure of dyssynchrony should not reflect changes in contractility, but rather only changes in dyssynchrony. This is again not the case for the known measures of cardiac function as described above.

Synergy is a term used for sarcomeres that contract in parallel, whilst dyssynergy may be used to describe the situation where the sarcomeres contract in series. Such dyssynergy does not allow the muscle fibre (which consists of sarcomeres contracting in series) to develop work to its ultimate potential, even though each sarcomere may still have the same degree of contractility. In order to measure the contractility of such a muscle fibre it would necessary to know that all sarcomeres of the muscle fibre are actually working in parallel to reach the full potential of contraction so as to be representative of the contractility of each sarcomere within the fibre.

The cardiac conduction system consists of the His-Purkinje network. This network divides in a left and right bundle branch to each cardiac chamber, and both branches split into Purkinje fibres that spread out into a fine endocardial network. One of the main functions of the cardiac conduction system is to activate the cardiac sarcomeres in both chambers close to simultaneously. This leads to activation of sarcomeres in parallel, which in turn allow for synergistic contraction of the cardiac chamber to occur.

For a number of potential reasons, regions of sarcomeres in a heart chamber may not be activated (or be passive). These sarcomeres will be passively subjected to the force that develops in adjacent segments, and therefore subsequently stretched or tightened. Such passive segments are not acting in synergy with contracting segments and are therefore dyssynergistic.

Segments may be dyssynergistic because they are not electrically activated (depolarized), while other segments are contracting after being activated (depolarized), such a situation is termed dyssynchrony, as outlined above. The degree of dyssynchrony depends on the dispersion of electrical activation. With more activation in series (i.e. when there is a greater degree of dyssynchrony), the larger the electrical dispersion. To the contrary, when activation occurs in parallel, the dispersion is low.

However, if the dyssynergy has any other cause than dispersed electrical activation (resulting in activation of the sarcomeres in series), it is not dyssynchrony. Rather, dyssynchrony implies that the electrical timing (chrono) of the activation is out of order (dys), which in turn results in delayed muscle contraction in some regions of the heart, i.e. the sarcomeres are not (dys) cooperating (synergy).

Issues with Mechanical Measures

While electrical measures are readily available for the implanter of electrodes, the mechanical function is not. Standard measures of cardiac function do not work in a dyssynchronous heart to detect dyssynchrony.

In a normal heart with a normal cardiac function, $dP/dt_{max}$ is reduced with RVP and immediately restored with intrinsic heart rhythm. However, when response to an extrastimulus is tested, potentiation is not hampered, indicating that function is not changed. Cardiac function is not changed during a brief period of pacing or even with a single paced beat; however, the measurement of $dP/dt_{max}$ is. When paced at a faster rate $dP/dt_{max}$ increases regardless of pacing the RV or not.

Cardiac phase intervals may also reveal changes in cardiac function, however, this may not be appropriate for measuring cardiac function in a dyssynchronous heart.

Why the Nomenclature of the Cardiac Phases is Incorrect for Use in the Context of Dyssynchrony and Resynchronization Typically, cardiac muscle contraction is divided into two specific conditions under which responses in contraction is different. In a papillary muscle preparation, isotonic contraction indicates shortening of the heart muscle with a certain velocity at a constant load, with the maximum shortening velocity ($V_{max}$) indicating the performance of the muscle. Isometric contraction indicates contraction without shortening at a high load, with force (F) generation being a measure of the performance of the muscle. It is then possible to describe the function as $V_{max}$ and $F_{max}$ in such a papillary muscle.

The phases of heart contraction as described by Wiggers diagram reflects this and divides the cardiac phases into the isovolumic contraction that is supposed to mimic the isometric papillary muscle contraction, and the rapid ejection and systole that is supposed to mimic the isotonic papillary muscle contraction. It is known to a person skilled in the art that with better function (inotropy), shortening of the IVC interval occurs and with poor function, it lengthens. Time intervals can reflect the inotropic state of the heart, also referred to as cardiac function. It is also known that the isovolumic period is not strictly isovolumic as geometric changes occur which shift volume within the cavity during contraction, and mitral valve insufficiency may allow further volume reduction during this period.

With dyssynchrony, onset of contraction occurs at different times within the chamber allowing some regions to contract while other regions will stretch to compensate while still in diastole/relaxation. As this occurs initially at low pressures the potential energy and shortening is wasted and needs to be compensated for by shifting the work load to late contracting segments. The initial phase with dys-coordinated contraction and the resulting remote stretch is a phase dominated by initial dyssynchrony, and then synergy once a balance in force is reached between the muscle fibres before opening of the aortic valve. Once more muscle fibres and regions are recruited and activated, stiffening of the walls occur up to an isovolumic state is reached where muscle fibres will start generate force instead of increasing the velocity of shortening. At this moment of onset of synergy, which is delayed because of slow electrical propagation with dyssynchrony and resulting dyssynergy, pressure starts to increase, and with the onset of synergy pressure rise is exponential up to the opening of the aortic valve.

Onset of synergy is reflected in all of the events that follow exponential pressure rise, and even though the onset cannot be measured directly, the exponential pressure rise indicate that more forces are recruited than absorbed as synergy increases, while the effects of dyssynergy are lost. Opening of the aortic valve allows shortening of fibres, now at a more or less constant force at the capacity of the fibres, until force generation is no longer possible to maintain the pressure as more and more fibres have completed their contraction cycle. However now, even after aortic valve closure, fibres may still contract delaying pressure decay into diastole.

A dyssynchronous heart isovolumic contraction phase (IVC) does not imply isometric contraction of fibres and should be termed differently. This phase is about converting potential energy stored in the muscle fibres effectively into kinetic energy during systole, and this is opposed and delayed by dyssynergy resulting from dyssynchrony. In addition, force and load is regionally different during this phase with dyssynchrony.

The electromechanical coupling interval is furthermore not a distinct interval but is dispersed as activation is delayed, allowing fibres to remain in diastole even after onset of electrical activation of the heart.

During the isovolumic relaxation phase (IVR), relaxation may only occur to a certain degree while some fibres will continue to shorten, so that systole overlaps with IVR and IVR overlaps with onset of diastole. The intervals of the diagram of Wiggers electromechanical coupling, IVC, systole, IVR and diastole is therefore not valid for a dyssynchronous heart cycle.

Resynchronisation

Dyssynchrony, as a disease, is further defined in its nature of reversibility, by restoring parallel activation or reducing electrical dispersion. Such restoration may be achieved by providing pacing at multiple sites. However, dyssynchrony may also be promoted with pacing at multiple or single sites.

It would therefore be beneficial to avoid a situation where dyssynchrony is actually promoted during CRT by determining how the reversible disease of dyssynchrony may be detected and evaluated, so as to characterize whether the intervention (for example, CRT) causes more or less dyssynchrony (an increase or decrease in parallelity, as described below) and/or more or less dyssynergy (late onset of synergy).

Activation of the heart results in depolarization of the cardiomyocytes of the myocardium, so that contraction occurs at the activated site. Parallelity is a term introduced to describe the degree of parallel activation of the myocardium.

Whereas synergy describes sarcomeres cooperating and contracting, dyssynergy describes sarcomeres not cooperating. As previously described, the activation of sarcomeres in series leads to a contraction of the sarcomeres in series, as seen with dyssynergy, whilst the simultaneous activation of sarcomeres in parallel leads to cooperation of sarcomeres as seen in synergy. Dyssynergy is characterized by contractions that occurs at different points in time, either sequential (meaning that neighboring tissue start contracting one after the other in a specific pattern, until contraction occurs over the full myocardium), or non-sequential meaning that different parts of the myocardium contracts in parallel following subsequent activation of neighbouring tissue in a certain pattern (thereby again ending up with covering the full myocardium).

In this way, it may be said that dyssynergy describes the mechanical action and a lesser degree of parallelity (which considers the parallel activated segments compared to the activation of sarcomeres in series) of the sarcomeres. While electrical activation in terms of recruitment describes electrical action. With resynchronization both of these results are linked so that restoration of electrical action and higher recruitment leads to restoration of mechanical action and more synergy (parallel activation).

In a normal, healthy heartbeat, electrical activation occurs during a short period in time, which is represented by a narrow QRS complex. Activation occurs on a microscale in series and non-sequentially at multiple sites within the heart, promoted by the Purkinje system. This results in a rapid onset of contraction at multiple sites in parallel (with synergy) within the chamber within a short time-frame.

Once the tension (caused by the contraction of the sarcomeres) is in balance between all the activated segments of the heart (multiple regions), dominantly parallel contraction is rapidly established. This onset of myocardial synergy promotes an exponential pressure rise within the ventricle preceding aortic valve opening and ejection, and any cardiac event that follows.

As activation occurs outside the specialized conduction system, the activation process is even more delayed and dyssynchronous compared to a normal heartbeat. In a dyssynchronous heartbeat, the electrical activation occurs at a slower rate in series, and occurs sequentially, which leads to dyssynergic contraction in series. When contraction occurs in series, the contracting segments shorten, and in turn passively stretch the not yet activated segments. As such contraction occurs, the potential energy resulting from contraction of the segments is wasted at a low intraventricular pressure, and only serves to stretch not yet activated segments. This process continues until the tension between the stretched (but not yet activated segments) and contracting (activated) segments are in balance. This balance is promoted by activation of already stretched segments. With such a balance of tension, the shortening contraction of the sarcomeres is hampered and the sarcomere contractions change from an isotonic contraction (i.e. contraction generating shortening velocity at a constant tension) to isometric contraction (i.e. contractions generating force without changing the length of the muscle), which results in more sarcomeres contracting in synergy and hence this defines the onset of myocardial synergy. Such an onset of myocardial synergy in turn allows the sarcomere contraction force to convert into exponential pressure increase. This delayed exponential pressure increase precedes aortic valve opening and ejection, and any cardiac event that follows.

As previously mentioned, it is desirable that a measure of dyssynchrony should reflect dyssynchrony only, and not of any other measurements such as cardiac function.

Pacing of a ventricle directly in the myocardium can introduce dyssynchrony because activation then no longer follows the conduction system and therefore does not lead to a normal contraction pattern. Potentially any kind of pacing that occurs outside of the conduction system may introduce dyssynchrony which in turn can result in dyssynergy to a large extent. It is important to be able to measure these effects once pacing is initiated in a patient. Pacing can be viewed upon as a model of both dyssynchrony and dyssynergy.

Dyssynergy resulting from dyssynchrony delays the pressure rise in the ventricle, thereby resulting in a delayed onset of myocardial synergy, and hence ejection, and the following systolic shortening and any event that follows. However, a delay in onset of synergy may also occur with diminished heart function, mitral valve insufficiency and cardiac fibrosis and scar without dyssynchrony, but to a different extent than when caused by dyssynchrony. Even if a mix of dyssynchrony and other causes of delayed onset of synergy exist, shortening of onset of synergy can only occur as a result of resynchronization (but only to a limited extent depending on the ratio of the mix of causes).

Whilst dyssynchrony may be corrected with resynchronization, the other cardiac diseases may not. With resynchronization, the inventors have showed that shortening of the time to onset of maximal pressure rise (or myocardial synergy) results. In this regard, any measurement that reflects the time interval to onset of myocardial synergy will shorten with resynchronization, and the measurement of such a time interval will always be relative to the QRS or any associated feature.

In potentially reversible dyssynchrony, the onset of synergy is seen at the end of or after the QRS complex. The delayed onset of synergy resembles the widening of the QRS complex, which therefore indicates the presence of dyssynchrony. However, in a widened QRS complex with a near to normal time to onset of synergy, dyssynchrony is not present, and the delay is rather caused by factors other than potentially reversible dyssynchrony. By detecting the presence of reversible dyssynchrony, it may be determined whether a patient is likely (will) to respond to CRT, while with absence of a delay to onset of synergy the patient will likely not respond to CRT or may experience unwanted effects of CRT.

The positioning of electrodes and number of electrodes used for CRT stimulation should aim at shortening the delayed onset of synergy to the largest extent. By defining a relationship between synchronicity, parallelity and the onset of myocardial synergy, and utilizing the lateness of maximum pressure increase (or any other sensor detected delay in this interval) during an intrinsic or paced rhythm, it is possible to predict a site for (left and right) ventricle electrode placements that results in a favourable response to CRT.

When a widened QRS is present, the resulting mechanical dyssynergy needs to be defined before resynchronization can occur, then considering optimal parallelity of electrical activation to achieve electrical resynchronization. Validation needs to occur again on the mechanical side to confirm that the time to onset of synergy has been shortened, evidencing resynchronization effects. In this way, mechanical and electrical events of the heart need to be considered in order to both identify for whom treatment may be beneficial, and to optimize treatment in patients with dyssynchrony.

When the cause of dyssynergy is dyssynchrony, the wasted work, shifted load and dyssynergy can be reversed with resynchronization. When the cause of dyssynergy is not dyssynchrony, this cannot be reversed with resynchronization. Therefore, it would be beneficial to identify when such dyssynergy is indeed caused by dyssynchrony in order to indicate whether a patient is likely to respond to CRT.

By determining how the reversible disease of dyssynchrony may be detected and evaluated, it is possible to characterize whether an intervention (for example, CRT) causes more or less dyssynchrony (an increase or decrease in parallelity, as described below) and/or more or less dyssynergy (lateness in onset of synergy).

Therefore, by identifying the presence of the underlying substrate of dyssynchrony as a disease, it is possible to ensure that CRT is only applied to patients that are most likely to respond to such treatment, and avoid providing CRT to patients where the cause of dyssynergy is not electrical dyssynchrony, which may only serve to promote such a defect (dyssynergy).

However, as outlined above, resynchronization cannot be measured in the cardiac function domain. Rather, it has been determined by the inventors that dyssynchrony relates to the lack of parallel contraction of myocardial tissue, which is not reflected in traditional measures of cardiac function as such. Equally, resynchronization does not serve to increase cardiac function, but rather to result in synchronization of activation of the myocardium and then to allow the myocardial sarcomeres to work near its optimum in synergy to reflect cardiac function without dyssynchrony.

With more dyssynchrony the myocardium changes the pattern of contraction from contraction in parallel to contraction more in series. Dyssynchrony also increases when the intrinsic pattern of electrical activation of the heart changes. This can be seen with pacing or with bundle branch block in specialized conductive tissue (bundle branches).

The time duration of the QRS complex, i.e. the QRS width in milliseconds, corresponds to how rapidly the activation of the ventricle occurs. The cause of any delay may be due to conduction properties in the myocardium, either due to conduction block (dyssynchrony) or with lower electrical propagation velocity (myocardial disease), or a combination of both. By determining how dyssynchrony relates to the electrical activation of the heart, and how it subsequently leads to a delay of when the cardiac muscle contraction leads to ejection of blood from the left ventricle, it is possible to determine whether such function can be restored with CRT, and thereby whether a patient is likely to respond to such therapy.

In the measurements described herein, bioimpedance measures the point in which muscle contraction (phase) leads to ejection (impedance). Complex impedance is more likely to reflect muscle contraction under given circumstances, and absolute impedance to a larger extent under given circumstances reflect volume changes within the cardiac chambers. While electrodes are submersed in blood, they provide the blood pool with electrode properties, and similarly, when electrodes are positioned within the right ventricle, they give the blood pool of the right ventricle such electrode characteristics. The right ventricular blood volumes can therefore serve as an extended electrode area towards electrodes positioned on the left side of the heart. In this way, when a current is injected between surface electrodes of the body, changes in the impedance field between the right and the left electrodes will reflect volume changes and muscle density between the electrodes. With onset of synergy, the volume of blood starts depleting with ejection of stroke volume and the muscle density increases with thickening of the myocardium. When the curves of impedance are plotted against time and the complex impedance increases with increasing muscle density while the absolute impedance decreases with volume depletion. Therefore, it may be said that the moment in time when the curves deviate from each other reflects onset of synergy, and is delayed with delayed onset of synergy.

As discussed above, dyssynchrony can be corrected by modifying the activation of the tissue from being in series to being more in parallel. This can be achieved by stimulating conductive tissue such as the heart muscle or the specialized conduction tissue selectively at certain sites.

When one heart chamber contracts, the isovolumic pressure increases up to $P_{max}$, whilst when contraction occurs with a change in volume, the pressure remains constant whilst the contraction velocity increases depending on the pressure and developed force. With synergy, the sarcomeres contract and energy is rapidly transferred into kinetic energy ejecting blood volume into circulation. This onset of contraction allows for the volume of blood to remain in position within the ventricle in an isovolumic state, and as a result, pressure increases exponentially up to $P_{max}$ with no wasted work.

However, when contraction occurs in series as found in dyssynergy, the volume of blood in the chamber is shifted as the myocardium is stretched whilst other parts are shortening, which generates shortening velocity rather than pressure increase. This occurs until the tension within the chamber wall is balanced, which allows for delayed isovolumic conditions, synergic contraction and energy transfer with an exponential pressure increase up to delayed ejection.

Exponential pressure rise within the ventricle is hence linked to the onset of synergy, OoS, and the time may be well defined by the peak pressure rise of the exponential pressure curve, peak dP/dt. It may be said that onset of myocardial synergy occurs close to peak dP/dt, and therefore the peak dP/dt can be used to detect the time of said onset of myocardial synergy.

By providing a consistent method of detection of a defined event, the bias from the defined event to the onset of myocardial synergy is constant. In this way, the relative timing differences between the detected event and the true event of onset of myocardial synergy are similar, regardless of the offset between the measured event and the true event.

For example, the time to peak dP/dt may be readily measured invasively with a pressure catheter in the left heart chamber, which in turn will occur at a fixed timing delay to the onset of myocardial synergy. Similarly, any event related to the time to peak dP/dt, such as aortic valve opening and closure, onset of ejection, flow in aorta, a negative peak of dP/dt, can be utilized as a surrogate, which when compared to a like measurement, will occur at a same bias towards the true event (of the onset of myocardial synergy). Therefore, such measurement may be used to provide data indicative of the time of onset of myocardial synergy.

With dyssynergy and/or dyssynchrony, a delay in pressure increase results. During this delay, potential energy stored in the sarcomeres is wasted in the sarcomeres that contract at low pressures. The load is shifted towards late contracting sarcomeres where potential energy is converted into first pressure, and then kinetic energy once the aortic valve opens. In such a case, dP/dt peaks later relative to the QRS complex duration and thereby every event relative to this is delayed, such as the aortic valve opening and closure. By measuring the time to peak dP/dt relative to the QRS complex duration, in effect calculating a measure of peak dP/dt/QRS, it is possible determine whether dyssynchrony is present or not, and thereby whether the patient is likely to be a responder or a non-responder. A relatively long interval, for example a time to peak dP/dt of greater than 100% of the QRS complex duration indicates that dyssynchrony is present and is the cause of dyssynergy, while with a short Time to peak dP/dt, for example less than 85% of the QRS complex duration, indicates that dyssynergy does not result from delayed electrical activation (long QRS duration).

Shortening of this time interval with resynchronization therapy will shorten this interval when parallelity is increased compared to baseline (the parallel/serial ratio increases). A short interval, less than 85% of the QRS, indicates that dyssynchrony is not present and resynchronization therapy may be of limited value unless Time to peak dP/dt is shortened to a larger extent with resynchronization therapy.

To the contrary, a short delay to onset of myocardial synergy indicates that no (or less) dyssynchrony is present, and rather that the increase in QRS duration does not translate into dyssynergy. A short QRS duration and a relatively delayed onset of myocardial synergy may be caused by dyssynergy related to myocardial disease and not to electrical dyssynchrony. Resynchronization will not change this, when dyssynergy is not caused by electrical dyssynchrony, and when pacing is needed, pacing the specialized conduction tissue will not change time to peak dP/dt (for example, the use of a known selective His bundle pacing) and should be the treatment of choice to avoid introduction of dyssynchrony and resulting dyssynergy. However, if one would want to apply pacing from multiple points, one should choose pacing sites that result in the shortest time to onset of synergy.

When various ways to measure the time to onset of synergy have been identified, and the time reference is known, any time measure that reflects onset of synergy with a constant bias can be used for comparison with the same measurement under different conditions, but with the same time reference, because the bias may be omitted as it will be constant between the compared measurements. Such a measurement, once the underlying theory as outlined herein is understood, can be used for the determination of presence of dyssynchrony, or to determine the effect of resynchronization. Examples of sensors that will provide these measurements are given in the following.

Therefore, by determining the point of onset of myocardial synergy using obtainable measurements relating thereto, the synchronicity of activation of the myocardium may be measured. The results of resynchronization therapy on myocardial synergy may then be measured by employing direct electrical and mechanical measures using different electrodes and sensors.

For example, various electrical measures can be monitored using electrodes in direct contact with the surface of the body, the heart or anywhere therebetween to inject current or measure biopotentials/characteristics, or complex impedances. Equally, various measures of mechanical events may be accomplished using a variety of sensors, like pressure sensors, accelerometer, phonocardiogram, ultrasound, magnetic sensors or indirect measures of cardiac motion. The connection to sensors and electrodes allow visualization of signals from the patient and measurements time intervals.

Signals from these electrodes or sensors can be processed and compared to determine the degree of synergy or dyssynergy. Based on these measures, a patient can be labelled as a non-responder or a responder (i.e. whether the patient would benefit from CRT), and the degree of response or non-response to CRT can be measured.

Specifically, a system, device, and a method for detecting onset of myocardial synergy as a means of measuring cardiac dyssynchrony are provided. An optimal pacing mode may then be selected, for example biventricular pacing (BIVP), His Bundle pacing (His) and/or any other pacing. Optimal electrode positions may also be chosen, (whether in the LV coronary vein, His, endocardial or any) for CRT or pacing therapy.

Resynchronization Potential

When the intrinsic time to onset of synergy is as long as the electrical delay (QRS duration) a resynchronization potential is said to be present. This is confirmed when the intrinsic time to onset of synergy is shortened with pacing from multiple sites; a resynchronization potential is said to manifest. The resynchronization potential defines the presence of dyssynchrony, as time to onset of synergy is at it shortest with intrinsic conduction (i.e. no electrical delay), no further shortening in time to onset of synergy can be achieved with pacing, and said no resynchronization potential is present.

Assessment of Cardiac Dyssynchrony

A representation of a normal heart may be seen in FIG. 1a. Typically, a heart undergoing CRT may be implanted with atrial and biventricular electrodes 102 as in FIG. 1b, which are connected to a programmable pacemaker 101.

Figure 2:
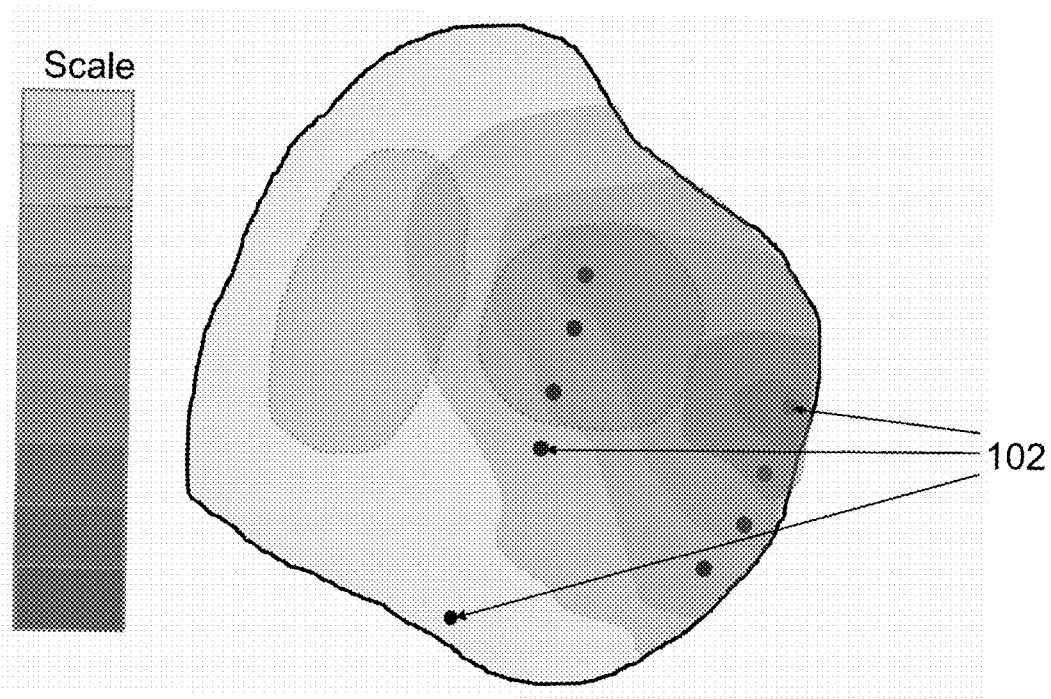
FIG. 2 illustrates a 3D surface geometry model of the heart with representations of locations of the electrodes of FIG. 1b.

The locations of said electrodes 102 may be represented on a 3D surface geometry model of the heart, thereby showing a heart model display with colour maps representing measurement zones relative to the electrodes as seen in FIG. 2. A contour map may then be projected onto the surface of the heart model in order to visualize lines of constant magnitude of a measured value at each area of the heart, and the location of the electrodes within the color zones. Each color represents a measurement, and different degrees of colors represent different degrees of that measure as seen in the scale. For example, measurements pertaining to the intracardiac impedance measured between a pair of electrodes may be visualized on such a model in this way.

Firstly, the system may comprise a bioimpedance measurement system is provided to connect to pacing wires that are situated within any chambers and/or vessels of the heart and surface electrodes for current injection. Measurements of complex impedance, phase and amplitude will allow characterization of the time of onset of myocardial synergy.

Figure 3:
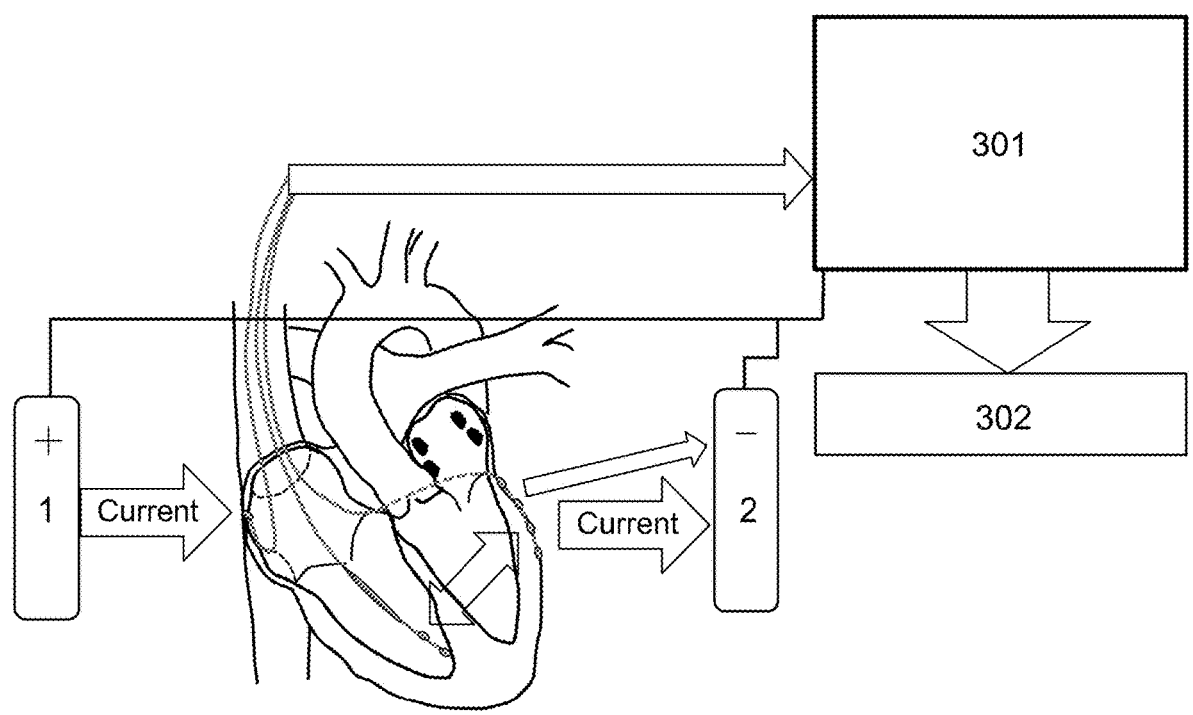
FIG. 3 is an example system for measuring bioimpedance on the heart.

An example system for measuring bioimpedance may be seen in FIG. 3. Therein is shown a measurement setup for impedance (dielectric) measurements on the heart, with implanted CRT electrodes as shown in FIG. 1b. Current may be injected through surface skin electrodes 1 and 2, and impedance may be measured between the electrodes, or between electrodes and patches. Multiple electrodes can be included in measurements of complex impedance. Impedance may then be processed in a processing unit 301, and converted into digital signals that can further be transferred to any digital signal processing unit 302 for display of complex impedance waveforms. The calculated impedance waveforms may further be utilized for calculation of onset of synergy or be compared to known waveforms for similarity or deviation therefrom. Multiple frequencies of injected current may be adjusted to optimize the amplitude phase relationship and directional change for optimization of the impedance phase trajectory interaction.

The electrodes may be placed on the surface of the body, for example perpendicular to the axis of the heart (from center of mitral valve orifice to the LV apex) for current injection. Current injection may also be performed from electrodes located within the heart.

The system may further include one or more sensors to provide measures of onset of synergy as described above. For example, an accelerometer or a piezo-resistive sensor or a fibreoptic sensor may also be provided either on the body surface, or embodied within a catheter in the heart (such as an ablation catheter for detection of the His potential) to detect the heart sounds, aortic valve opening or closure. An ultrasound sensor may be used to provide similar measurements. A pressure transducer may be positioned on a catheter within the right or left ventricle, so as to detect peak pressure rise in the time domain, and/or to detect trajectory advancement. The transducer may also measure any delay compared to any trajectory in either the time derivative of the pressure curve trajectory or in the pressure curve trajectory itself. Additionally, and/or alternatively, surface electrodes for producing an ECG may also be provided.

The data provided by the sensors may then be processed and used to calculate a degree of offset between the onset of pacing and the onset of myocardial synergy as a measure of cardiac dyssynchrony.

For example, a circuit implemented in hardware and/or software is used to receive signals from one or more of the above described sensors and/or measurements, corresponding to the time when the cardiac activation and contraction leads to ejection.

The circuit may then additionally receive the ECG signal of the heart, which corresponds to time point when the heart starts depolarizing, as well as when it is fully depolarized. The ECG can be used as a time reference, and the resulting signals can be related to the onset/offset of intrinsic activation of the heart, and/or onset of pacing as seen in the surface ECG. Such information may be utilized as a reference to provide a time interval relative to onset of pacing and/or onset/offset of the ECG.

Figure 4A:
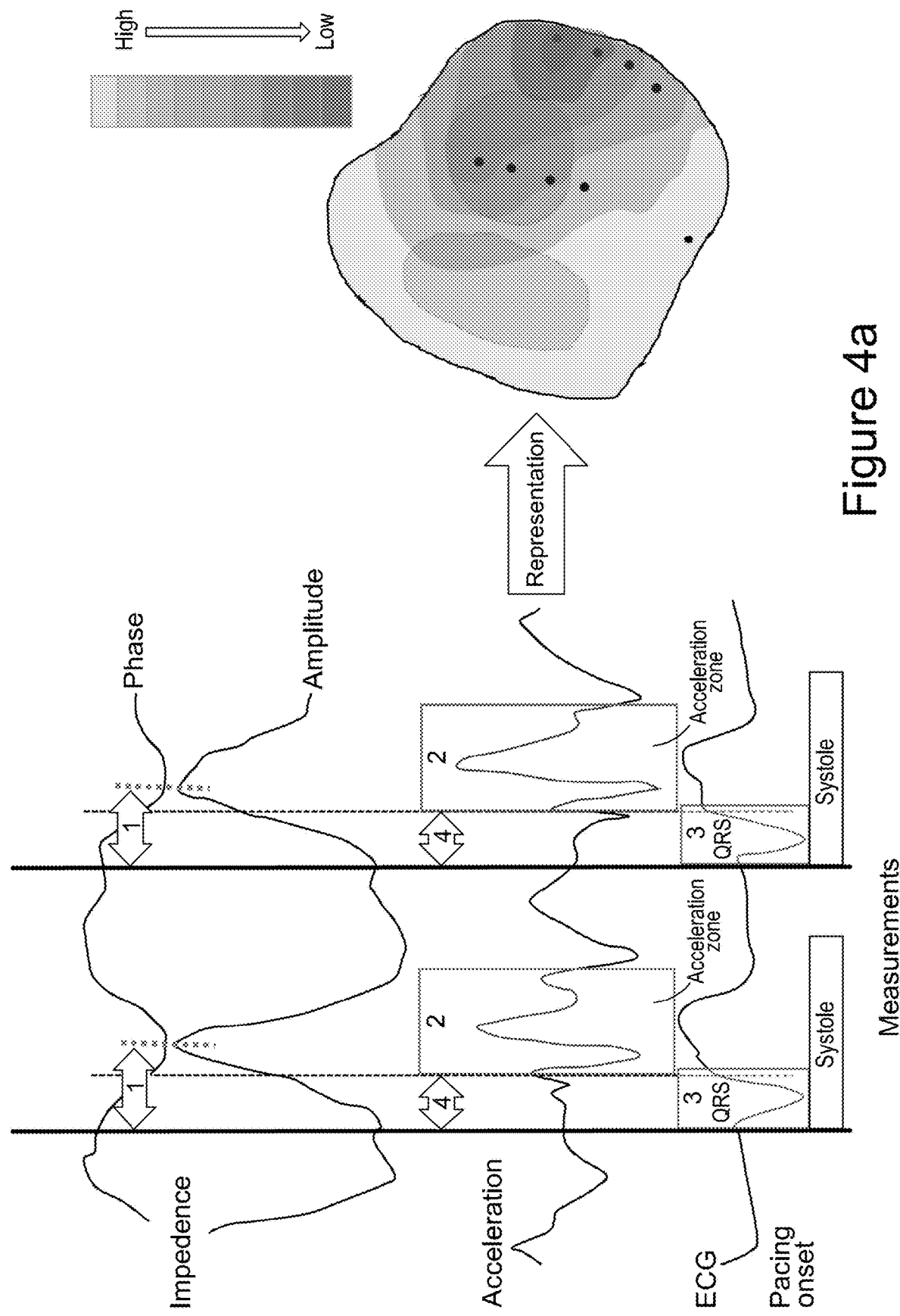
FIG. 4a shows measurements of any representation of onset of synergy along with impedance and/or acceleration.

Such a utilization of measurements as a way of measuring the delay to onset of myocardial synergy may be seen in FIG. 4a. FIG. 4a shows measurements of any representation of onset of synergy, measured with impedance and/or acceleration or piezo-resistive sensor signals.

The measured impedance is represented with complex impedance (phase), corresponding to the contraction of the heart muscle, and the amplitude, corresponding to the blood volume within the heart. In this way, the amplitude of the impedance signal may be used as a surrogate for volume changes within the left heart chamber, as changes in the amplitude signal is paralleled by changes in ventricular blood volume. The phase of the impedance is used as a surrogate of muscle contraction, as changes are paralleled by changes in muscle volume and intracardiac blood volume.

The time from a reference point until the impedance curves meet and deviate (1) may be measured as a representation of onset of synergy. Such a point occurs at the point where the muscle shortens and blood is ejected from the heart. Acceleration from any acceleration sensor within (or connected to the surface of) the body of the patient can be used to determine onset of acceleration after a given reference point (4). Any part of the stable acceleration signal that reproduces itself from beat to beat and stimulation site may be used as a representation of onset of synergy. For example, the part of the acceleration signal used to determine the onset of synergy may correspond to any heart sound, aortic valve opening or closure.

Further, the ECG signal can be used as the reference point, from any of onset, offset or full duration of the QRS signal (3), and equally the acceleration signal can be used as a reference (2) from onset, offset or full duration (2). As described above, any such measurements can further be visualized on a surface of a heart geometry using color coded zones and a scale, relative to electrodes.

As would be appreciated, other measurements may be utilized to relate to the onset of synergy, such as measurements of the myocardial acceleration or when using a phonocardiogram or from seismocardiography. For example, echocardiography, sonography and cardiac ultrasound within or from outside the body may be utilized to measure myocardial wall velocity, strain or any other measure that repeats in each cycle to measure onset of synergy. Specifically, at least one of onset of S-wave velocity, onset of S-wave strain rate, onset of global ejection, aortic valve opening, onset of aortic flow may be measured.

Figure 4B:
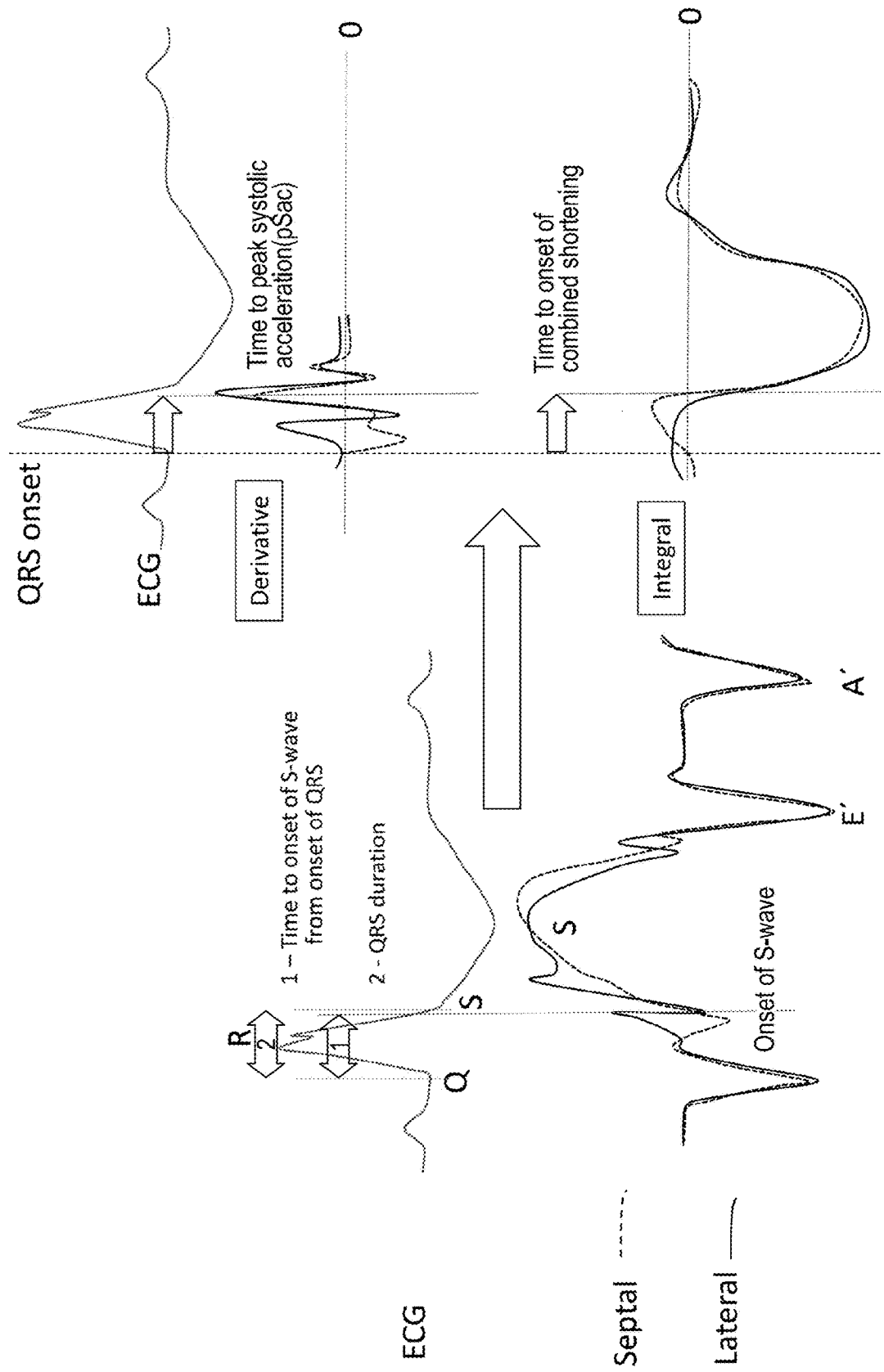
FIG. 4b shows an echocardiographic representation of time to onset of synergy.

FIG. 4b shows tissue Doppler trajectories processed in an echocardiography device to show tissue velocities, thereby showing an echocardiographic representation of time to onset of synergy, in measures such as the time to onset of the S-wave, pSac and shortening. The echocardiograph may be a representation of septal and lateral tissue velocity, acceleration and displacement. The velocity trajectories have letters assigned to them according to which part of the cardiac cycle (Wiggers diagram) they represent isovolumic contraction (IVC), the systolic velocity (S) and isovolumic relaxation (IVR). Through derivation velocity is converted into acceleration and with integration velocity is converted to displacement. Onset of S-wave and peak systolic acceleration reflects onset of synergy and can be used for determining the time from a reference to onset of synergy as described above. Any event that follows can be used for the same purpose. When strain or strain rate is calculated measurements can be performed in a similar fashion. In another example, using the system described above, myocardial dyssynchrony may be measured in the form of the time from pacing spike and/or QRS onset/offset and/or a stable portion of the QRS complex to time to peak dP/dt, or a stable portion of the pressure curve utilizing a pressure catheter or a filtered signal from the pressure trace or pressure sensor, as seen in FIG. 5a.

Figure 5A:
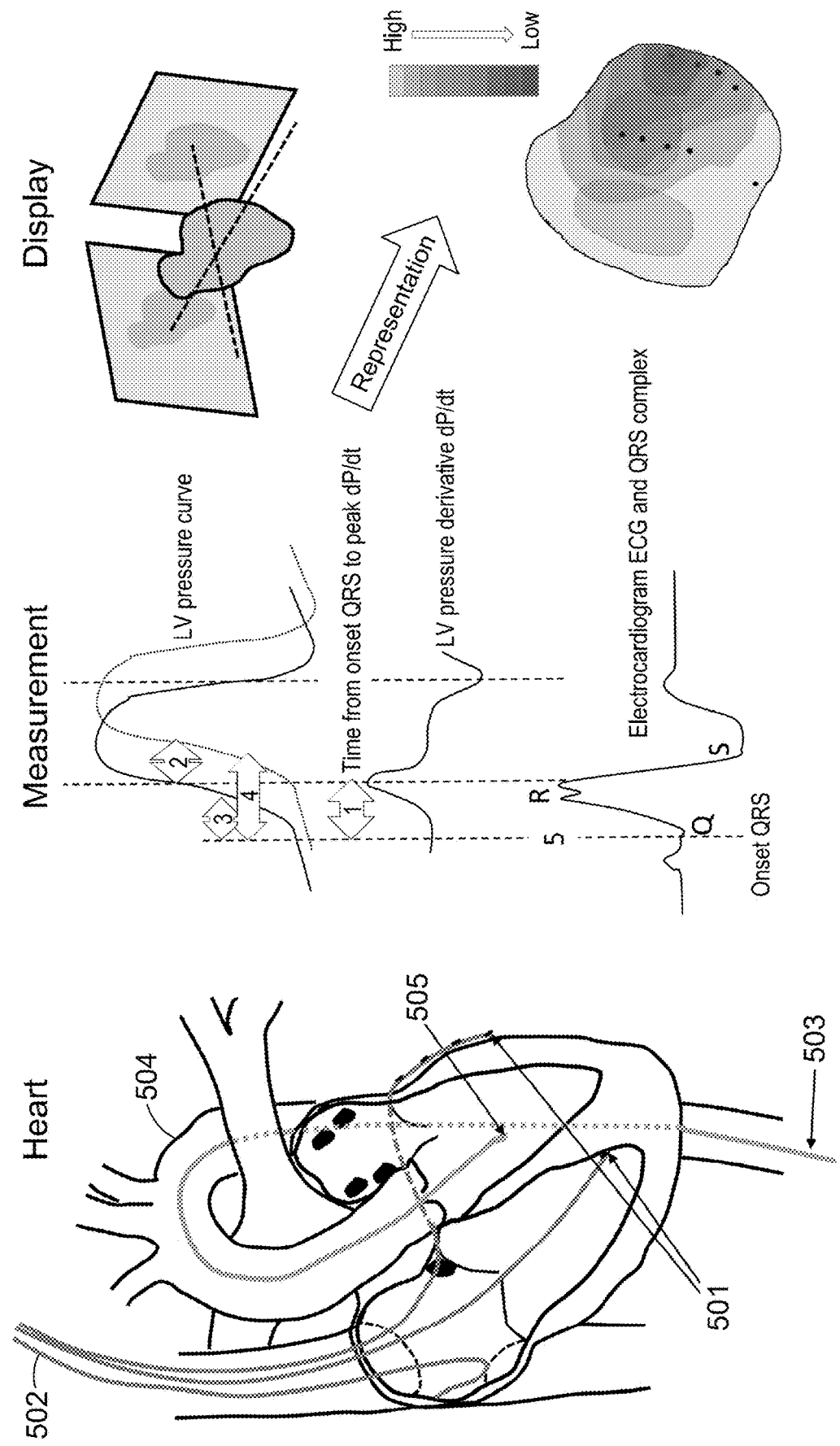
FIG. 5a illustrates how a pressure catheter located within the left ventricle can be utilized to measure ventricular pressure and the derivative of the pressure waveform.

As seen in FIG. 5a, a heart may be provided with pacing electrodes 501 connected to pacing leads 502. A left ventricular pressure sensor catheter 503 may be provided through the aorta 504 to a left ventricular pressure sensor 505. In this way, a pressure catheter located within the left ventricle can be utilized to measure ventricular pressure and the derivative of the pressure waveform, as seen in FIG. 5a. The time from a reference (5), such as the onset of the QRS curve, until the LV pressure derivative curve dP/dt peaks (1) is measured, thereby giving a representation of onset of synergy, and also effectively a measure of time to peak dP/dt/QRS. Various other measurements are also shown in FIG. 5A, as well as how they may be displayed on a 3d heart model.

Figure 5C:
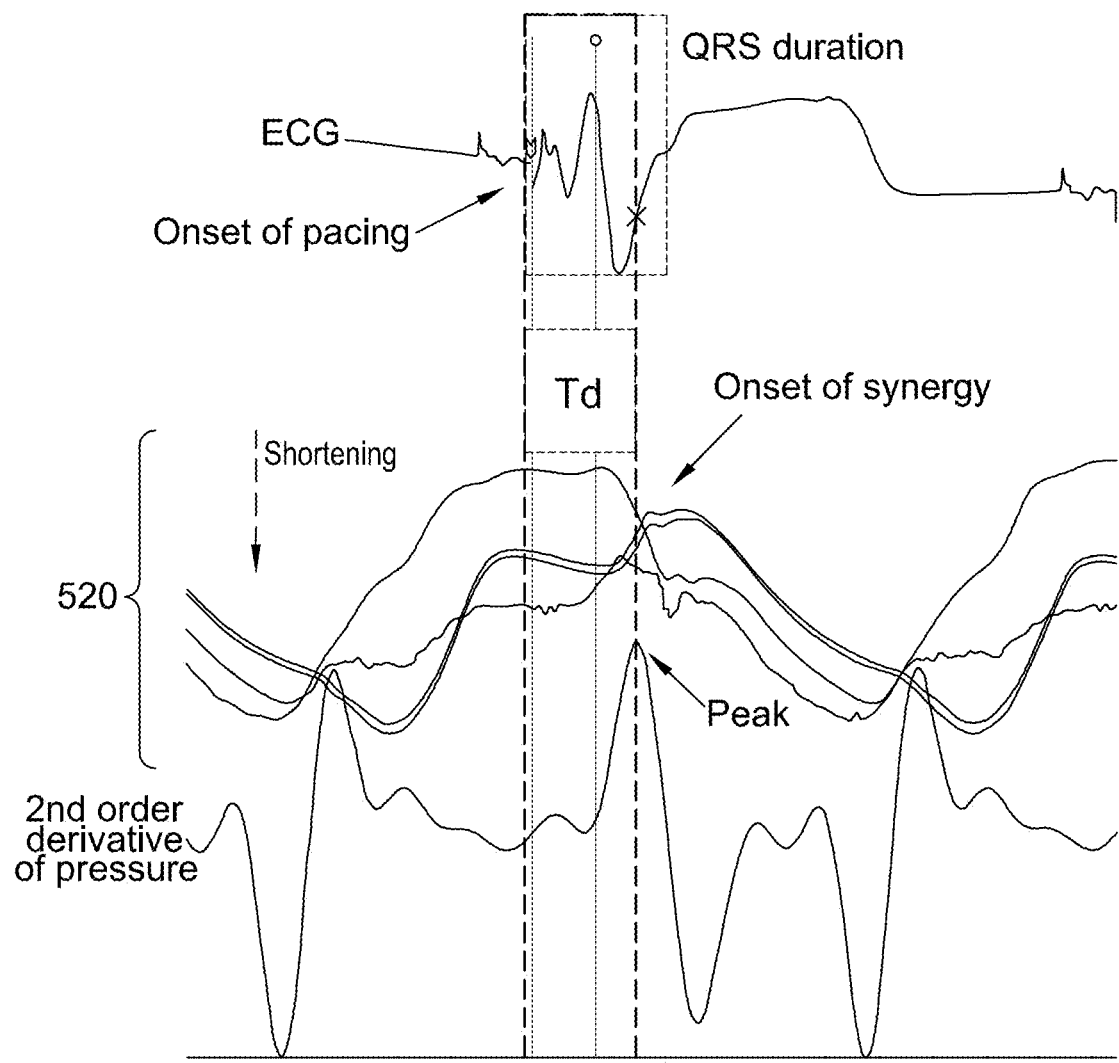
FIG. 5c shows such a determination of onset of myocardial synergy and how this relates to measuring a peak in the second-order derivative of left ventricular pressure from the measurement arrangement of FIG. 5b.

FIGS. 5b and 5c show an example of this determination of onset of synergy as measured from one animal study, which shows the onset of synergy when segment tension in the myocardium develops and stretching terminates. FIG. 5b show a model of the heart with schematic representation of sonomicrometry crystals 510 and epicardial sonomicrometric crystals 511 which are used to measure myocardial segment length trajectories in various positions in the heart, for example, as seen in the four different myocardial segment length trajectories 520 plotted in FIG. 5c. These are plotted together with the ECG trace and second order derivative of pressure for comparison purposes in FIG. 5c. It can be seen that the measured time reflecting time to onset of synergy, OoS, (i.e. the point at which segments are no longer stretching) reflects the peak in the second order derivative of pressure in the left ventricle. This is when the rate of change of pressure change in the left ventricle is at the maximum (i.e. a representation of the rapid increase in rate of pressure change), which results from the synchronous contraction of the myocardium.

A pressure curve can be compared with any pressure curve with the same time reference (5) to measure the time offset (2) between the curves or the different timing of two comparable curves with same reference, i.e. by calculating time delay 4 minus time delay 3. An example of such a comparison may be seen in FIG. 5d, wherein a reduction in time to peak dP/dt is seen with a different electrode position. Again, any measurement can be visualized on a surface of a heart geometry using color coded zones and a scale, relative to electrodes. Such a measurement may prove to be more robust than the non-invasive measures detailed above.

Figure 5D:
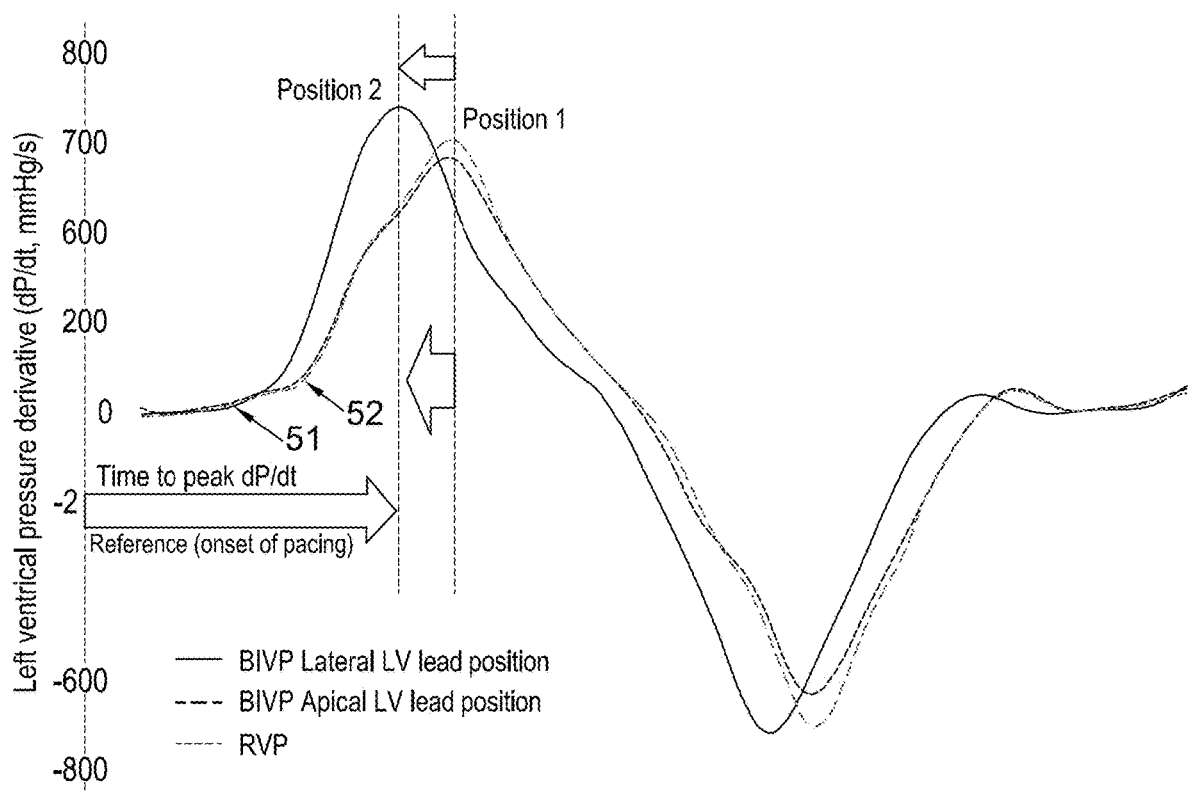
FIG. 5d illustrates the change in time to peak dP/dt with a change in position of pacing causing less dyssynchrony (position 2)

FIG. 5d also illustrates why known measures of mechanical activation are not suitable for determining synchrony, and the potential efficacy of any subsequent CRT. As can be seen, with pacing at both position 1 and position 2, the onset of mechanical activation occurs at a similar time point 51. However, the onset of synergy, i.e. the point at which the pressure begins to increase exponentially and where there is a rapid increase in the rate of pressure derivative (as seen in FIG. 5d), is significantly delayed in position 1, occurring only at time point 52, whereas this occurs soon after time point 51 in position 2. This rapid increase in the rate of pressure change reflects the point at which the pressure change begins to increase at a faster rate compared to that seen before, and occurs before the maximum value of pressure derivative. This point may be reflected in the final peak of the second order pressure derivative prior to maximum pressure, or aortic valve opening.

Such a delay may, for example, be due to dyssynchrony with isolated areas of the myocardium contracting, causing passive stretch of the myocardium, which is reflected in the comparatively low pressure increase. In this way, typical measures of mechanical activation, such as electromechanical delay (EMD) are measures of time of regional activation to onset shortening, only indicating the performance of the immediate area of myocardium. Further, in dyssynchronous hearts, EMD may vary within the heart, and this may also vary throughout the heart due to other issues, such as dyskinesia.

In contrast, onset of synergy is a global marker and reflects the phenomenon when active forces increase as shortening of segments is halted once more and more segments are electrically activated until exponential pressure rise onsets (onset of synergy) and any event that directly follows.

Typically in the cardiac cycle one would name the electromechanical delay and the isovolumic contraction as the pre-ejection phase, and keep the EMD and IVC separate. IVC is characterized that there is contraction without shortening (i.e. that the volume is constant). In dyssynchrony there is a great overlap between EMD and isovolumic contraction, and during the isovolumic contraction period there is shortening and hence typically physiological characteristics of this period is lost. The pre-ejection period is therefore very different in a normal compared to a dyssynchronous heart, as is EMD and IVC.

Figure 6:
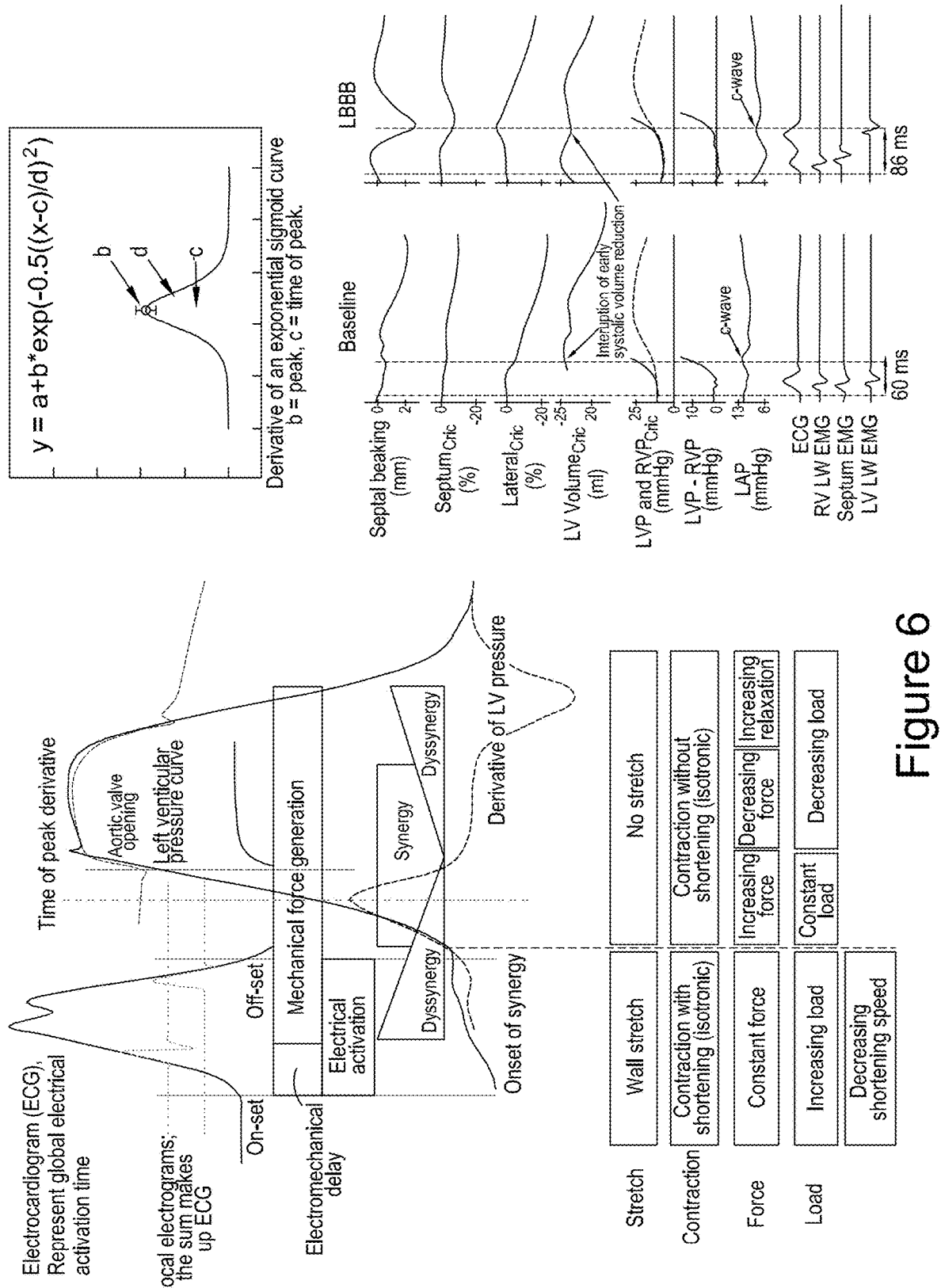
FIG. 6 shows an illustration of physiological conditions experienced during heart contraction.

An illustration of physiological conditions experienced during heart contraction may be seen in FIG. 6. As is illustrated in this Figure, the onset of synergy is illustrated related to a representative ECG, showing the on-set and off-set of electrical depolarization of the heart represented in the QRS complex.

As described above, activation of the heart muscle requires electromechanical coupling. Electrical currents passes through the heart muscle within the specialized conduction system at high speed and within conductive muscle tissue at lower speed. With conduction block, in specialized tissue, propagation delays and becomes dyssynchronous with a pattern of conduction no longer determined by the specialized conductive tissue, but by the conductive properties in the heart tissue itself (muscle, connective tissue, fat and fibrous tissue).

Electrical activation is defined from the onset of an electrical stimulus that leads to depolarization of cardiac tissue (for example, as measured from the ECG curve or a pacing artefact) to the off-set of the QRS complex. An electromechanical delay is seen between the on-set of pacing and the beginning of local contraction (and also between local electrical and mechanical activation). However, as can be readily seen in FIG. 6, such a measure does not reflect the point at which the myocardium starts contracting as a global whole, thereby generating a rapid force. Rather, the early-activated muscle tissue starts contracting, however at no load, and hence shortens with minor force development and stretches relaxed tissue to maintain the volume of the heart chamber. With more electrically activated tissue that shortens more relaxed tissues are stretched, resulting in increased tension in stretched tissue and hence load. Once the electrical activation propagates throughout the heart, and more muscle shortens, there is no more tissue to stretch, shortening and dyssynergy stops and force develops with onset of synergy with exponential pressure increase until the aortic valve opens to allow muscle shortening again.

The onset of synergy relates to this point where the shortening of the muscle stops the myocardium contracts simultaneously, beginning to increase the force at a constant volume in the heart. This occurs at some point between the earliest, and latest regional EMD or later, and could be early or late in this phase, but rather reflects the degree of dyssynchrony. In itself, this point is difficult to measure, but this point is reflected in a number of measures, for example (but not limited to), peak derivative of pressure, aortic valve opening, peak negative derivative of pressure. Such measures may have a constant relationship in time to the onset of synergy, such that the measurement of the time of such events will directly reflect the onset of synergy, and therefore may be used as a measure of onset of synergy. Therefore, by using such measurements to measure a representation of onset of synergy in time, it is possible to compare different pacing methods and their efficacy in reducing the time to onset of synergy. If shortening occurs when comparing to a different way of pacing, less dyssynchrony is present, and when the time delay gets longer more dyssynchrony is present.

Based on the results of the sensor measurements, it may also be possible to determine the most effective pacing regime to be applied. For example, a second circuit implemented in hardware and/or software may comprise an algorithm to determine how many electrodes should be included and in what position they should be placed in the pacing strategy, and further determines which pacing strategy to follow. For example, it may be determined that the most effective pacing may be achieved by CRT, His bundle, biventricular, multipoint or multisite, or endocardial pacing, or any combination of the mentioned in the form of a suggested algorithm of pacing. For example, if the onset of myocardial synergy with intrinsic activation is short, then His pacing may be desirable.

A screen may be additionally provided for visualization of the heart model with any fiducials and representations of any sensor connected. Such a system may allow for an accurate measurement of cardiac dyssynchrony by the indirect measurement of the onset of myocardial synergy described above, such as by way of an accurate measurement of Time to peak dP/dt, time to ejection, time to aortic valve opening, aortic valve closure, $dP/dt_{min}$, and/or the end of ejection. In this way, any shortening in the time to onset of myocardial synergy may be visualized with a corresponding shortening of any directly measured parameter as previously described, thereby indicating the presence of dyssynchrony. Equally, any pacing measures applied may be reversed when it is determined that dyssynchrony is not present. For example, when measuring the impedance phase and amplitude as an indirect measure of the onset of myocardial synergy in a case where dyssynchrony is not present, the impedance curves will not change with pacing at different locations because no change in contraction occurs with resynchronization.

As would be appreciated, certain limitations must be applied to the measurements to allow for meaningful data to be extracted from the measurements, and the measurements must be compared to a known time point. For example, it may be that measurements can only be performed during pacing if at least one of the following conditions apply:
1) That ventricular stimulation occurs before onset of QRS
2) That timing is corrected relative to onset of QRS
3) That the interval from atrial pacing to ventricular sensing (AP-RVs) is known.

In order to provide effective pacing, any atrioventricular (AV) delay should preferably be calculated so that AP-VP is shorter than the shortest of AP-RVs and AP-QRS. Preferably AP-VP should be calculated so as to equal 0.7*(AP*RVs), or if AP-QRS onset is known, the AV-delay interval should preferably be 0.8*(AP-QRS).

Measurements may be performed during ventricular pacing with intrinsic conduction, but only when the onset of the QRS complex is not ahead of pacing, unless the QRS onset-VP interval is corrected for in the measurement.

Measurements may be performed during atrial fibrillation with ventricular pacing when no fusion with intrinsic conduction is present. However, during atrial fibrillation pacing should preferably occur at a rate shorter than the shortest RR interval seen during a reasonable period in time so that when pacing occurs QRS complexes are not fused with intrinsic conduction, but are fully paced.

Measurements performed utilizing one sensor should only be compared with a similar sensor, unless a known correction factor is used to calibrate for differences between sensors. The detection of the reference in time should be similar, and carefully chosen to be the best representation possible of the similar time reference as compared with. A pacing stimulus may be initially negative, then positive in some configurations and equally may be initially positive, then negative in others. While the onset of the signal represents an unbiased reference in time that disregards polarity of the signal, then the maximum peak might be different in time between the two references, and the maximum should be compared to the minimum when this is the best possible detection for the signals with different polarity when compared. When intrinsic activation is detected, as in an intrinsic QRS complex, the onset of the QRS complex may be difficult to exactly define. In such a case, the earliest off-set from the isoelectric line should be chosen.

When the activation is paced, there is a delay from the pacing stimulus to the onset of activation such that there is a time delay from the onset of the pacing spike to the QRS onset. When comparing a measurement with a time reference from the QRS onset or the QRS complex with a measurement with a time reference from a pacing spike, such a time delay should be taken in account, for example by adding the same time delay to the non-paced measurement. The delay will typically be calculated based on the type of applied pacing. For example, the delay may be in the range of 10 to 20 ms.

In summary, when time reference or sensor is different between measurements, the off-set between the different time references or the sensors should be accounted for in the measurements for comparison.

In this way, it may be necessary to make sure, before measuring, that no activation occurs through the conduction system that would need to be compensated for in the measurement. The measurement of onset of synergy only takes meaning when one is not pacing the ventricle only for comparison with the surface ECG offset for determination of resynchronization potential as described.

By using the above described methods to measure the onset of synergy, it is possible to identify patients for potential CRT therapy. Traditional measures such as electromechanical activation and delay, onset of force generation, or local electromechanical delay cannot be utilized as suggested herein. As discussed, it is difficult to know exactly when to measure an electromechanical delay, as mechanical activation occurs over a wide range in time across the heart. Such issues can occur with all known methods of measuring electromechanical delay.

For example, should an isolated measure of electromechanical delay be measured using aortic valve opening, there would be many associated issues with such. In such a case, if one were to pace LV early, and allow intrinsic activation from RV, and measure from LV pace; then if pacing LV late, aortic valve opening would be determined by RV activation and not by LV, but the time from LV to aortic valve opening would be short. This gives a false measure of the efficacy of pacing in improving the physiological function of the heart.

Rather, by knowing the timing of activation through the normal conduction system, it is possible to compensate for measurements performed before pacing occurs. For example, if intrinsic activation occurs before pacing, then one should measure from onset of intrinsic and add the interval from pacing to activation, to allow comparison with other measurements when pacing.

Filtered Traces for Determination of Onset of Synergy

It has been further found by the inventors that the signature of the cardiac phases lies in the frequency spectrum after the $2^{nd}$ harmonic of the left ventricular pressure trace, where the harmonic is represented by 1/paced cyclerate (s). Early contractions at low pressures (i.e. the contractions that are associated with dyssynergy) do not produce high-frequency pressure components. However, the rapid increase of pressure that occurs with onset of synergy results in high-frequency components of the LVP trace. In this way, the crossing of the x-axis at zero for the $2^{nd}$ and above harmonics captures only the synergy components, and can therefore be used as a reference measure to compare with QRS onset or onset of pacing. Similarly, dyssynergy (being characterised in early contractions) does not produce high-frequency components.

With the onset of contraction load against initial load (L0), contraction velocity rapidly increases (Vmax). With contraction, the load increases to Lmax, at the point where V goes to 0. Tension follows a sinus wave, and with synergy tension increases above the sinus envelope.

Figures 7A, 7B:
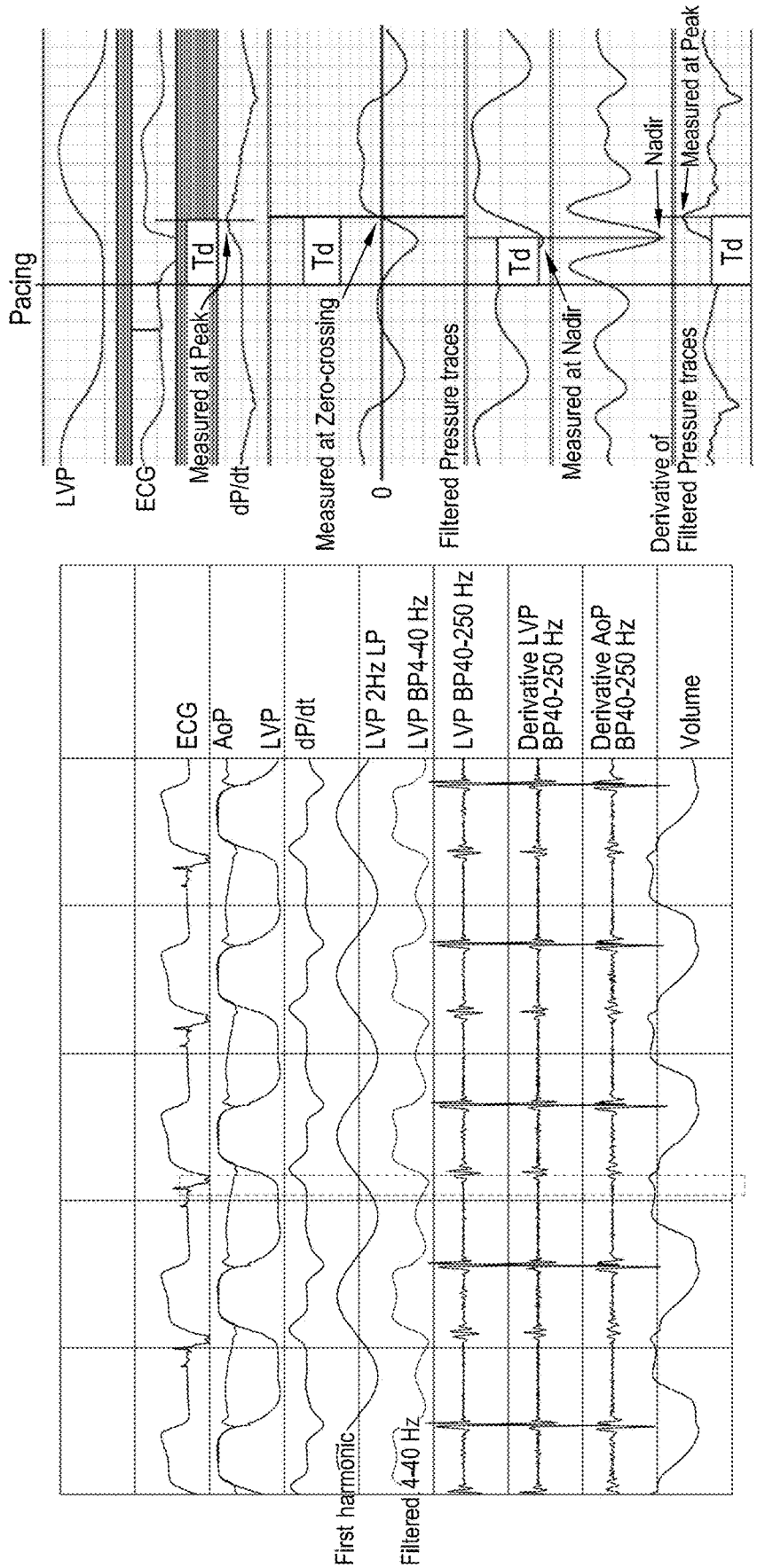
FIG. 7a shows various signals that can be derived from filtering measured traces.
FIG. 7b shows various other traces from filtered waveforms.

As can be seen in FIG. 7a, filtering of the LVP demonstrates an underlying basal sinus wave in the first harmonic that reflects the heart rate. The following $2^{nd}$ and above harmonics contain the information that shapes the sinus wave into a characteristic pressure waveform. High frequency (40-250 Hz) components initiates with onset of contraction and mid range frequencies (4-40 Hz) increase from onset of synergy until aortic valve opening. The inventors have discovered that, when the above mentioned filtered pressure range crosses 0 it is timely connected to peak dP/dt, and therefore may be representative of the onset of synergy. Synergy with increasing force and exponential pressure increase above the sinus waveform starts with onset of synergy and stops with aortic valve opening.

High-frequency components can be assessed as vibrations and translate from the left ventricle to the aorta and surrounding tissue through the solid fluids and tissue. Filtering high pressure components from aortic pressure (AoP) waveforms or atrial pressure waveforms, or detecting vibrations using accelerometers or any other sensor will therefore reflect synergy, and as long as the measurement occurs at a similar position on the measured trace/curve, for example, when the trace crosses zero, from the onset of vibrations or a certain characteristic of a waveform, or a template waveform.

FIG. 7b shows various other traces from various filtered waveforms, and how they may be used to give various measures of Td, each of which relates to the onset of myocardial synergy, OoS. By taking one of these measures, and measuring how it varies with pacing, then it is possible to identify the presence of dyssynchrony in a patient due to the constant delay between the specific measure of Td and the actual event of onset of myocardial synergy.

Figure 8A:
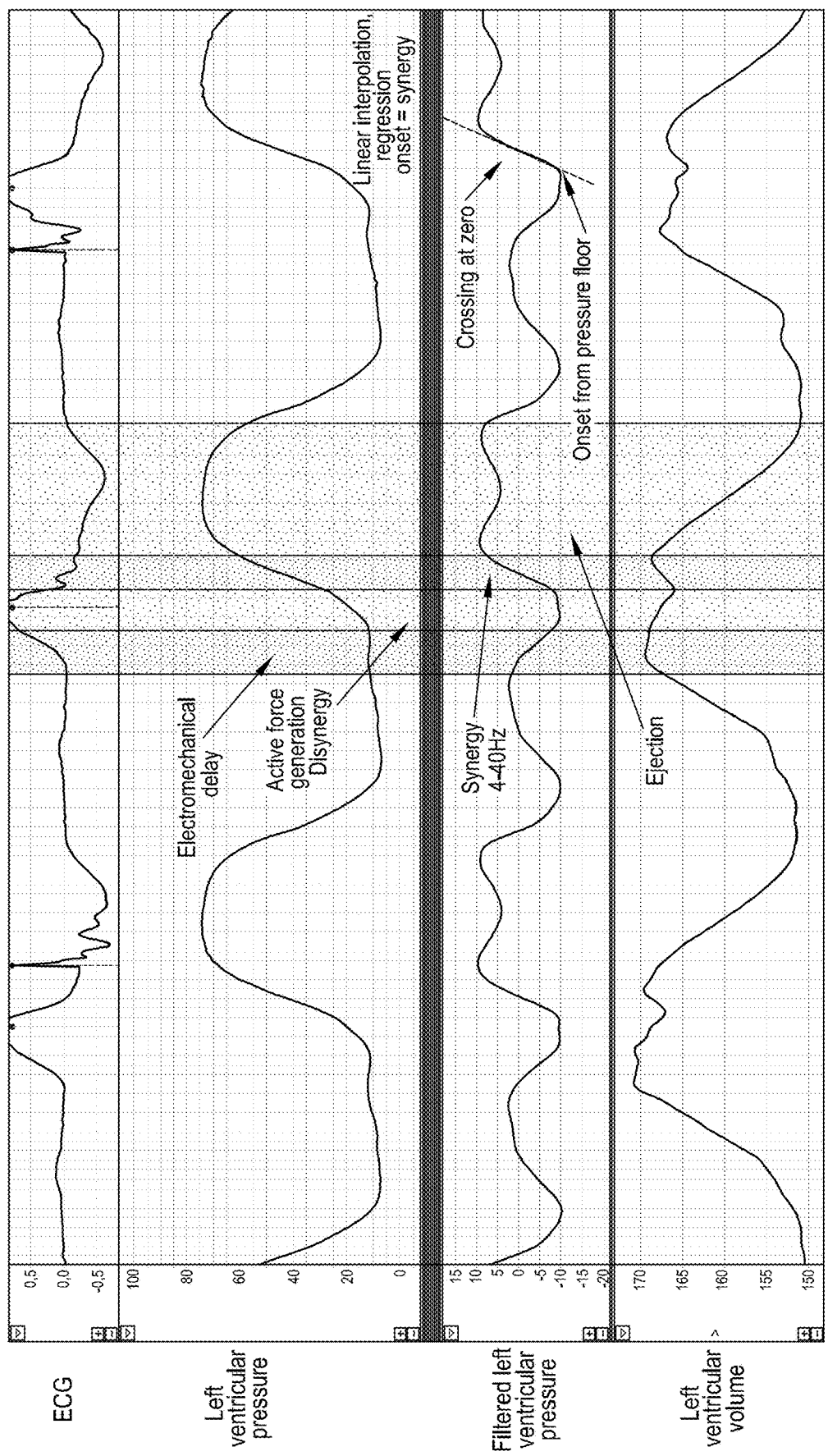
FIGS. 8a, 8b and 8c show various examples of how traces may be utilised to determine the onset of synergy, or a signal indicative thereof.
Figure 8B:
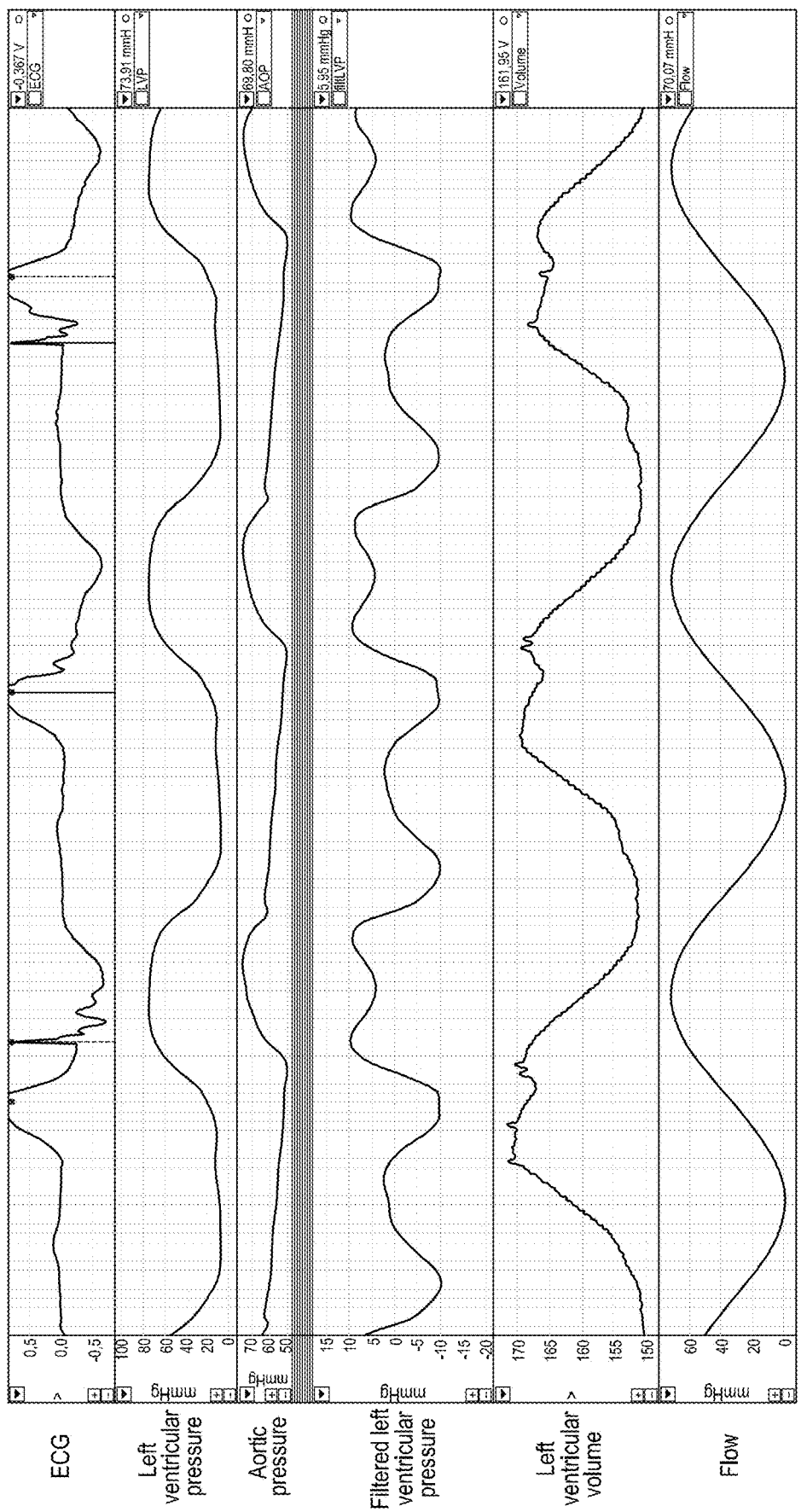
Figure 8C:
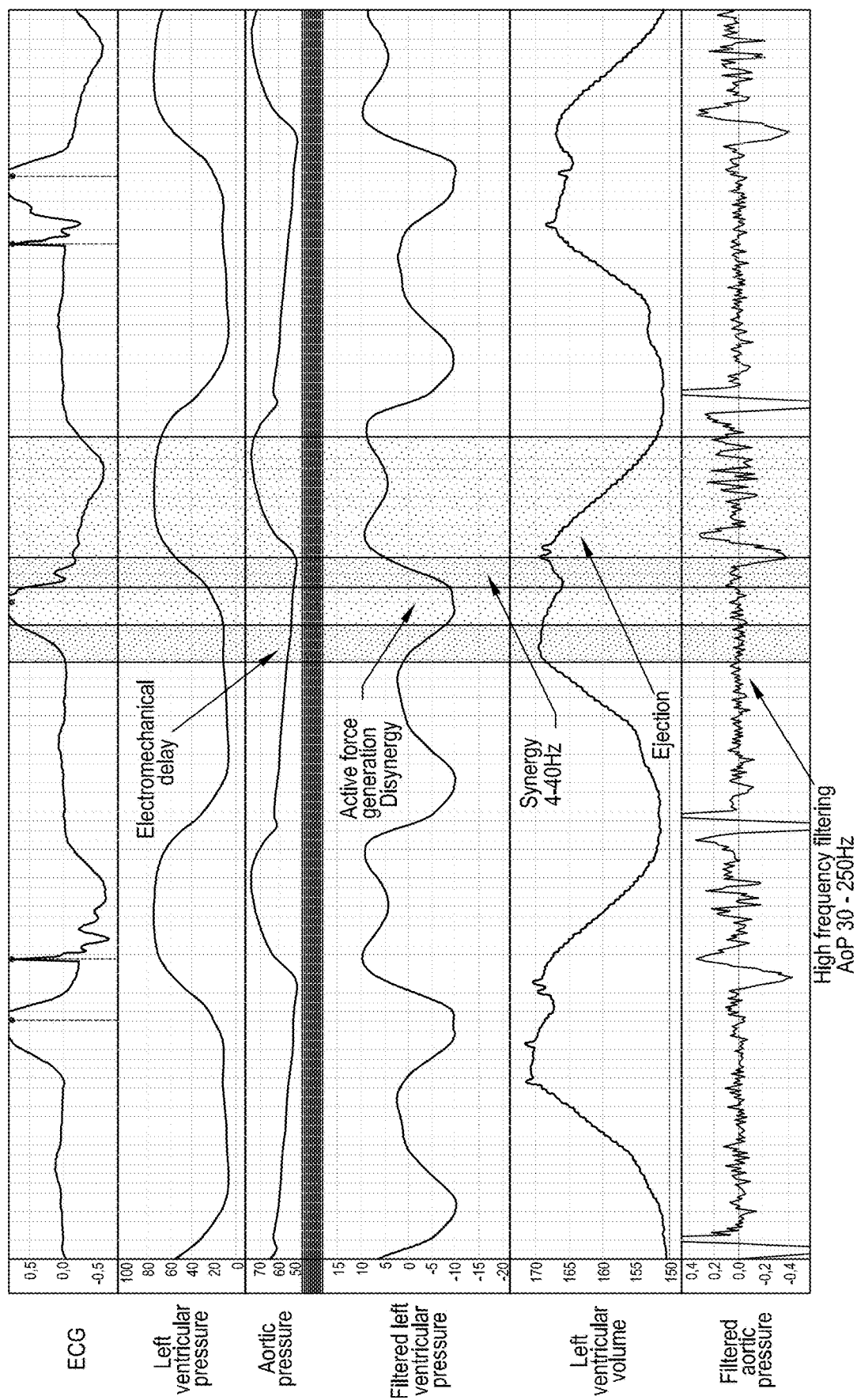

Further information regarding the onset of synergy may be deduced from filtering various measured signals, as seen in FIGS. 8a, 8b and 8c.

Starting from FIG. 8a, each phase discussed above is annotated on the traces. Initially, there is a delay between the onset of pacing seen on the ECG trace, and the beginning of increase in LV pressure.

Then, there is dyssynergy when the mechanical force begins to slowly increase, due to the passive stretch of the myocardium. Low-frequency components in left ventricular pressure (less than $2^{nd}$ to $4^{th}$ harmonics of the heart rate) are typical for dyssynergy. With dyssynergy there is onset of active force with sarcomeric cross-bridge formation at high rate in specific regions of the heart that result in shortening of the sarcomers (and myofibrills) that leads to stretch of not yet contracting segments and regions of the heart, with only a small increase in pressure resulting (with low-frequency components), as discussed extensively above.

The onset of synergy is reflected in a rapid increase of force at a relatively constant volume, which is reflected in the increased rate of increase of pressure. With activation of all segments and synergy, pressure increases rapidly (with high-frequency components) when approaching isometric (and isovolumic) conditions as load increases. This can, for example, be seen in the identifiable change in the rate of increase of the left ventricular pressure between the initial (relatively) slower increase in pressure due to dyssynergistic contraction and the exponential increase of the synergistic contraction. This may be seen in a step change in the rate of increase of the left ventricular pressure, and/or may be identified by further post-processing of the data. For example, this change can be measured in the frequency range, as the frequencies contained in the pressure trace increase when there is a step change in the pressure change. This occurs beyond the low order harmonics of the frequency spectrum, and the OoS may become evident when low order harmonics are filtered with a low pass filter or band pass filter. Filtering at, for example, a band-pass 4-40 Hz removes the low, slow frequencies that are associated with dyssynergy and the onset of synergy may be seen as the onset of the pressure increase that leads to, or is directly prior to aortic valve opening or maximum pressure. Alternatively or additionally, this may be seen in the peak second order derivative of pressure rise in the left ventricle.

This change in rate of pressure increase is because of increasing and exponential cross-bridge formation while passive stretched segments tension increase, either because depolarization or because elasticity model reaches its near maximum. Rapid cross bridge formation with isometric or eccentric contraction leads to high-frequency components in the pressure curve frequency spectrum, reflecting onset of synergy. This phase of the cardiac cycle may be seen when filtering LVP with high pass filter above the $1^{st}$ or $2^{nd}$ harmonics. The filtered and characteristic waveform has a near linear increase, from onset of synergy to crossing 0, and continues with a linear increase up to aortic valve opening. The line of linear increase reflects the period with synergy, crossing zero at halfway in the phase, which corresponds to peak dP/dt as described above, and onset of synergy is reflected in where this line starts to rise above the floor of the filtered pressure curve or at its nadir.

Ejection then occurs with the opening of the aortic valve, thereby reducing the LV volume at a relatively constant pressure. Another example trace is seen in FIG. 8b, which has been annotated to show each of the above phases in FIG. 8c. FIG. 8c also shows a high-frequency filter of the aortic pressure, which also shows peaks in the high-frequency domain at points that could be used as a measure of OoS (onset of synergy).

Other data may alternatively or additionally be analysed in order to determine a measure of the onset of synergy. In this way, other measures may be used either as a supplement to measuring pressure traces, and determining therefrom the time of onset of synergy (or an event related thereto) as considered above, or as an alternative to pressure traces. For example, acceleration data may be analysed, such as that provided by an accelerometer sensor, as is illustrated in FIGS. 26 to 28.

FIG. 26 shows various traces that can be extracted from accelerometer data. Graph 3302 shows raw acceleration, from which a wavelet scalogram 3303 may be produced, which shows the frequency spectrum over time. Graph 3304 shows the left ventricular pressure (LVP) and the aortic pressure (AOP), graph 3305 shows LV volume, and graph 3306 shows a detected ECG. FIG. 27 shows a zoomed in extract 3404 of the bottom trace of the acceleration of graph 3302, and a zoomed in extract 3401 of the wavelet scalogram of graph 3303. From the wavelet scalogram, a trace 3402 may be derived which represents the center frequency for each time point. It has been discovered that the peak of this frequency 3401 within a given time frame accurately represents the time of the onset of synergy. This may be plotted as point 3301 against several traces, as shown in FIG. 26. Whilst FIG. 27 shows only a single axis of acceleration (in this case, the x-axis acceleration) it would be appreciated that a similar analysis could be performed for all axes, and only a single axis is illustrated for clarity purposes.

Figure 28:
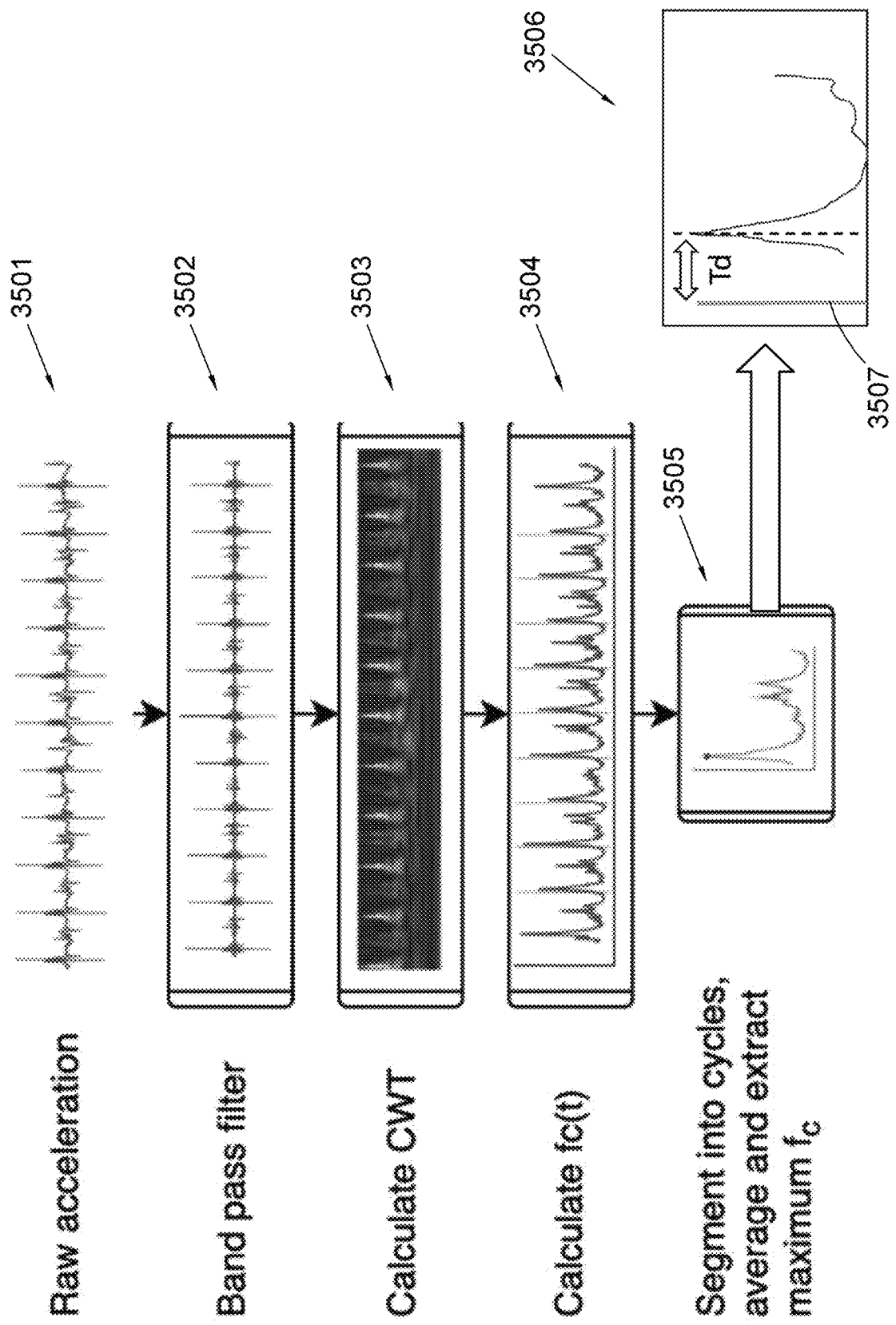
FIG. 28 shows an example analysis that may be performed to acceleration data, so as to calculate a time to onset of synergy.

FIG. 28 shows an example analysis that may be performed to acceleration data, so as to calculate a time to onset of synergy. For each axis, raw acceleration is measured. A plot of the data from one axis of raw acceleration against time may be seen in graph 3501. The raw acceleration data then may be band pass filtered, resulting in the data seen in graph 3502. From such a band-pass filtered dataset, the continuous wavelet transform CWT) may be calculated, resulting in graph 3503. The center frequency trace fc(t) is then calculated from the CWT as seen in graph 3504. By splitting the fc(t) trace into cycles 3505 corresponding to the heartbeat, averaging each cycle and extracting the time of the peak fc(t), it is possible to determine the time-to-onset of synergy (Td) as seen in graph 3506. The time to onset of synergy may be measured from any suitable reference time, such as the QRS-onset, 3507.

As would be appreciated, acceleration data may be used as a standalone measure. or alternatively, it may be used in combination with other measures such as the pressure traces, and/or filtered pressure traces so as to determine the time until the onset of synergy.

Further Discussion of the Onset of Synergy

As would be appreciated from the above (and following) description, the point of the onset of synergy may be determined in a number of ways, essentially by detecting the point (or a point directly related to) the time during cardiac activation where the myofibrils work in synergy and begins to contract isometrically as most of the myocardium stiffen from either active contraction or passive stress (increased resting tension), which results in an exponential pressure increase (rapid pressure rise) within the heart. The following example methods are not intended as an exhaustive list of ways in which the point of onset of synergy can be measured, and utilized, but are rather presented as examples to illustrate the present invention.

When it is possible to determine the point of the onset of synergy, and how it changes with various types of treatment (for example, with intrinsic rhythm, RV pacing, LV pacing and/or BIVP amongst others), it is possible to identify whether the concept of synergy exists within a patient. Where it is identified that the time to onset of synergy can be shortened, then it may be said that "synergy" exists for a determined pacing regime, and therefore that a patient may benefit from treatment.

It is important to note that, as would be understood by the skilled person, the methods presented herein do not require the presence of a patient, nor do they explicitly require the collection of data from the patient. Whilst patient data is required, the measurements may be (and typically are) performed after the collection of data, and away from the patient. It is therefore envisaged that the inventions described herein may be performed on pre-existing data sets, without the presence of a patient. In this way, an examination of a patient involving the collection of data is not integral to the present invention. Any reference herein to steps that involve the collection of data would be understood such that they refer to steps and measurements that have already been performed. In this way, the methods herein may be considered as methods of processing such data so as to give technical information regarding the patient, which may then be used for in planning how best to give/improve the prognosis of the patient from whom the data was previously collected.

Cardiac Resynchronization Therapy (CRT) is understood, and can be achieved in multiple ways either by direct stimulation of the conduction system of the heart chambers (left bundle branch or His bundle) or with stimulation at more than one site (resynchronization therapy). CRT can be permanently applied with a pacemaker or temporarily with electrophysiology catheters or pacing leads to perform artificial stimulation of the myocardium. CRT also implies that there is an intention to perform resynchronization with any kind of artificial stimulation of the heart chamber or chambers. One may also consider intrinsic conduction in a patient as resynchronization, and compare the intrinsic activation to an artificially paced beat or an ectopic intrinsic beat in the heart of the patient.

The calculation of the time of the onset of synergy may be utilized as a prognostic biomarker, in that if a patient (after having Cardiac Resynchronization Therapy) has a late onset of synergy during stimulation (with CRT or pacing electrodes), then the prognosis of the patient will be poor. In this way, it could be said that there is described a method to determine the prognostic results from resynchronization therapy, from data that has been obtained from a subject when controlling their heart rate and sensing the ventricle, either by stimulation of the atrium or by sensing the atrial electrical activity while sensing the ventricle. Then CRT is applied and the signals from sensing electrodes and sensors are collected. Measurements of the intervals and comparison of the data is performed in a processor outside of the body after collection of the data to determine if the pacing pulses have provided synergy or not. The finding of an improvement in synergy is present when a first interval is shorter than another interval. If with CRT, synergy is present, then the prognosis is determined to be good.

As described above, it may be desirable that, for an accurate measure of the onset of synergy, it is ensured that the electrical activation and resulting pressure increase in a data set results only from the stimulated sites and not from the intrinsic activation of the heart. Therefore, in combination of the methods that are considered herein or alone, pacing electrodes may have been placed in the atrium and ventricle(s), and pacing may be applied from the atrium and/or, for example if atrial fibrillation is present, then from the ventricle, both pacing being at rates 10% above the intrinsic heart rate. Therefore, from data received during pacing at a higher rate that the intrinsic activation, an automatic detection of a set of intervals may occur, for example:

Detecting of the atrial paced to the surface ECG onset and offset

Detecting the atrial paced to the right ventricular sensed interval

Detecting the atrial to the left ventricular sensed interval

In order to provide a fixed interval until the chambers are activated, and ensure that intrinsic activation does not interfere with the measured response, there may be pacing with a paced atrial to paced ventricular interval at 40% shorter than any of the detected intervals. This ensures that the chambers are not activated by intrinsic activation, and therefore that the paced activation and the intrinsic activation are not competing, which can lead to an inaccurate measure of the time of the onset of synergy.

The measurements above relating to the identification of the onset of synergy may be utilized in various different ways to give an indication of whether pacing results in (an increase of) synergy. Other ways of illustrating and/or measuring the point of the onset of synergy are envisaged, such as that of FIG. 29. The onset of synergy results in a repeatable pressure increase that follows a trajectory over time up until peak dP/dt that can either be represented as a template (as in FIG. 29) or an equation. By comparing the pressure curve before and after CRT, and shifting the resulting curves (with/without CRT) such that the pressure curves then track each other, it is possible to determine the delay to the onset of synergy, by the amount it was necessary to shift the curves so as to match each other. This time delay remains constant throughout the pressure curves.

Figure 29:
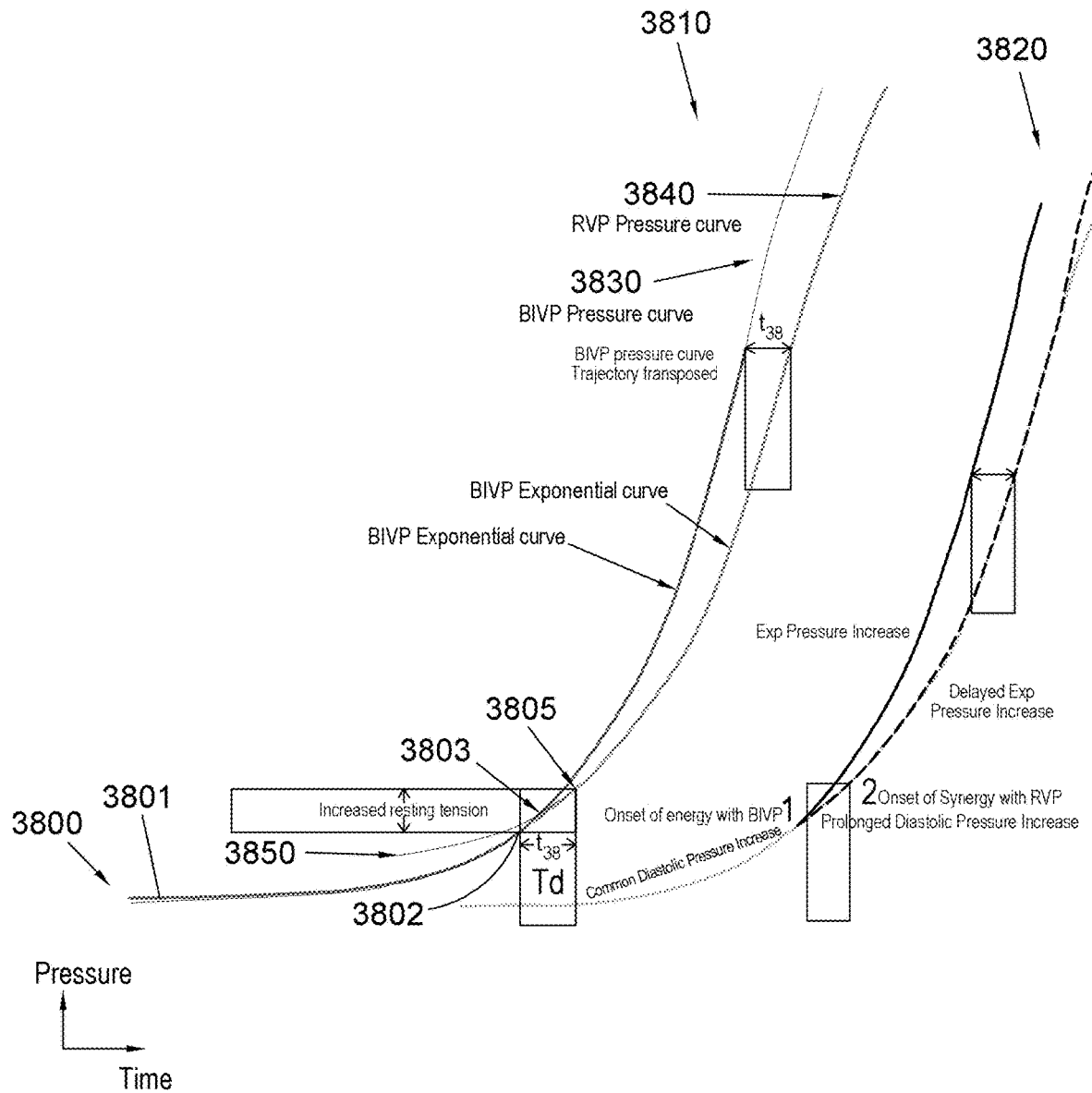
FIG. 29 shows a comparison of two pressure curves resulting from different kinds of pacing.

For example, FIG. 29 shows a comparison 3810 over time between a pressure curve that results the pacing the right ventricle 3840, and from bi ventricular pacing 3830. As can be seen, from point 3800. The curves for RVP 3830 and BIVP 3840 are parallel, and are both aligned by a time point 3801 that is a common point of atrial stimulation in both responses. Then, the measurement of a subsequent pressure rise follows. Said another way, although the curves for RVP and BIVP relate to different heart beats, they are fitted together relative to their stimulation timing, and the pressure level is adjusted to fit the diastolic portion of the curves prior to ventricular pacing.

From comparing these curves, whether synergy is present (i.e. whether the time to the onset of synergy has been shortened by providing BIVP), and the timing of the onset of synergy may be measured by finding the point of deviation between the fitted pressure curves that are compared.

As can be seen in FIG. 29, and specifically in the comparison 3810, whilst the RVP pressure curve 3840 and BIVP pressure curve 3830 are parallel (follow the same trajectory) to begin with, they begin to deviate from point 3802, which represents the time of the onset of synergy with BIVP.

The inventors have recognized that, despite the difference in timing of the onset of synergy, the pressure rise preceding the onset of synergy will follow a common diastolic pressure increase, and then the pressure rise resulting from the onset of synergy will always have the same shape (i.e. follow the same mathematical equation on a plot between pressure and time beginning from the onset of synergy), despite the delay, and change between the relative resting tension. Therefore, from the determination of this point, it is possible to fit this portion of the pressure curve resulting from BIVP onto the corresponding portion of the pressure curve resulting from RVP. From this, it is possible to use the amount that it has shifted in order to determine pertinent information about how BIVP has changed the onset of synergy, and thereby determine whether synergy is present with such a method of pacing.

For example, as shown in FIG. 29, a portion of the BIVP pressure curve 3830 can then be fitted onto the corresponding curve relating to RVP that follows the point 3802 where the BIVP and RVP pressure curve deviate (which is denoted by an arrow on the BIVP pressure curve 3830). This shifted BIVP pressure curve 3850 crosses the original BIVP pressure curve 3830 at point 3803, which indicates the onset of exponential pressure rise. Points 3802 (i.e. the onset of synergy) and 3803 (the resulting onset of exponential pressure rise) are the points that mark the timing of deviation between the RVP pressure curve 3840 and BIVP pressure curve 3830. In the example of FIG. 29, the BIVP pressure curve 3830 is shifted up and to the right to shifted pressure curve 3850, such that the portion of the BIVP pressure curve following point 3802 (up until peak dP/dt), to the point where the shifted pressure curve 3850 matches the RVP pressure curve 3840. The portion of the BIVP pressure curve following the onset of synergy 3802 fits on the RVP pressure curve starting at point 3805, and from this point follows the same curve as the RVP pressure curve. Therefore, as stated above, as the increase in pressure following the onset of synergy in the same patient follows the same pressure rise until peak dP/dt, it may be said that the onset of synergy in the RVP pressure curve occurs at point 3805.

By comparing the difference in the onset of synergy during BIVP (at point 3802), and the onset of synergy during RVP (at point 3805), it is possible to obtain valuable information regarding how the change in pacing effects the function of the heart. The time delay ($t_{38}$ in the example of FIG. 29) can be used to show that BIVP results in a shortening of the time to onset of synergy in a patient, thereby indicating how a pacemaker may be programmed to improve the prognosis of a patient. Additionally, the vertical offset between points 3803 and 3805 shows the increase in resting tension in the myocardium that results from dyssynchronous contraction of the ventricles, and passive stretching of the heart muscle in advance of the onset of synergy.

FIG. 29 also shows comparison 3820, which is a simplified version of comparison 3810. This shows the common diastolic pressure increase between BIVP and RVP, and then the point of deviation 1 (i.e. the onset of synergy with BIVP) leading to exponential pressure increase with BIVP. The portion of the BIVP curve following point 1 may be fitted onto the corresponding portion of the RVP pressure curve, indicating the onset of synergy with RVP at point 2, which results in the (comparatively) delayed onset of synergy with RVP. This time delay remains constant throughout the BIVP and RVP pressure curves.

As would be appreciated by the skilled person, this process can be automated and for the data resulting from any number of pacing regimes, whether by a simple matching of the curves (for example, by the fitting of a template to the pressure trajectory with a least squares method) or by a comparison of the mathematical formulae that represent the curves. There can be an automatic detection in the data of the exponential pressure rise, up to the peak dP/dt which results from the onset of synergy. From this, there may be an automatic calculation of the exponential formula that fits the pressure curve, and from this, the time when the exponential formula fits one of a number of curves can be determined. For example, there could be a template match, and there be calculated a time offset between the exponential formula and the template matches, or equally a cross-correlation between other measures. Additionally, whilst this is shown in the example of FIG. 29 with regards to the raw pressure data that can be obtained from the heart, it would be appreciated that these measures are reflected in all pressure measurements, including filtered pressure measurements. For example, as there exists a common mathematical equation that can describe the pressure rise that results from the onset of synergy for a given patient, the time delay to the peak dP/dt following various kinds of pacing can be compared so as to give an accurate representation of how pacing affects the time delay to the onset of synergy, and therefore be used to advised on a suitable pacing method and a programming of a pacemaker for the most effective treatment.

From the above, an output of the time to onset of synergy and the offset between exponential pressure rise curves, or offset between band pass filtered curves, or between derivatives of pressure curves can be provided. If the onset of synergy is shorter than just in RV pacing then it might be decided that it would be beneficial to program an implanted pacemaker to pace from both RV and LV channels. Equally, it might be recommended to modify pacing so as to occur with multiple channels, and the delay to onset of synergy is shorter with any multipoint/multisite pacing, then it might be suggested to program the pacemaker to pace in a multipoint/multisite way.

Figure 30A:
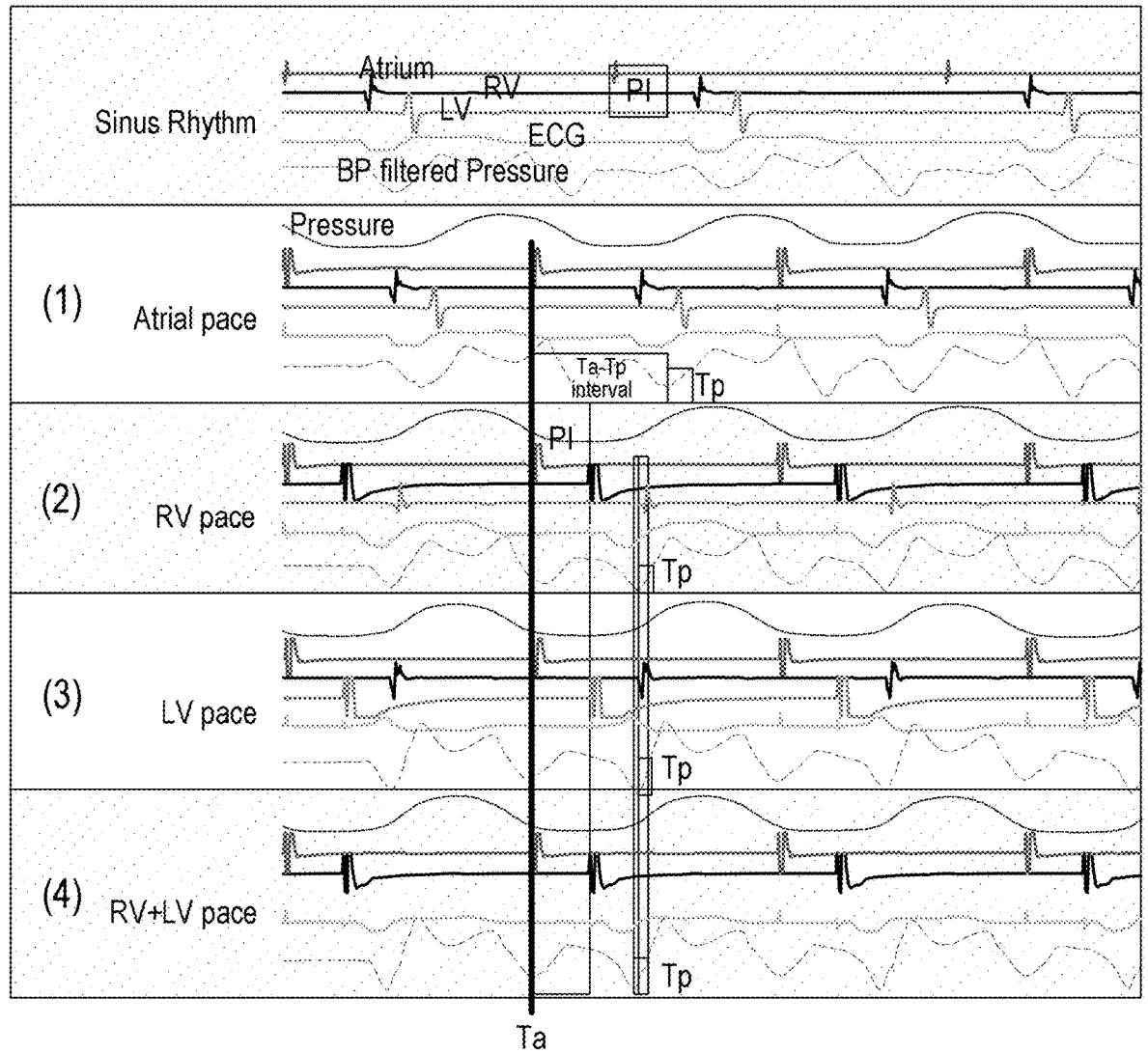
FIG. 30a shows various traces in which the advancement of the zero crossing of the pressure curve can be detected.
Figure 30B:
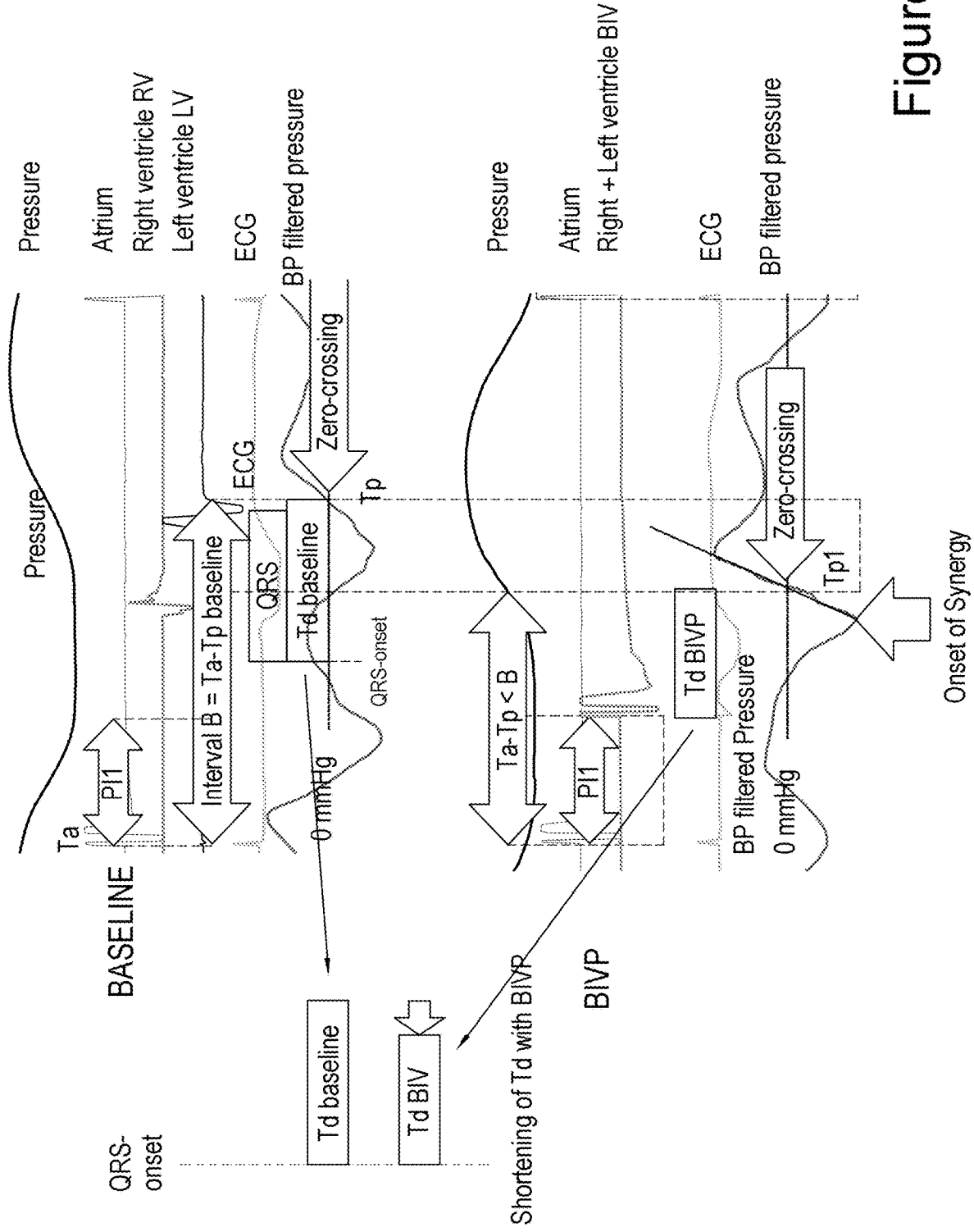

FIGS. 30*a* and 30*b* show another way in which an advancement in the onset of synergy can be detected, specifically by an advancement of the zero-crossing of the filtered (band-pass) pressure curve (Tp) with stimulation from both LV and RV compared to when either LV or RV is paced, and therefore in this example, it may be said that synergy is present and therefore that it may be desirable to undergo CRT using BIVP. FIG. 30*b* shows a more detailed view of the traces of FIG. 30*a*, for clarity and ease of reference.

FIG. 30*a* displays traces that have been gathered in 5 separate cases, one with the natural sinus rhythm, on with atrial pacing, one with RV pacing, one with LV pacing, and one with RV and LV pacing (BIVP).

As discussed above, synergy is the phenomenon by which stimulation by a given pacing regime leads to a sooner onset of synergy. This may be identified by the advancement of rapid pressure rise, which can be identified by a leftward shift in the zero-crossing of the band pass filtered pressure curve. The onset of synergy (OoS) is the corresponding onset of pressure rise along the tangent of zero, as can be seen in Figure Therefore, a leftward shift in the zero-crossing of the BP filtered pressure curve is directly related to the OoS, and therefore can be said to correspond to a leftward shift in the OoS.

The OoS can be compared to the rapid pressure rise with pacing or with intrinsic rhythm from onset of electrical activation, and if OoS is advanced when compared to the other then it may be said that more synergy is present. FIG. 30b shows that, with BIVP Ta-Tp is shorter then Ta-Tp at baseline, confirming that Td is not a result of intrinsic conduction. Td measures the time from electrical activation to Tp and is a referenced interval of the time to OoS. As can be seen in FIG. 30b Td is shorter with BIVP compared to Baseline, synergy is present with BIVP and it may be desirable to undergo CRT using BIVP.

In order to populate the traces of FIGS. 30a and 30b, data related to the OoS may be collected from a pressure sensor in the left heart chamber and subsequently analysed, relative to various timings of the heart that are collected from electrodes placed within the atrium and/or right ventricle and left ventricle, as well as surface electrodes that have collected a corresponding ECG signal.

As above, the pressure signal can be band pass filtered at 4-40 Hz to remove the high and low frequency waves, and simplify the subsequent analysis. The corresponding ECG signal, to which the pressure signal is aligned and compared.

The ECG signal is passed on to a processor unit, and a time of atrial intrinsic activation/stimulation (Ta) can be determined. The signal from the pressure sensor is also provided to a processor unit, where the value of 0 can be determined from the BP-filtered pressure waveform, and the time may be extracted (thereby giving a measure of Tp). From this, a baseline interval B can be calculated, as equal to Ta-Tp (i.e. the time between activation and zero crossing of the pressure curve for intrinsic activation). Intervals PI, Ta-Tp, Td and QRS-onset are demonstrated in FIG. 30b.

Then, following pacing of the heart chamber from a first electrode (for example, one of the electrodes positioned in the RV or LV) at a set pacing interval (PI1) after Ta (but before QRS-onset), a corresponding Tp1 may be calculated. The value of 0 is determined from the BP-filtered pressure waveform and the time is extracted (Tp1).

The pacing interval (PI1) is reduced, typically to more than 20 ms before QRS-onset, until the corresponding interval Ta-Tp (Ta-Tp1) is less than B (the baseline interval between activation and zero crossing of the pressure curve for intrinsic activation). For example, the pacing interval that results in a Ta-Tp<B is PI1, and the corresponding Ta-Tp interval (Ta-Tp1) at PI1 equals T1.

Then, pacing of the heart chamber is performed from a second electrode (i.e. another one of the electrodes) at a set pacing interval (PI2) after Ta, and the corresponding Tp2 is registered. In this way, the zero-crossing is collected from the corresponding BP-filtered pressure waveform and the time is extracted (Tp2). Again, the pacing interval (PI2) is reduced until the corresponding interval Ta-Tp (Ta-Tp2) is less than B, which is again typically more than 20 ms. For example, the pacing interval that results in a Ta-Tp<B is PI2, and the Ta-Tp (Ta-Tp2) interval at PI2 equals T2.

Then, pacing of the heart chamber is performed from multiple electrodes (for example, both the RV and LV electrodes) relative to Ta at a set PI3, which corresponds to the lower of PI1 and PI2. Then T1 and T2 is repeated with PI3 with stimulation at each electrode, the value of 0 is collected from the BP-filtered pressure waveform and the time is extracted for T1 and T2. Then stimulation of combined electrodes with PI3 and the corresponding interval Ta-Tp (Ta-Tp3) is registered. The resulting Ta-Tp (Ta-Tp3) interval at PI3 equals T3, and it may be said that synergy is present if T3 is lower than T1 and T2 at PI3. If this is the case, then it is desirable to perform synergistic pacing from multiple electrodes in CRT. Conversely, if T3 is higher than T1 or T2 then synergy is not present and synergistic stimulation cannot be performed. Following a positive determination for BIVP, a pacemaker can be programmed with corresponding intervals for PI3 relative to Ta for synergistic stimulation of the heart. The steps can be repeated with different electrode positions to find the shortest interval T3 compared to T3 from different electrode positions.

Finally, a Tbaseline can be calculated by measuring the interval from QRS-onset to Tp and adding 15 ms+PI3. Td BIV equals removing the interval PI3 from T3, and Td baseline equals removing the interval PI3 from Tbaseline. It may be said that synergy is present if T3 is lower than T baseline (i.e. that the time to Td has been shortened when comparing between pacing, and intrinsic conduction). In sum, when calculating Td it may be said that synergy is present when Td BIV is lower than Td baseline. When pacing the specialized conduction system with only one electrode (T2 and PI3), it can be said that synergy is present if T2 is lower than Tbaseline.

Similar data may be employed for synergistic pacing from different PIs from a pacemaker. In such a method, a pacemaker is programmed with corresponding intervals for PI1 for the first electrode, and PI2 for the second electrode to provide synergistic pacing to the heart. Each PI must result in a corresponding Ta-Tp shorter than B. The value of 0 is collected from the BP filtered pressure waveform and the time is extracted (Tp1). The onset of the QRS complex is identified and time is extracted (Tqrs) at baseline and with each pacing. Td baseline is the Tqrs to Tp interval with intrinsic activation without pacing the heart chamber. Td for the pacing electrodes and PIs equals the time interval from Tqrs to Tp1. Then a new PI3 is added for any of the electrodes or a new electrode and pacing is provided from two or more electrodes, a new Tp2 and corresponding Td (Tqrs to Tp2) is calculated. Again, a lower Td indicates that more synergy is present with the corresponding PIs. If Td with pacing (BIVP) multiple electrodes and PIs is lower than Td baseline then Synergy is said to be present with pacing and the pacemaker can be programmed to stimulate the heart at the corresponding electrodes with the corresponding PIs. If synergy is present, then the pacemaker can be programmed to stimulate at the two electrodes. As would be readily appreciated by the skilled person, further, additional electrodes and PIs can be added and stimulated simultaneously, or with a delay between the electrodes (configurations). Typical delays (PIs) are between 10-60 ms.

In such a case, various configurations may be noted. A configuration that shortens Td below all other time intervals is noted as improved synergy, and therefore the pacemaker can be programmed to stimulate electrodes with the applied configuration that results in the soonest/earliest Onset of Synergy.

Such a method may similarly be performed with the detection of synergy from the pressure curves, as described more fully above with regards to FIG. 29. If two electrodes are simultaneously, or with a delay, stimulated, then the earliest identifiable part of the unchanged pressure curve (for example, above 80% template match) (including nadir, 0-cross, template, min max), should be noted and compared to stimulation and configuration from any other electrode pairs. If a pair of electrodes stimulated with a configuration advances a part of the curve compared to the others, then synergy is present with such a configuration, and the earliest part of the curve that is advanced is onset of synergy and is the time point to which measurements are performed. A pacemaker can be programmed to perform stimulation at the point of electrode positions and configuration.

Figure 31:
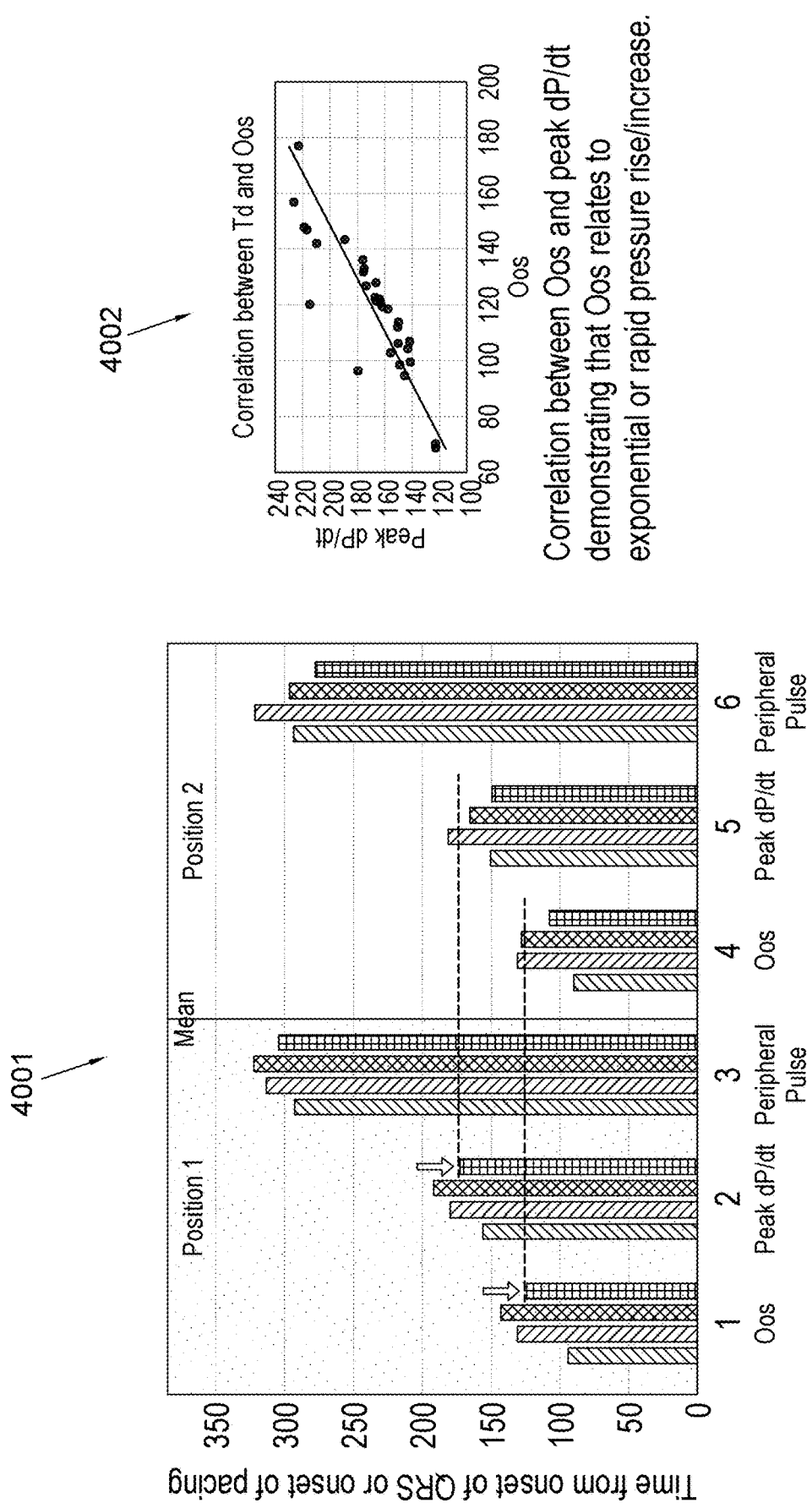
FIG. 31 shows the comparative shortening of onset of synergy and time to peak dP/dt with various kinds of pacing.

FIG. 31 shows two graphs, 4001 and 4002. Graph 4001 shows the shortening of OoS (measured as nadir of the BP filtered pressure curve) and Td (time to peak dP/dt, which is shown by the zero crossing of the bandpass filtered pressure curve) with various kinds of pacing in various positions. In this case, it may be said that the time to OoS is reduced further with pacing from position 2, and therefore it may be desirable to provide pacing from position 2. Graph 4002 shows the correlation between OoS and peak dP/dt, demonstrating that OoS relates to the peak exponential pressure rise within the heart, and as noted in FIG. 29, that the delay that result from a delayed onset of synergy is constant up to peak exponential pressure rise.

Summary of Onset of Synergy

Figure 32:
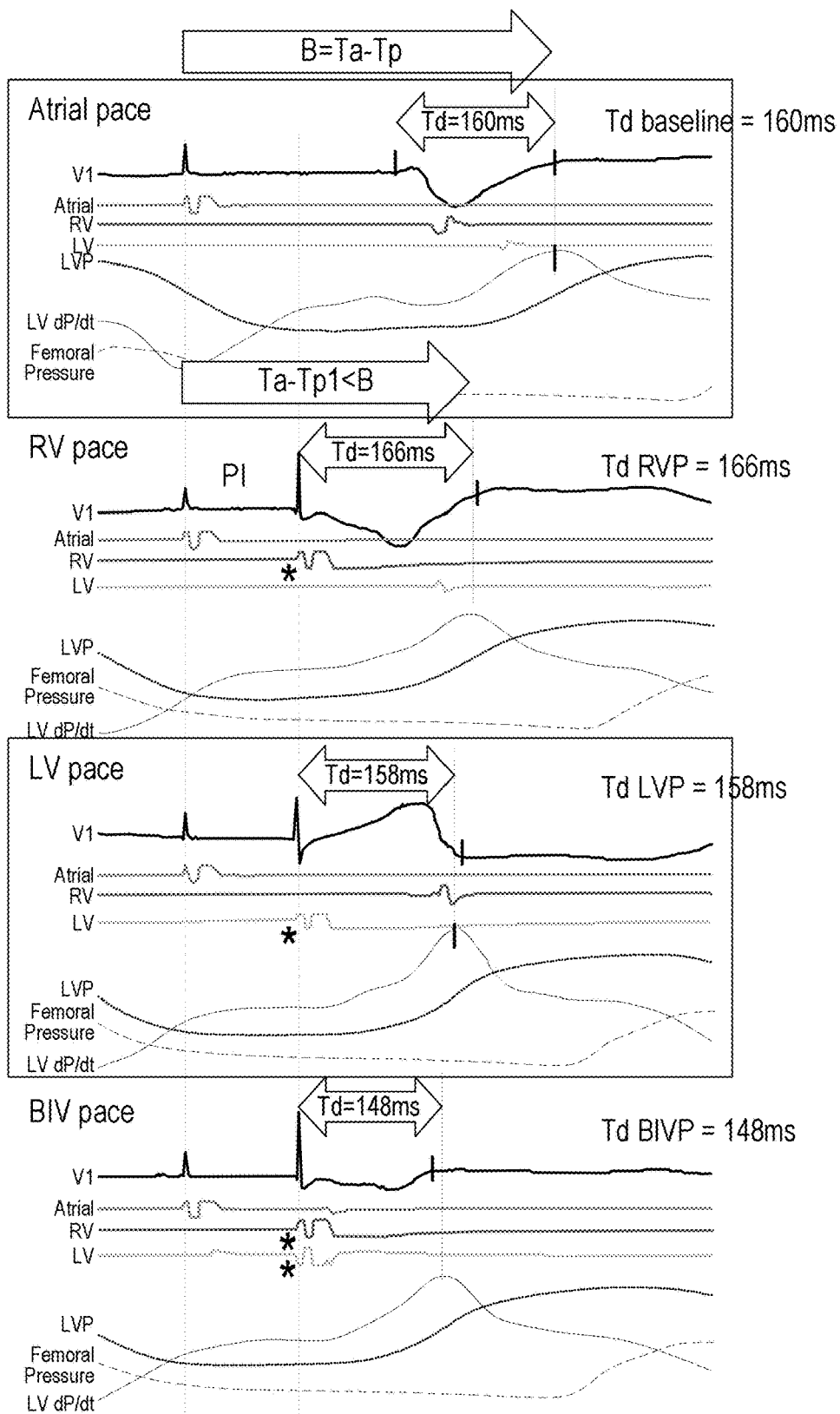
FIG. 32 shows a visual representation of an advancement of Td with various kinds of pacing.

Essentially, the inventor in this case has discovered a new measure that can be used to effectively identify patients that are suitable candidates for cardiac resynchronisation therapy, by measuring the point, termed onset of synergy (OoS), at which the myofibrils in the left heart chamber starts contracting isometrically and hence develop force rapidly which leads to an exponential pressure increase before ejection. OoS occurs within the pre-ejection interval, after the earliest mechanical activation and before aortic valve opening. OoS is therefore otherwise independent of the electromechanical coupling interval and the pre-ejection interval/isovolumic contraction period. By identifying how this point in time changes with therapy, it is possible to determine not only if a given therapy method would be effective in improving the prognosis of a patient, but also what would be the most effective therapy. A simple visual representation of an advancement of a measure that directly relates to the point of OoS, and how it varies with various kinds of pacing that may then be used to determine that BIVP would be the most effective treatment in this example may be seen in FIG. 32.

Whilst several methods are identified herein that allow for the point of OoS (or a similar point that directly relates to OoS) to be identified, such an identification requires unconventional data analysis steps that have been outlined herein to allow for detection, from which reliable conclusions can be reached. For example, the methods and systems described herein will only produce meaningful results under conditions were knowledge of the heart rate is known, knowledge of conduction through the AV node, knowledge of the time from stimulating the atrium either intrinsic or artificial to activation of the heart (whether intrinsic or artificial), or knowledge of the exact surface ECG configuration, so that if stimulation (intrinsic or artificial) is performed it can be recognized in the surface ECG or by VCG or electrical activation patterns of the heart.

Stimulation needs to be performed to avoid other activation than that from stimulation, calculated based on the knowledge above. For example, when stimulation from one electrode is performed, it should be tested that the stimulated heartbeat is that from stimulation and not that from intrinsic, as a combination of stimulations may lead to an inaccurate measurement of the time OoS, When a new electrode is stimulated, again it should be checked that the stimulated heartbeat is that from the stimulus only, and not from intrinsic, premature, preexcitation or other stimulation. Similar considerations are to be taken into account before stimulating two electrodes or more in combination. Measurements of OoS can only be made on beats where the measured responses result from the stimulated electrodes, and where the measured responses change when stimulation is removed.

When configurations (i.e. non-synergistic pacing from is performed and pacing of one or more electrodes) occur later than the earliest recognizable intrinsic activation of the heart, then this earliest activation should be used for reference rather than that resulting from the artificial stimulus.

By taking the above factors into account, not only when pacing the heart but also when analysing the sensed and measured data, it is possible to obtain knowledge of a potential electrode position and configuration that can be used to program an implantable pacemaker to provide synergistic stimulation of the heart.

Electrode Positioning Using Cardiac Parallelity

By measuring the degree of cardiac parallelity (i.e. the degree of parallel activation of the myocardium), it is possible to characterize cardiac synchronicity as well as identify anatomical pacing zones that result in more parallel activation of the myocardium to reduce cardiac dyssynchrony (resynchronization). Such a measure may be utilized to guide and optimize CRT.

Firstly, in order to measure the degree of cardiac parallelity, a recruitment curve is generated, showing the area of the heart that is recruited following pacing from an electrode against time. From such a graph, the degree of parallelity may be determined.

Figure 9:
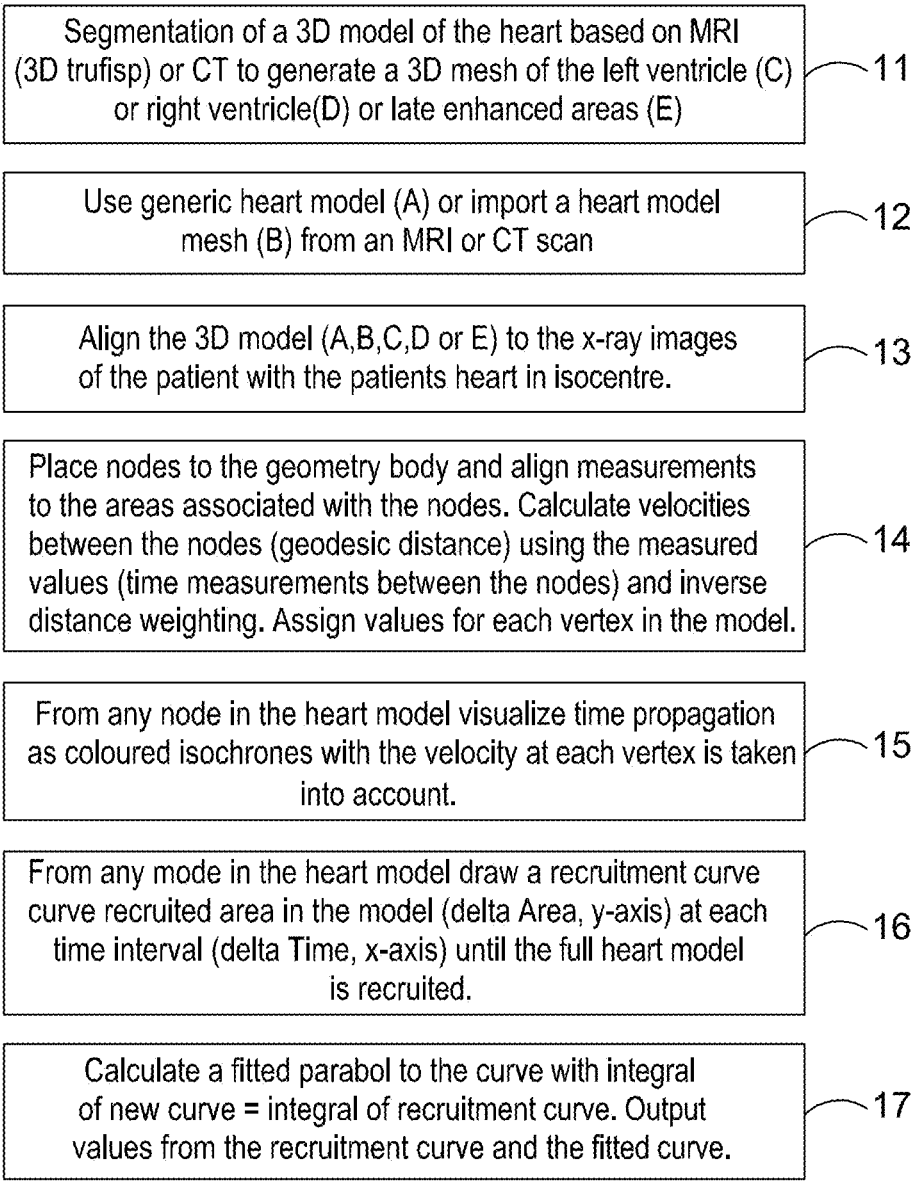
FIG. 9 shows a method for generating a 3D model of the heart including a 3D mesh of the ventricle.
Figure 10:
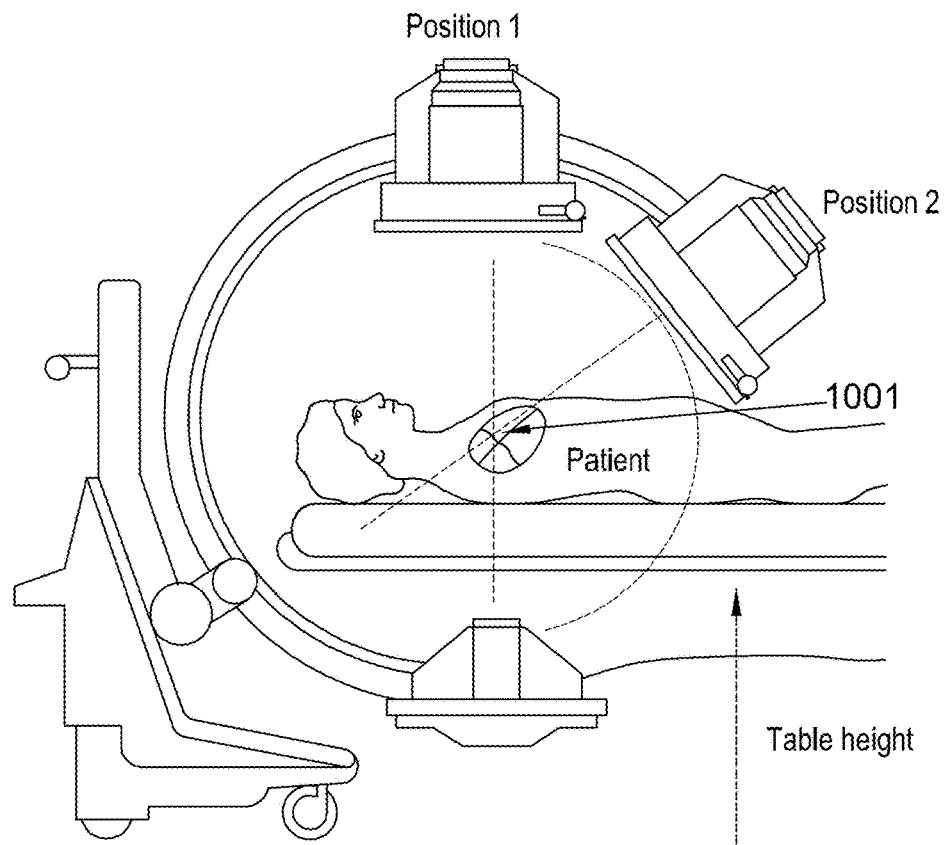
FIG. 10 illustrates the use of x-ray in relation to alignment of the 3D model with the patient's heart.
Figure 11:
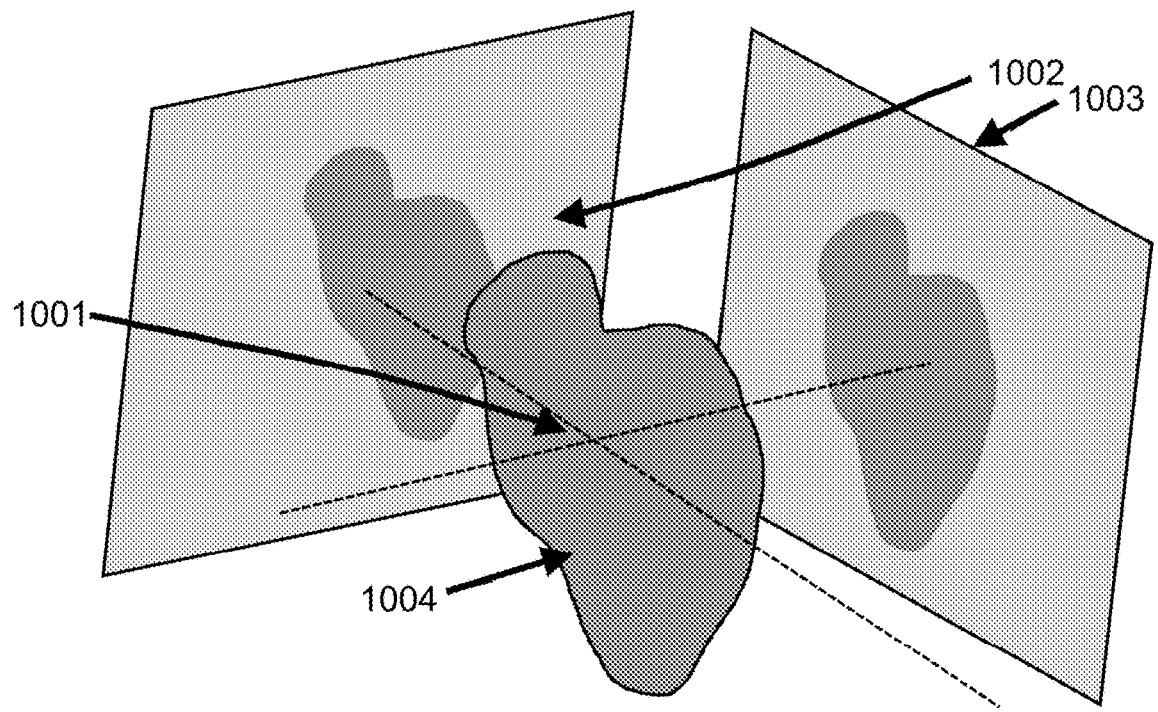
FIG. 11 shows x-ray images taken for use in the alignment of the 3D model.
Figure 12:
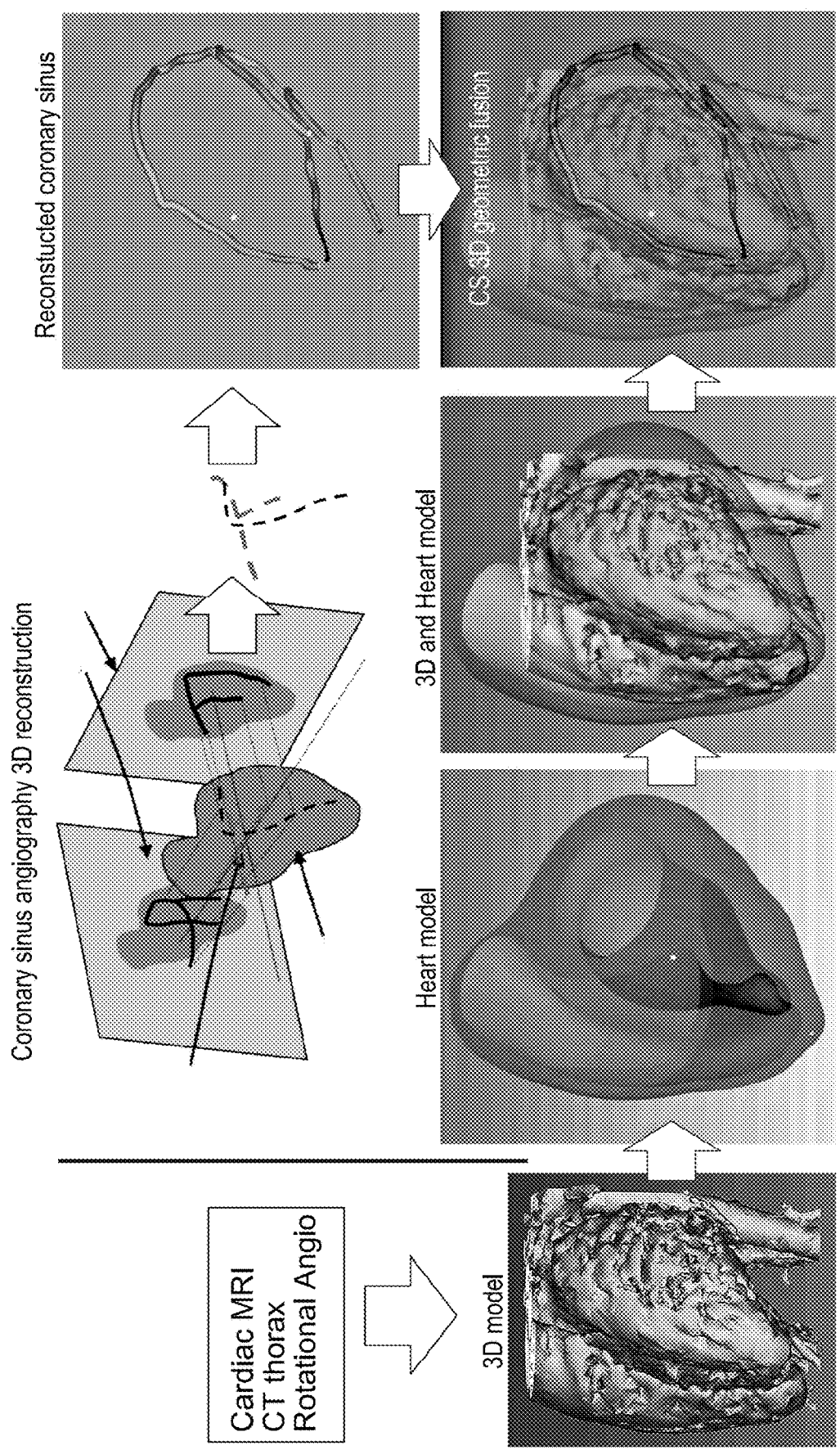
FIG. 12 shows reconstruction of the coronary sinus vein in 3D.

With reference to the method 10 of FIG. 9, a 3D model of the heart may be generated using medical images such as an MRI scan or a CT scan to generate a 3D mesh of the left ventricle, right ventricle and of late enhanced areas in step 11. Alternatively, the method may use a generic heart model, or a heart model mesh imported from a segmented CT/MRI scan, as in step 12. The 3D model of either steps 11 or 12 is then aligned to x-ray images of the patient, with the patient's heart at the isocenter 1001. One such method of aligning the 3D model with the heart of the patient may be seen in FIG. 10. At least two x-ray images 1001, 1002, as seen in FIG. 11, are taken at a known angle relative to each other, and are aligned relative to the fluoroscopy panels and to the isocenter 1001 in order to produce a 3D heart geometry 1004. Using the at least two x-ray images, the coronary sinus vein in 3D may be reconstructed as seen in FIG. 12. Using fluoroscopy panels and their known angles relative to each other with the patient's heart at the isocenter 1001, the coronary sinus vein may be reconstructed and overlaid over the 3D heart model of either steps 11 or 12.

Figure 13A:
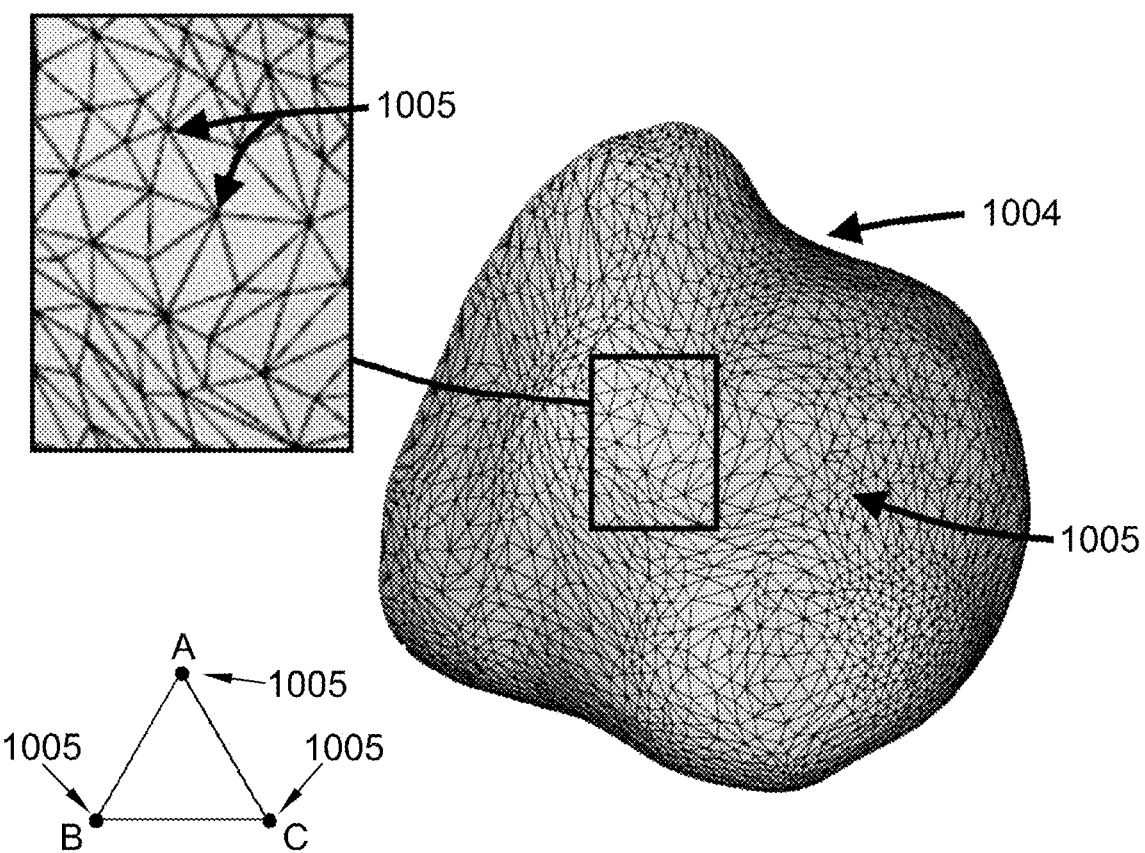
FIG. 13a illustrates a heart model converted to a geometric model.
Figure 13B:
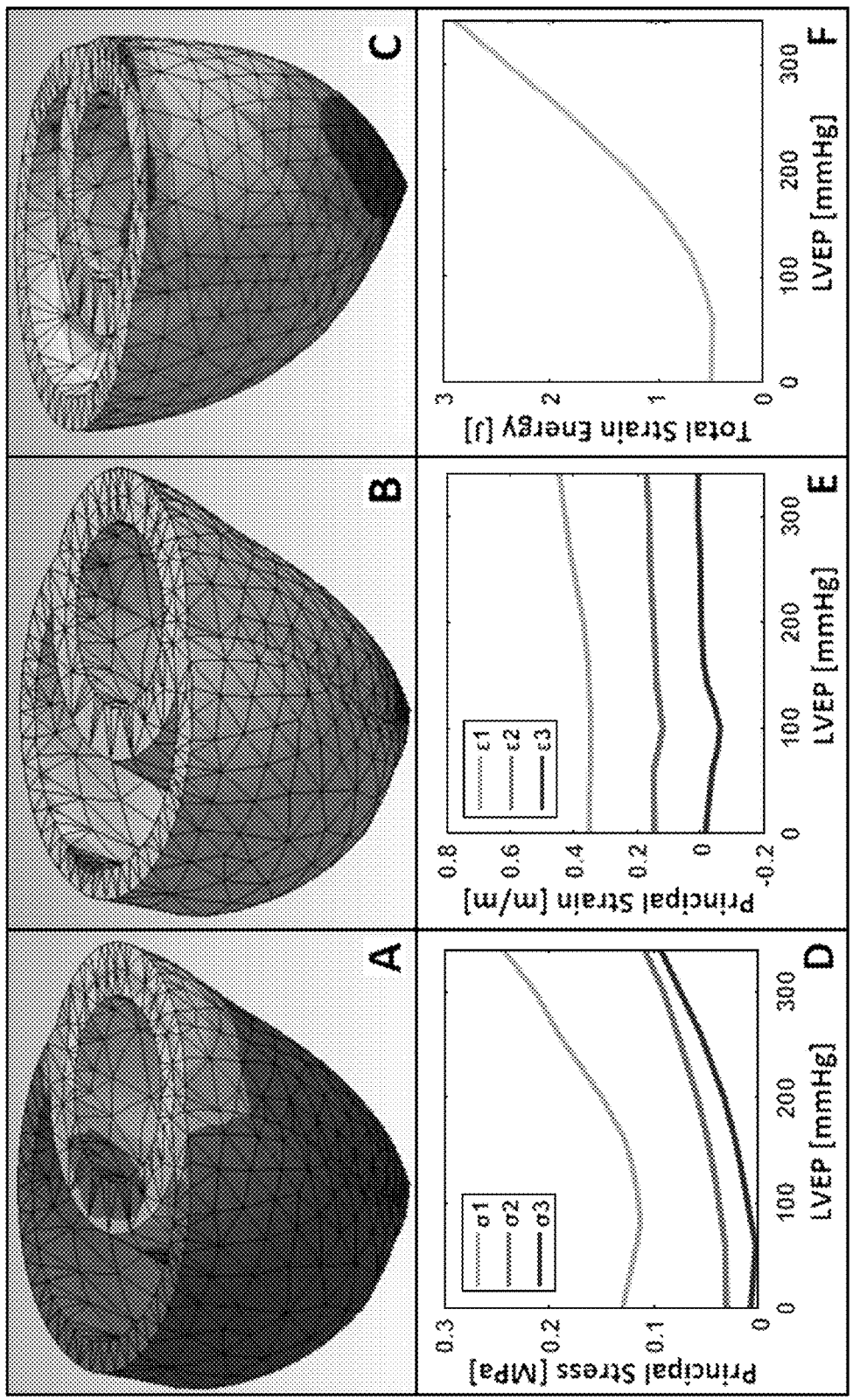
FIG. 13b illustrates another geometric heart model in 3D.

As can be seen in FIGS. 13a and 13b, the heart model 1004 (either a generic heart model or a specific heart model based on an MRI scan) may be converted into a geometric model consisting of multiple nodes (vertex) 1005 connected in a triangular network (vertices), representing a surface (FIG. 13a) or a volume (FIG. 13b). Electrodes 1006 may then be implanted into the heart, and during or after implantation additional nodes are marked on the geometry of the heart reflecting the positions of the implanted electrode. Between the nodes, intervals are input that reflect electrical intervals as measured by the electrodes in the patient when one of the electrodes are stimulated (paced). As will be understood by the skilled person, it is envisaged that the electrodes have already been implanted into the patient, and a heart model may then be updated to include nodes located at the points that the electrodes are located. A mathematical interpolation (e.g. inverse distance weighting) can be performed to assign values to the nodes between nodes with already measured values. In this way all nodes in the model will have values based on the measured values and the calculated ones to reflect electrical activation in the model. Calculation of electrical activation can be updated when new measurements are performed between electrodes, or modified with identification of areas of scar and/or fibrosis and/or other barriers to electrical propagation. The calculated values of all nodes is performed in such a way that electrical activation between all nodes in the model are at least partly explained.

The resulting geometry then contains multiple nodes with electrical time intervals measured between them and assigned to them. As the geodesic distance between all nodes may be calculated and calibrated, the geodesic propagation velocity of the electrical activation may then be calculated. The propagation velocity is then input to all existing nodes in the heart geometry (step 14).

Figure 14:
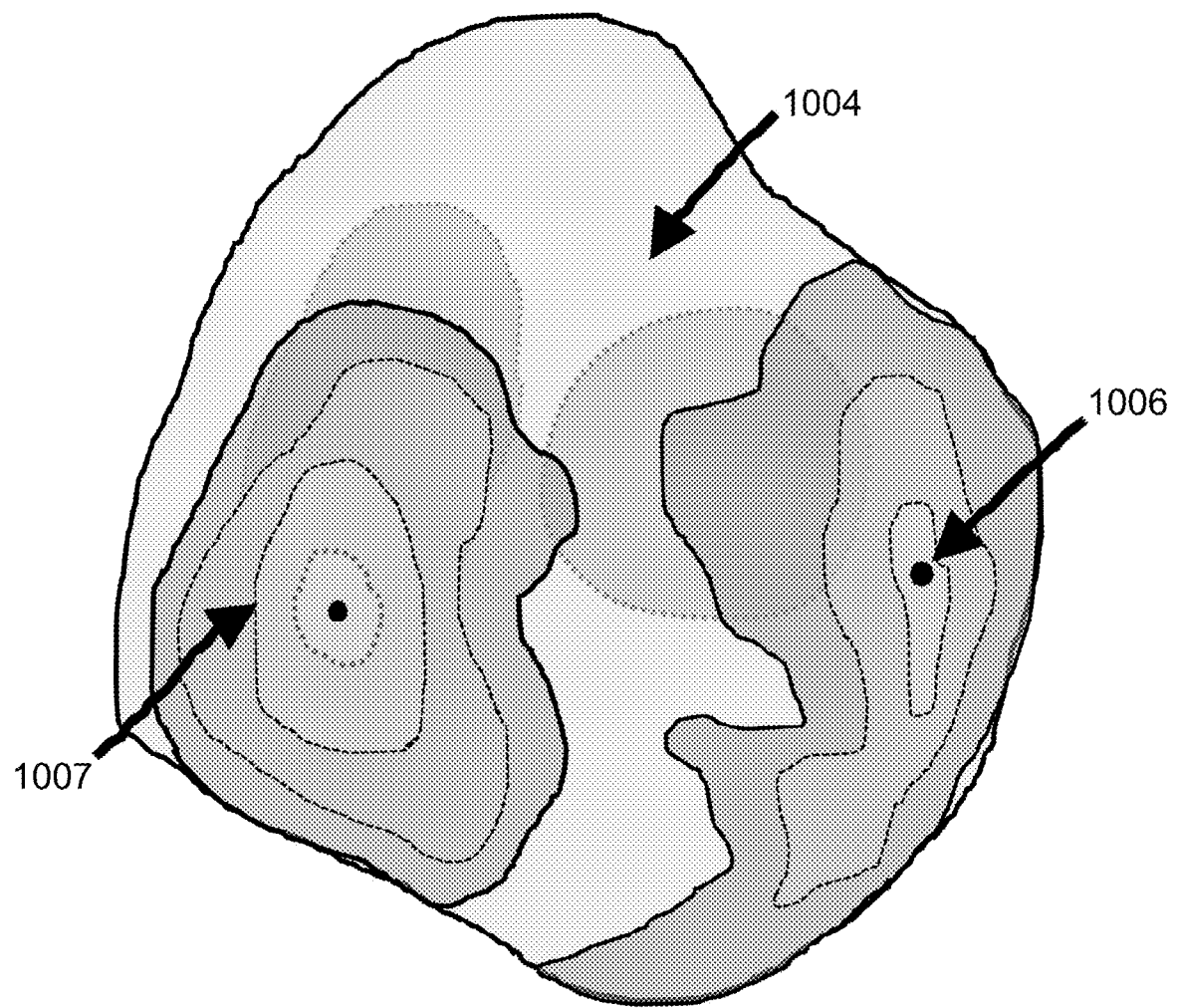
FIG. 14 is a visualization of time propagation of electrical activation.

In step 15, the propagation from multiple nodes or electrodes 1006 may then be calculated, resulting in a visualization of time propagation of electrical activation throughout the heart as coloured isochrones 1007, taking velocity at each vertex of the heart model mesh into account as can be seen in FIG. 14.

The geodesic distance between each node of the patient may be calculated. With reference to FIG. 15, an object 121 of a known size may be used on the fluoroscopy screen so as to calibrate the heart model for distance between vertices, which may then be represented and projected on the surface of the heart geometry as color zones and in a scale. In such a way, the heart geometry that is generated based on a generic heart model may be specifically tailored to each patient, with a known scale.

Figure 16:
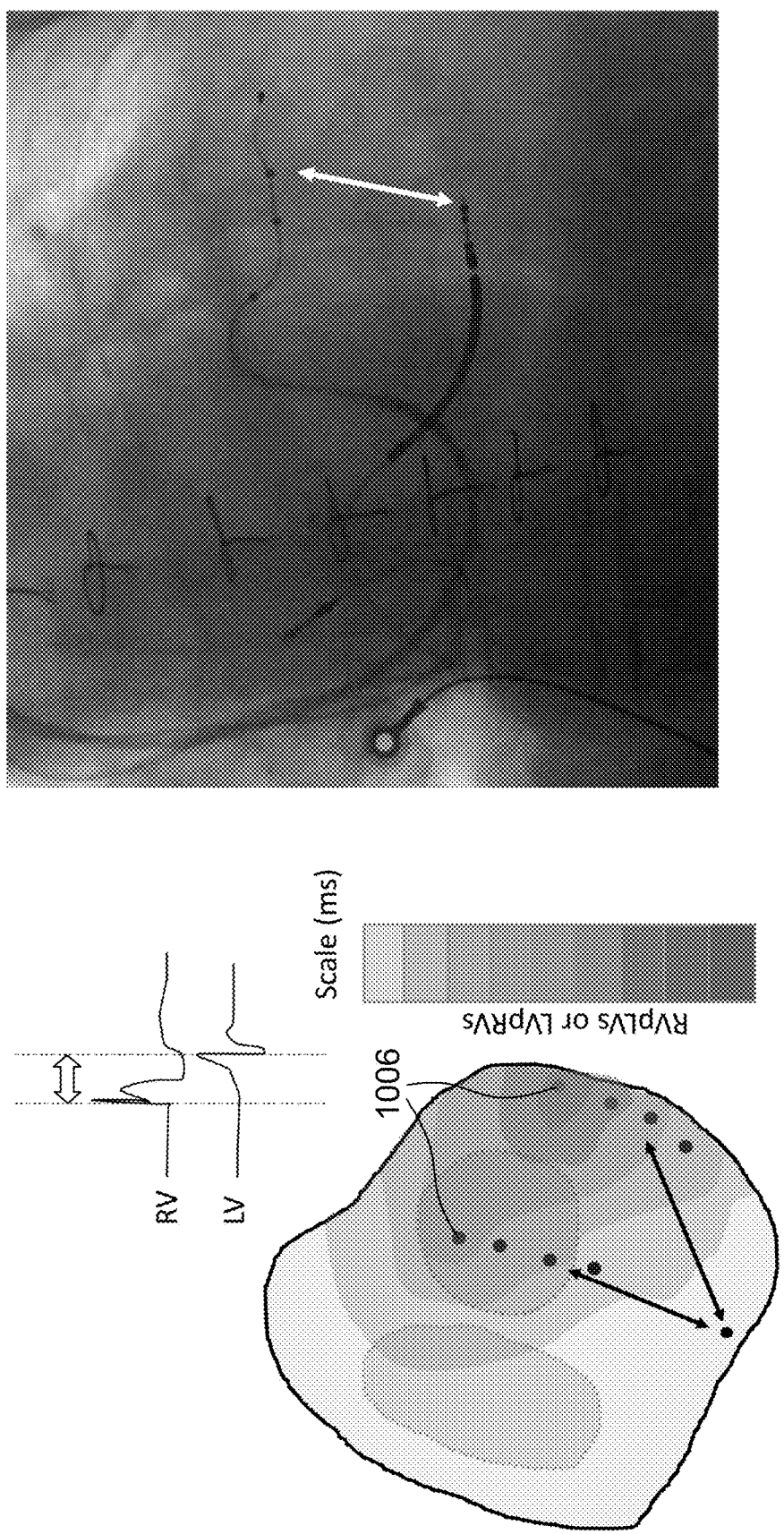
FIG. 16 illustrates pacing of the right ventricle in order to extrapolate measurements of recruited area of the heart.

As may be seen in FIG. 16, by pacing at one node 1006 and sensing in the other nodes, it is possible to extrapolate measurements of recruited area of the heart and represent such measurements as color zones/isochrones. For example, as seen in FIG. 16, the right ventricle may be paced. The time delay from the pacing and then the sensing (RVpLVs) at another electrode can be used to assign time measurements to the known vertices. By utilizing the known geodesic distances between the vertices, it is possible to extrapolate said measurements to the other vertices of the heart geometry and thereby produce isochrones of the additional recruited area at a given time point. Therefore, these isochrones are based on measurements acquired from the specific heart of a patient from the implanted electrodes and are projected onto the model or patient specific reconstruction of coronary sinus vein. This allows for a patient specific heart geometry for visualization of numbers and allows further calculations to be taken into account using already known values of vertices and any number of vertices in between.

A similar process may be performed using separation time, as seen in FIG. 17. In this case, the heart is not actively paced, rather isochrones are generated on the heart geometry based on the separation time (SepT), i.e. when the electrodes 1006 are activated due to the natural pacing of the heart.

Using a combination of one or more of the measurements described above, it is possible to build additional compound measures and present them on a geometric model of the heart of the patient.

Figure 18B:
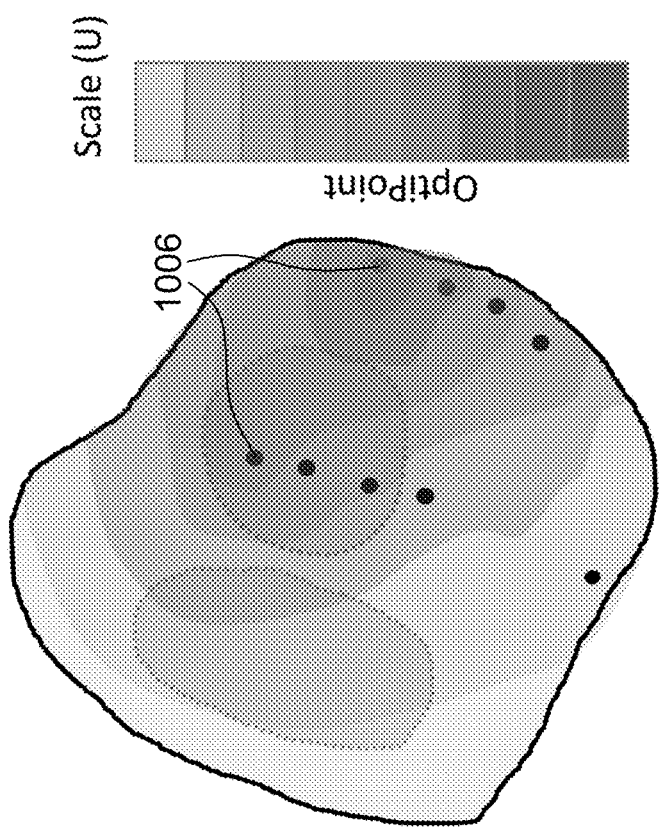
FIG. 18a shows a calculation of a compound measure, with FIG. 18b showing the addition of geodesic distance and highlighting of areas for potential electrode placement.
Figure 18A:
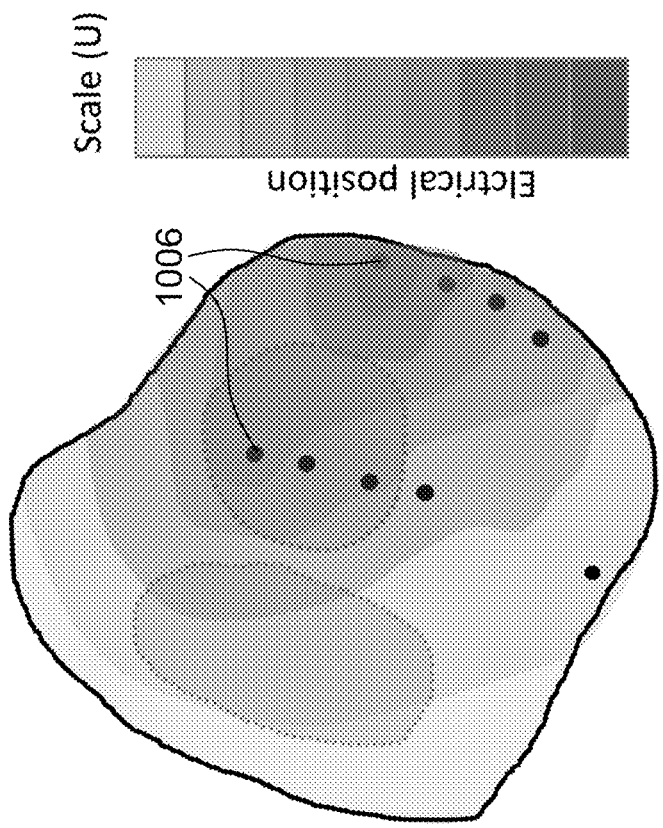

For example, as seen in FIG. 18a, a calculation based on SepT+RVpLVs may be calculated. Herein, such a measurement is termed "electrical position" and the calculation of this value provides different color representations of the heart model associated with certain regions of the heart (such as apical, anterior, lateral) for measurements obtained with the right ventricular electrode in the apex of the right ventricle.

By further adding geodesic distance, as in FIG. 18b, the optimal electrical and anatomical position may be considered. By such a measure, the result with the highest number on the scale representing a potential optimal (OptiPoint) position of an electrode. Such a position will represent the area most remote from present electrodes with the greatest effect. Such a placement of an electrode will achieve high parallelity when activated together with the right ventricular apical positioned electrode. Positions corresponding to the highest OptiPoint value are highlighted on a heart model, such as that of FIG. 18b, as being an area for potential electrode placement.

Figure 19:
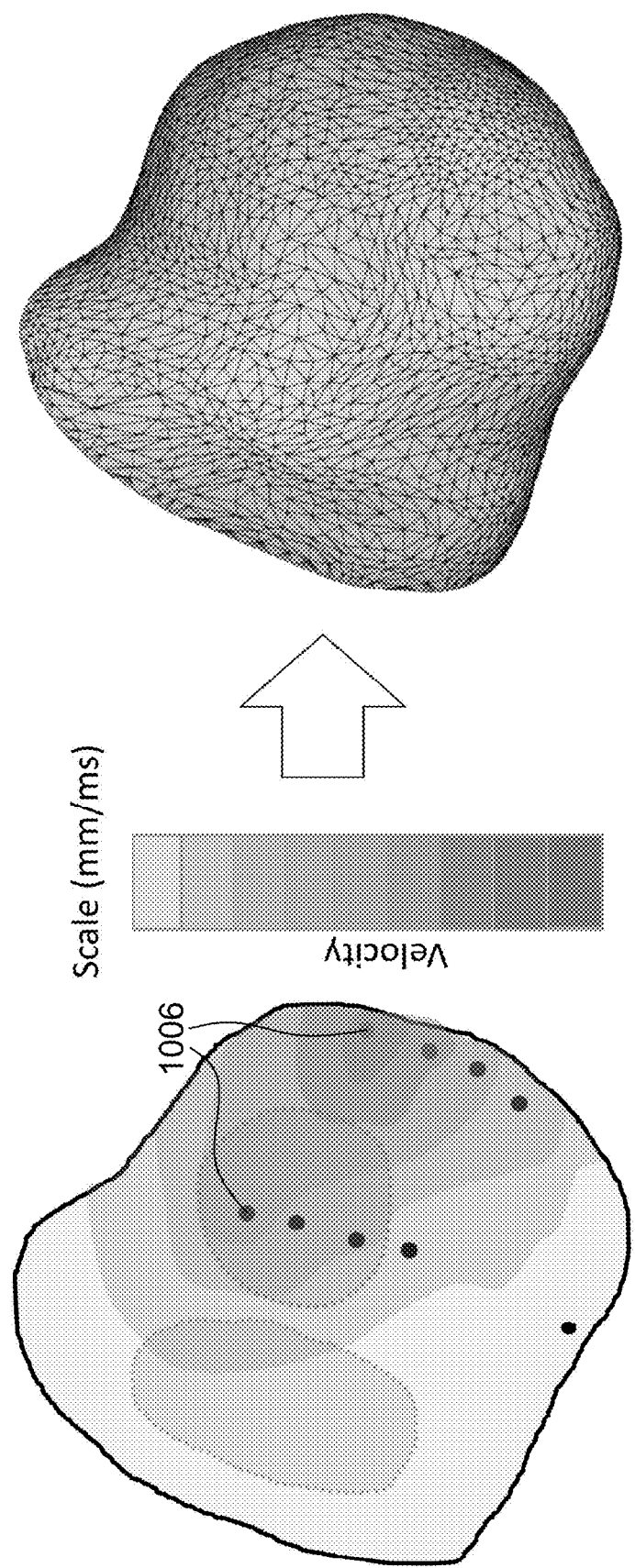
FIG. 19 shows an example of calculation of geodesic velocity.

As seen in FIG. 19, measurements of time intervals from pacing one electrode to sensing at another electrode, in combination with the geodesic distance between the electrodes allows for calculation of geodesic velocity. Such a geodesic velocity may provide input to an inverse weighted interpolation algorithm/calculation to provide velocity values to all vertices in the model. In this way, velocity values can be extrapolated to all remaining vertices with no nodes attached, which can then be indicative of characteristics of the heart tissue. For example, each vertex may be assigned a value for its specific velocity that has been calculated using an inverse distance weighted interpolation taking into account the geodesic distance between the target and source nodes, as well as the number of neighbouring vertices. These values can then be used to extrapolate velocity values to vertices with no nodes attached.

Figure 20:
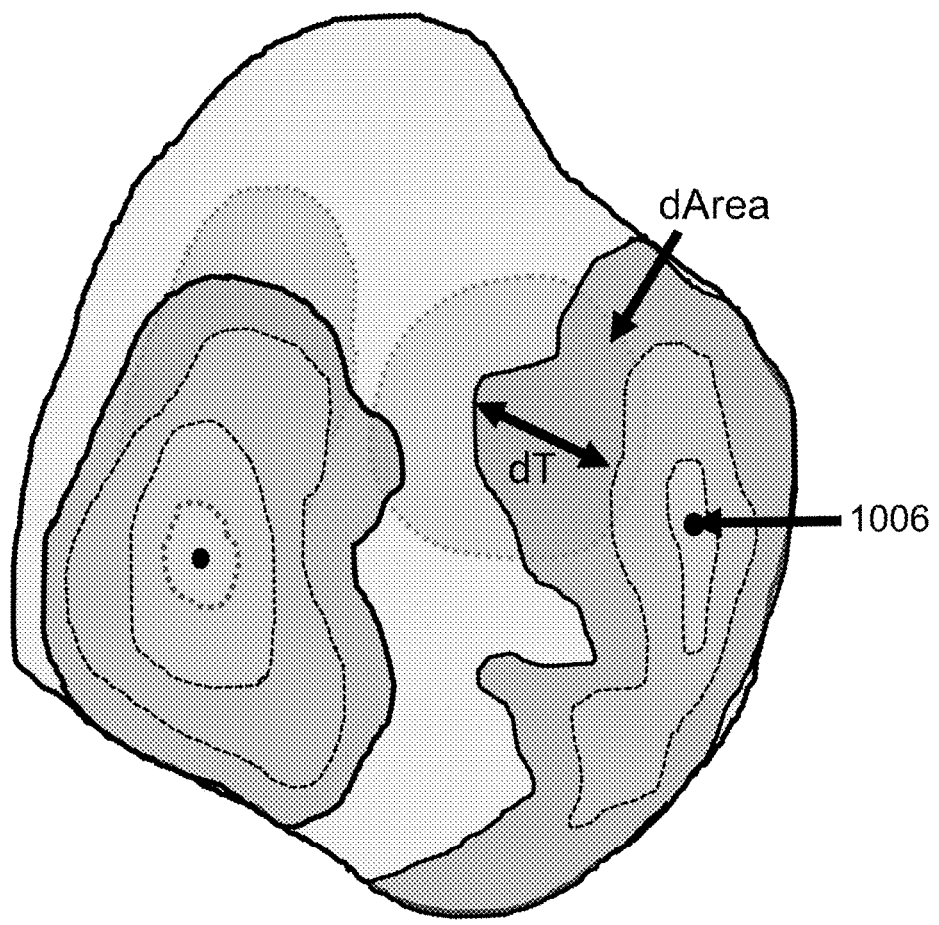
FIG. 20 is a heart model including a representation of propagation of electrical activation from the nodes.

When the velocity at each vertex has been interpolated as outlined above, the propagation of electrical activation from the nodes may be represented on a heart model, as seen in FIG. 20. This allows for the propagation of electrical activation to be visualized based on the tissue characteristics as isochrones on a color scale on the model of the heart. Such a time propagation may show a change in area over a change in time, and can be visualized from single, or multiple nodes 1006.

Figure 21:
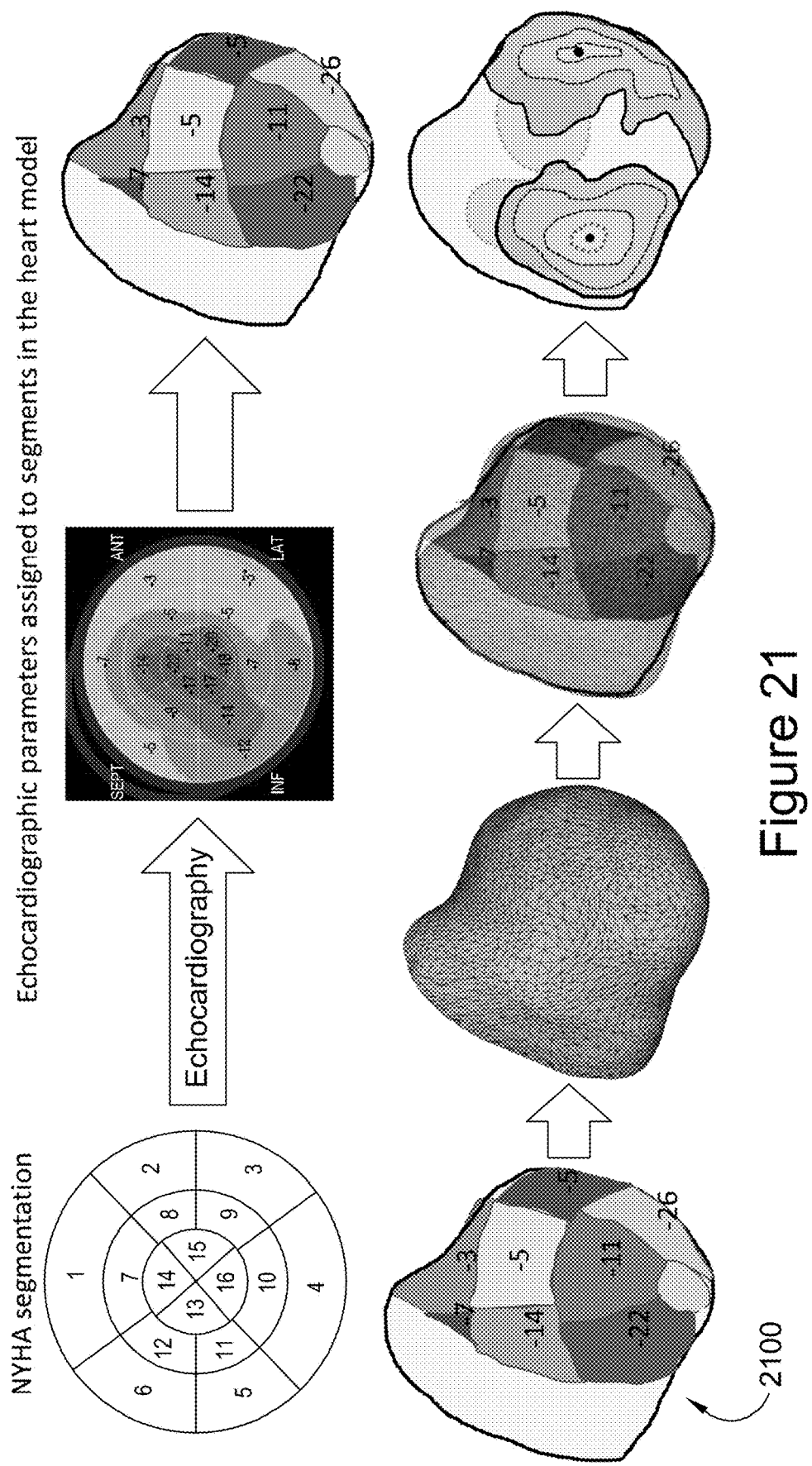
FIG. 21 shows echocardiographic parameters associated with the heart model.

Further, echocardiographic data using segmentation may be transferred onto the heart model, and be used to modify and enhance the tissue characteristics of the heart model. For example, as shown in FIG. 21, using American Heart Association (AHA) left ventricular segmentation model or similar, echocardiographic parameters may be assigned to segments in the heart model and transferred to the vertices of the heart geometry. Such an assignment can be applied on to the existing vertices of the existing heart model and be used therefore to further classify all of the nodes of the geometry, as seen in the flow chart 2100.

Figure 22:
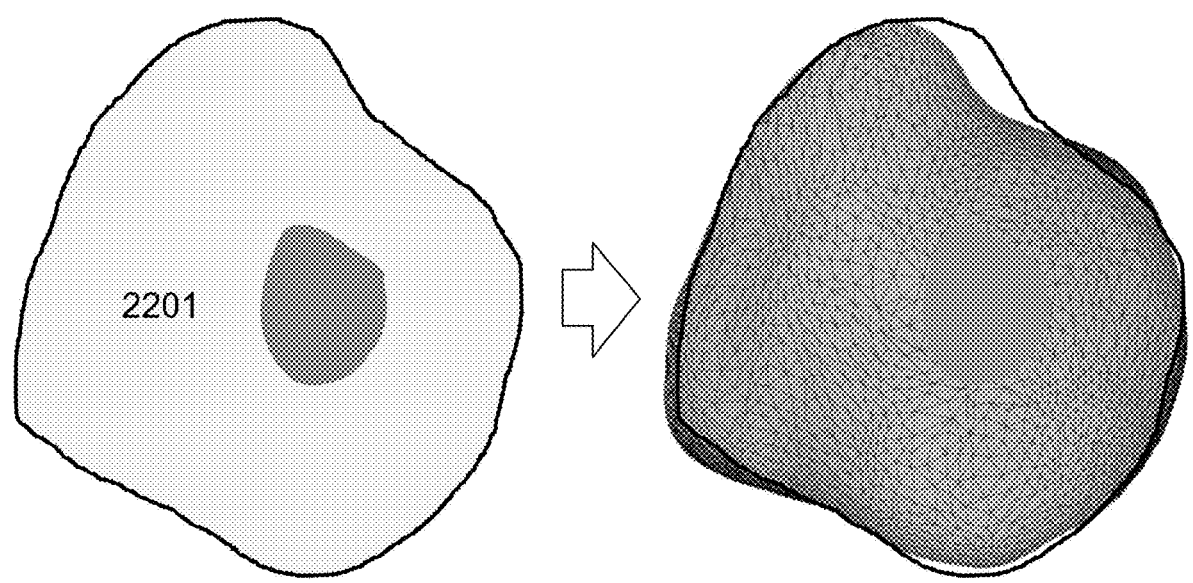
FIG. 22 visualizes tissue characteristics with reference to scar tissue.

Similarly, scar tissue 2201 of the heart muscle, such as that which may be identified by a 3D MRI scan may be used to assign tissue characteristics of the heart geometry. This is further visualized in FIG. 22, wherein the area of scar is projected onto the heart geometry, and each vertex is assigned a value for velocity, enhancing the tissue characteristics. Such classifications may be utilized to modify a velocity model and assign new velocity values to the vertices that have been identified with additional tissue characteristics.

Figure 23:
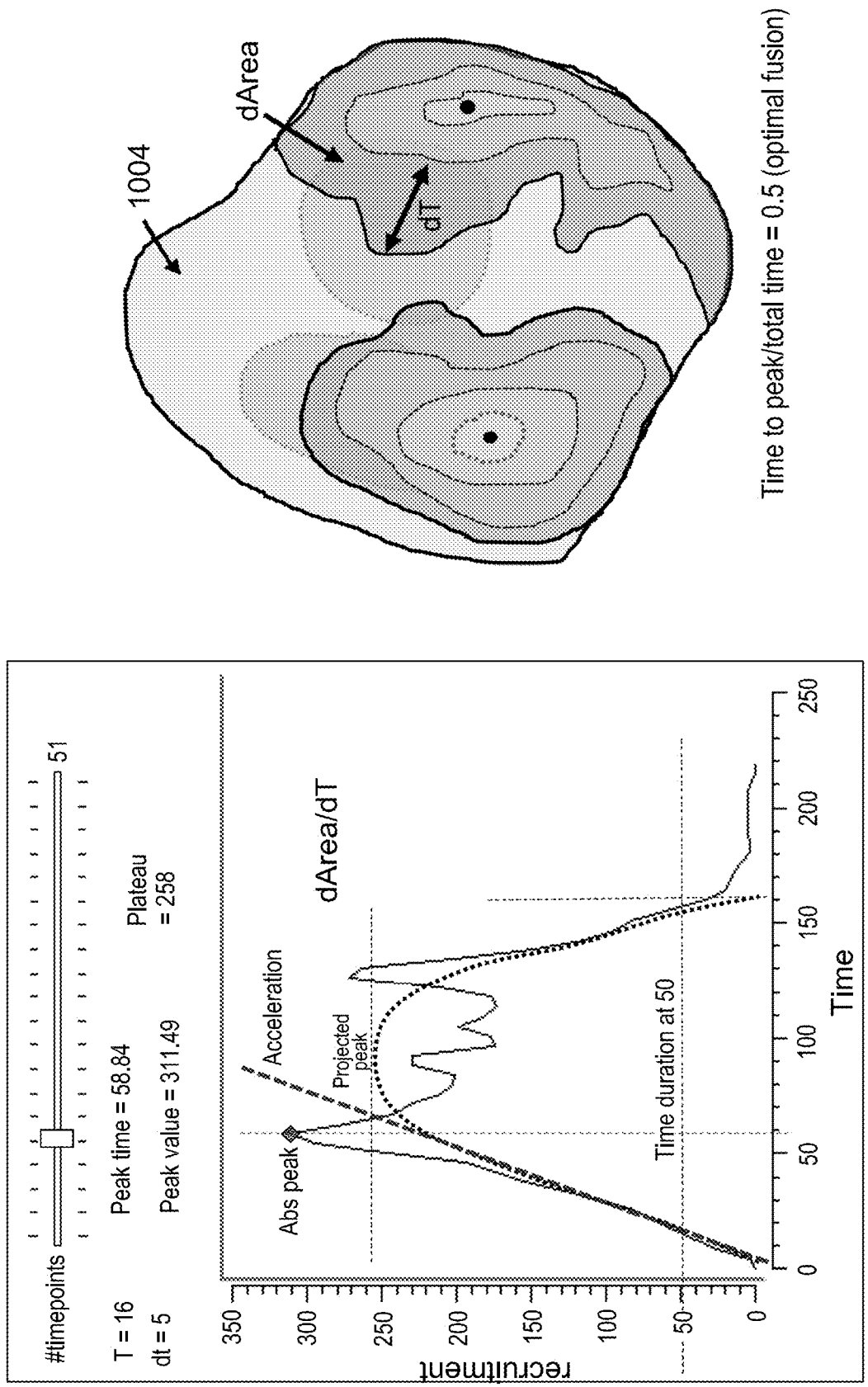
FIGS. 23 and 24 show recruitment curves representing the recruited area in the heart model.
Figure 24:
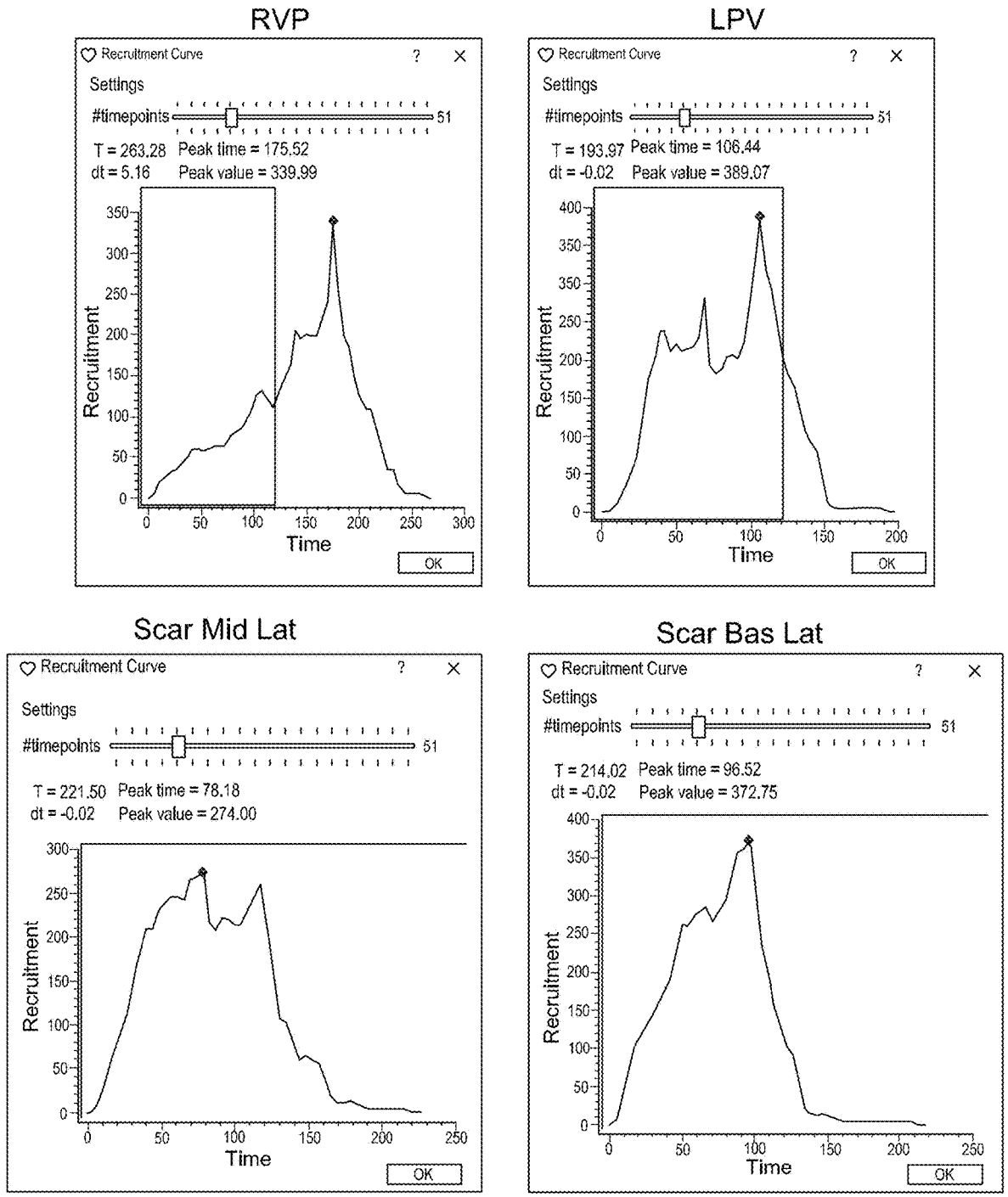
Figure 24:
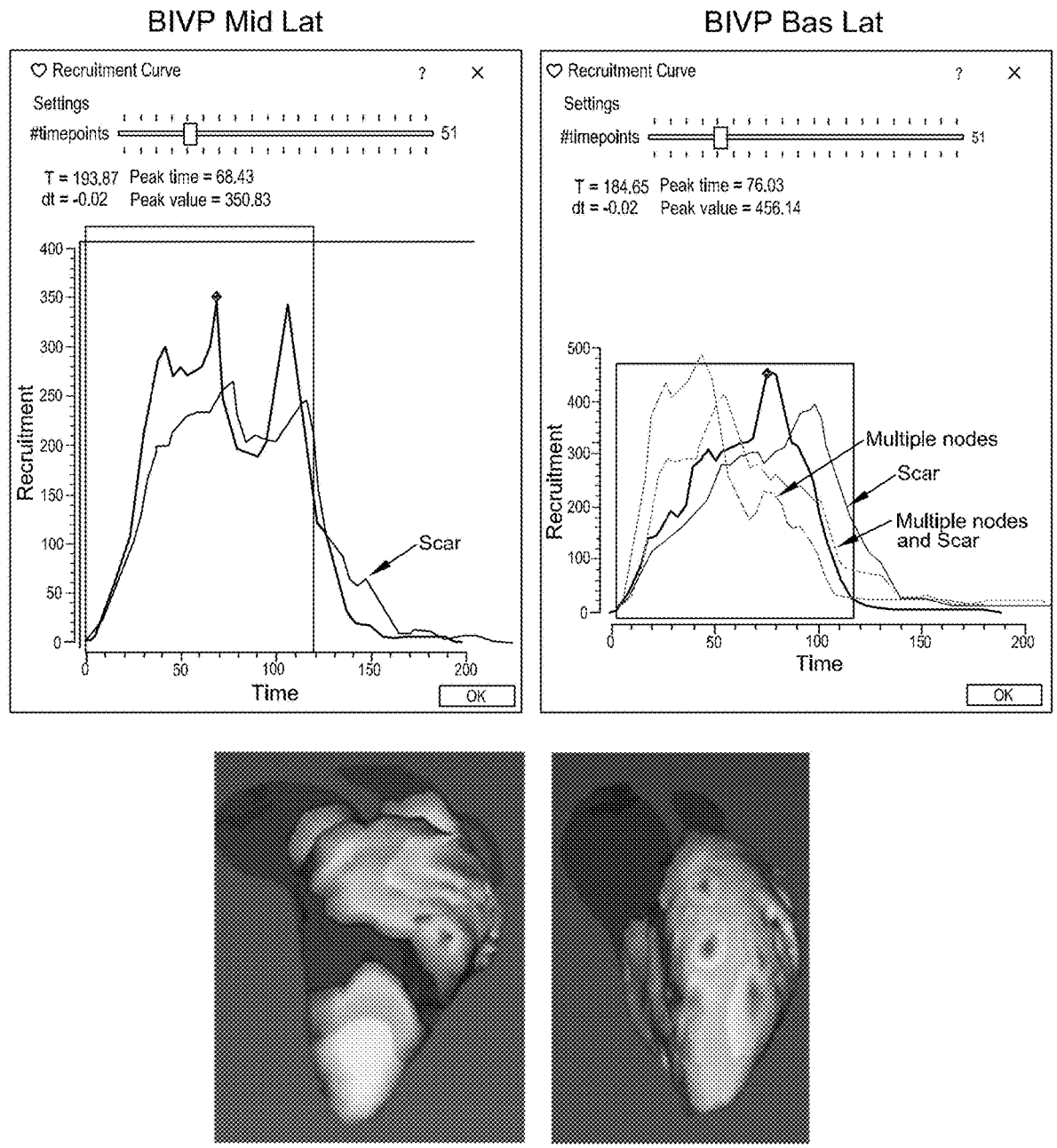

In step 16, the additional recruited area (of activated sarcomeres) at each point in time from the calculated velocity models can be calculated from multiple electrodes and the recruitment curve for said electrode(s) can be drawn based on the time propagation in the heart model when considering the added area at each time step until the full area, or a limited area, of the model is covered in isochrones, and their propagation from time=0 to time=x+1, as can be seen in FIGS. 23 and 24. In other words, the recruitment curve represents the recruited area or volume in the heart model with a measure of the change of area or volume of recruitment on the y-axis, and a scale of time on the x-axis. The recruitment curves can be characterised by multiple features, for example, the duration, slope, peak, mathematical expression, template matching.

Given the recruitment curve for a given node, a parabola may be fitted to the recruitment curve as can be seen in FIG. 23 and as described in step 17. The acceleration, peak and time to peak values of the propagation velocity can thereby be extracted from each recruitment curve, as well as the time to full recruitment (i.e. the time until the full heart model is recruited). More parallelity can be seen with a shorter time to peak propagation velocity, and thereby more propagation acceleration, as well as a larger peak value and a shorter time to full recruitment. Optimal curve characteristics can be provided, such that the peak recruitments should occur preferentially at 50% of the total recruitment time. The electrodes that create more parallelity (i.e. the greatest amount of total area of activation when the activation fronts meet) are chosen.

As can be seen in FIG. 24, the propagation curves may change with a change in electrode location and with the presence of scar. A number of recruitment curves are shown, and how each one varies is displayed for comparison. Based on such a comparison, the electrodes that result in the most ideal response may be chosen for pacing.

If the sensed activation pattern indicates too slow propagation through the tissue, the geodesic velocity is below a threshold, or the inability to provide sufficient parallel activation in the presence of scar tissue, the implantation of a CRT device should not take place, as such symptoms are not representative of dyssynchrony that may benefit from resynchronization therapy.

With pacing from each of the electrodes, a vectorcardiogram (VCG) recording the magnitude and the direction of the electrical forces that are generated during pacing of the heart is created. For each position that is tested, pacing is performed at each electrode, as well as for the two electrodes in combination, and a VCG is created for each situation. As seen in the example of FIG. 25b, a VCG RVp may be created for an electrode performing right ventricular pacing (RVp), and a VCG LVp may be created for an electrode performing left ventricular pacing (LVp). A synthetic VCG LVP+RVp may then be calculated from the sum of two of the created VCGs, and the real VCG is obtained when biventricular pacing is performed from the electrodes in combination, and collecting the resulting VCG BIVp.

Figure 25A:
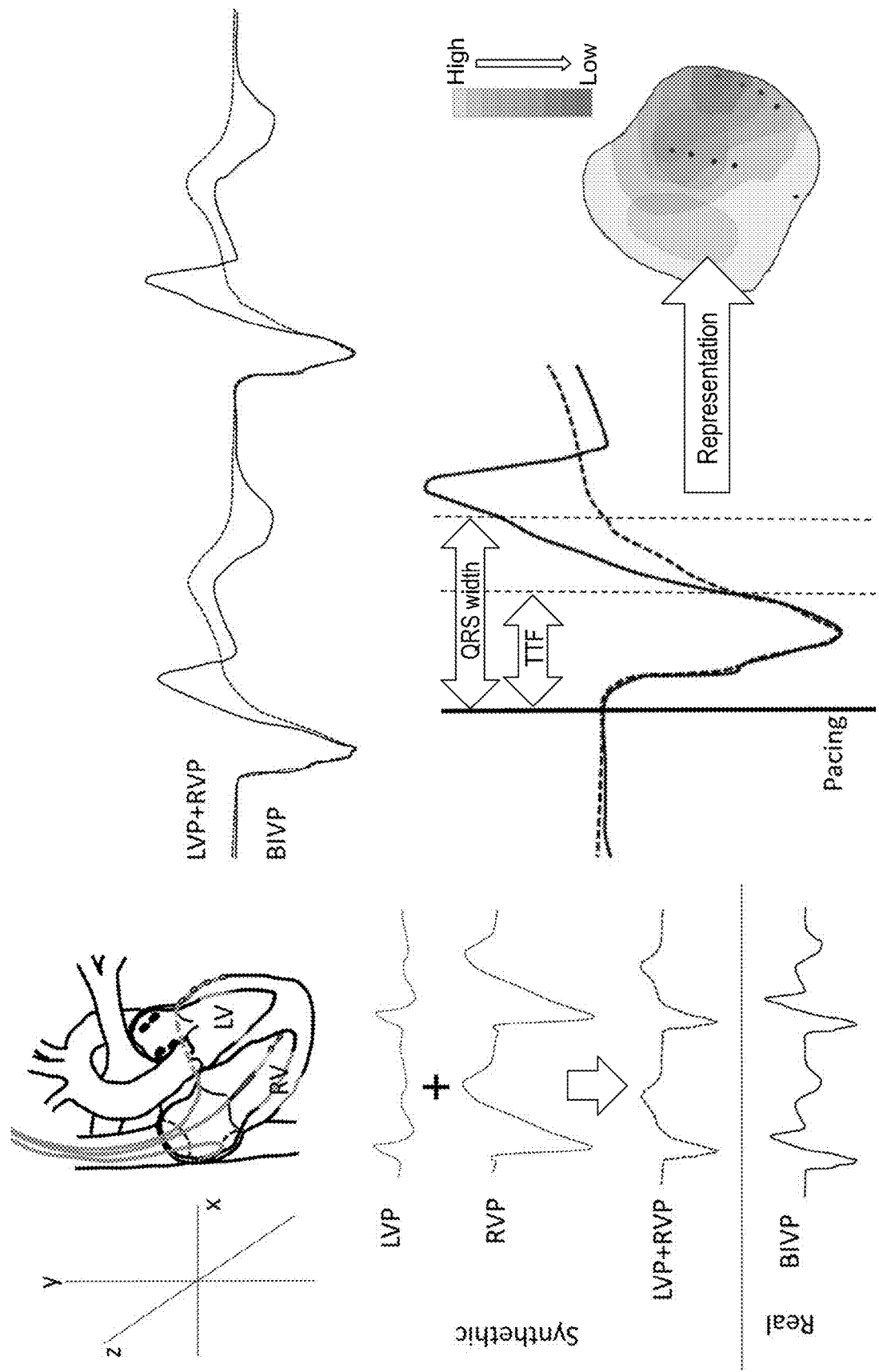
FIG. 25a shows a vectorcardiogram (VCG) created for an electrode performing right ventricular pacing (RVp)
Figure 25B:
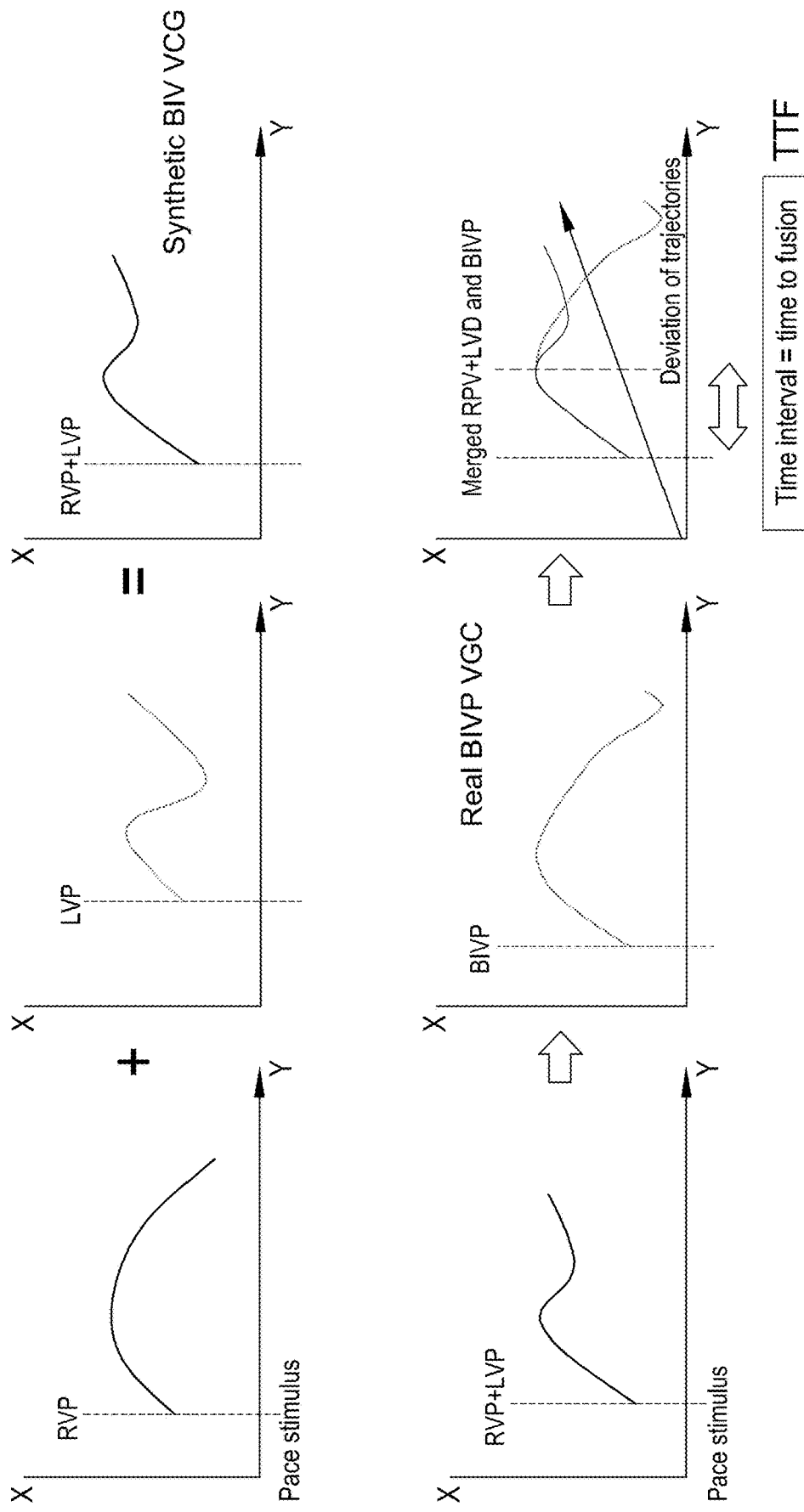
FIG. 25b illustrates a comparison of synthetic VCG LVP+RVp and the real VCG BiVp.

The synthetic VCG LVP+RVp and the real VCG BIVp are then compared, as seen in FIG. 25a, and the point in time of deviation of the curve trajectories from each other is noted and the interval from onset of pacing to the point in time is calculated as a time to fusion time interval. Whilst the examples shown in in FIG. 25b are displayed in 2D, it will be appreciated by the skilled person that the comparison may occur in 3D in order to improve accuracy.

The time interval between the pacing stimulus and the point of deviation of the curve trajectories represents the time to fusion (i.e. the time until the electrical propagation in cardiac tissue from multiple sites meet). The longer period of time until the point of deviation indicates more parallel activation of the myocardium. Therefore, the time to the point of deviation between the synthetic and the real VCG should be as long as possible. The time to fusion may be calculated in isolation, or relative to QRS width to determine the degree of synchronicity (parallel activation).

A similar method may be performed with electrograms (EGMs) and electrocardiograms (ECGs) in one or multiple dimensions. If adding an electrode stimulus site does not shorten the time interval to deviation of the curve trajectories, or if the time to deviation increases; an additional benefit of adding the electrode is seen, such that the electrode can be added to the stimulation site and number of electrodes.

The method allows analyzing the additional effect of adding one electrode and compare this new state of pacing an additional electrode to the state of not pacing this electrode. If the new electrode does not decrease time to fusion, this indicates that the addition of this electrode allows capture and activation of tissue without promoting fusion at an earlier stage than without. Thus, more parallel activation occurs when time to fusion does not decrease with adding an electrode.

Whilst the recruitment curves described above suggest positions for the electrodes, the generated VCGs may be further used to validate them. In this regard, VCGs and recruitment curves are measures of electrical activation that should reflect each other. When these measures are concordant, it gives validity to the suggested electrode positions and validity to the model. To this point, once good positions are found for the location of the electrode based on the generated recruitment curves, this position is then validated based on VCG. As would be appreciated by the skilled person, these measures are not necessarily only used in combination, rather each of the recruitment curves or determining the point of deviation may both be used individually to determine suitable electrode positions. Both of these measures reflect parallelity, the degree of parallel activation of the myocardium, and therefore may be utilized alone to identify anatomical pacing zones that result in more parallel activation of the myocardium to reduce cardiac dyssynchrony (resynchronization). Such a measure may be utilized to guide and optimize CRT.

An inverse solution ECG may also be utilized in addition, or as an alternative to using implanted electrodes to measure the degree of electrical activation. By utilizing data obtained from surface electrodes applied to patients, it is possible to extrapolate a map of electrical activation onto the heart model using an inverse solution approach, given that the heart model has been positioned in an anatomically correct position as described above and the relative electrode position to the heart model is correct and known.

In such a case, activation of each node in the heart geometry is seen relative to the distance from the first activated area, and therefore calculation of velocity can be performed for the model. This velocity can then be used to calculate recruitment curves. When pacing from a single electrode, the activation can be calculated, similar to the calculation of activation from a different electrode. These measurements can form the basis of propagation velocity calculations and recruitment curves.

In such a case, body surface electrodes are used to determine parallelity (i.e. the degree of parallel activation of the myocardium) by collecting surface potentials. Such surface potentials may then be extrapolated onto the heart model that has been aligned so as to be collocated with the actual location of the patient's heart, as previously described. Thereby, an inverse solution ECG activation map of the heart may be produced, and the activation map may be manipulated as described above in order to determine propagation velocity, and thereby the presence of dyssynchrony.

In order to obtain such an inverse solution ECG, a system may be provided with surface electrodes to acquire multiple surface biopotentials (ECG). The system may be configured such as to provide an inverse solution, in order to calculate electrical propagation on a segmented model of the heart, which can include scar tissue including scar. By utilizing the geodesic distance (from the heart model which is aligned with the patient's heart) in combination with the electrical propagation together, the system may be configured to calculate propagation velocity in the heart model based on the inverse solution electrical wavefront activation of the heart in combination with the geodesic distance. Once geodesic velocity is assigned to each vertex in the heart model, time propagation and parallelity can be measured from any and multiple sites in the model.

Further, the surface potentials may be incorporated in the cardiac model as a characteristic utilized to calculate propagation velocity from single or multiple points on the heart model. This, as described above with respect to measurements directly from electrodes implanted into the heart, allows for the generation of multiple propagation velocity curves in order to calculate the differences multiple different points. Using such a comparison between the multiple propagation velocity curves, it is possible to choose the ones having better acceleration, peak velocity or propagation time as an indication of the preferred location for placement of electrodes.

Example Method

The systems and methods described herein may be used both before and during treatment of patients with presumably dyssynchronous heart failure, with a resynchronization pacemaker (CRT) in order 1) identify the presence of an underlying substrate that identifies patients that are likely to respond positively (manifest resynchronization potential present) to and 2) identify optimal locations for placement of pacing leads/electrodes.

Patients are currently referred for implantation of a CRT pacemaker based on international guidelines that describe indication criteria. These criteria are based on inclusion criteria in larger clinical trials and, amongst other things, consists of symptoms of heart failure, reduced ejection fraction (heart function) and a widened QRS complex (preferably left bundle branch block) beyond 120-150 ms. However, currently only 50-70% of patients with one or more indications for treatment with a CRT actually respond to treatment. Reasons for these non-responders are multiple, but lead position, the underlying substrate (dyssynchrony), scar and fibrosis and electrode positions are the most prominent reasons. By improving the detection of the underlying substrate that indicates dyssynchronous heart failure, it is possible improve the selection of responders (in a diagnostic capacity) for optimization of treatment (allowing therapy to be personalized to the patient).

Firstly, it is desirable to detect and define the underlying substrate (resynchronization potential) that defines whether a patient will respond to CRT, and whether the substrate is present or not in patients with standard inclusion criteria. When the substrate is present, one should proceed implantation of a CRT pacemaker, but when the substrate is not present one should follow other guidelines that apply.

When underlying substrate is present, or even if the underlying substrate has not yet been identified, an optimal position for the leads may be found, based on measures of parallelity, which takes scar and fibrosis into account. The measurement of parallelity is performed with guidewires or leads with electrodes inside the heart (for example, in veins or chambers of the heart). Optimal positions are for the placement of the electrodes is then suggested.

When the leads are in optimal position, according to the determined optimal position taking into account the measured parallelity from each node, it is then possible to confirm the response (by either direct or indirect measurements of onset of myocardial synergy), or alternatively reject the position.

If the desired response is confirmed, then a CRT pacemaker should be implanted. If the response is not confirmed, the mapping and measurements of parallelity should be refined before final confirmation. If response is not able to be confirmed, the implantation should be abandoned and known guidelines should be followed for alternative implantations.

It is envisaged that all of the methods and systems described herein may be used together, or equally may be used separately. In this regard, it is possible to detect the presence dyssynchrony and resynchronization potential, and confirm resynchronization without selecting the optimal lead position, and equally, it is possible to select optimal lead position without confirming underlying substrate and resynchronization.

Therefore, a system may be provided that includes connection to electrodes that allow visualization of signals from the patient and measurements time intervals. Alternatively or additionally, a system may also be provided that includes sensors and electrodes and allows visualization of a heart model and calculations based on the heart model's geometry. Both of the above systems can be combined in the operating room.

An implementation of the above systems and methods will be further described herein by way of an example implementation during surgery.

A patient is firstly taken in to the operating room and sensors and electrodes are fixed on the patient's body surface.

In order to determine the delay to onset of myocardial synergy (OoS), one or more additional sensors may be utilized. For example, one or more of a pressure sensor, piezo-resistive sensor, fibreoptic sensors, an accelerometer, an ultrasound and a microphone may be utilized. Measurements from the additional sensors may be taken in real-time and be processed on location. If the delay to onset of myocardial synergy is short relative to the QRS complex or short in absolute values (for example either shorter than 120 ms or less than 80% of the QRS duration), then the implantation of a CRT device should not occur. When the delay to onset of myocardial synergy is measured to be long compared to the QRS complex or long in absolute values (for example either longer than 120 ms or longer than 80% of the QRS duration), then implantation of the CRT device should occur.

Body surface electrodes are used to determine parallelity (the degree of parallel activation of the myocardium) by collecting surface potentials for an inverse solution ECG activation map of the heart as described above to determine propagation velocity, and thereby the presence of dyssynchrony. Additionally or alternatively, electrodes implanted within the patient's heart may also be used to produce electrical activation maps, and thereby determine the presence of dyssynchrony. If the sensed activation pattern indicates too slow propagation through the tissue, or the inability to provide sufficient parallel activation in the presence of scar tissue, the implantation of a CRT device should not take place.

The patient is then prepared for surgery and sterile draped. Surgery is started as usual and leads are placed in the patient's heart through a skin incision below the left clavicle and puncture of the subclavian vein. The leads are then moved into position in the right atrium and right ventricle.

Dyssynchrony may then be introduced by pacing the right ventricle, and can be confirmed when measuring the delay of myocardial synergy as discussed above. A sensor may be placed in the left heart chamber, or in the right heart chamber, in order to determine the delay of onset of myocardial synergy. In this way, the same calculation may be performed as previously utilized in order to calculate the delay to onset of myocardial synergy.

Once the leads are in position, the coronary sinus is cannulated and an angiography in two planes are performed to visualize the coronary veins.

Once the coronary vein is visualized, cannulation can be performed with either a thin guide wire with an electrode at the tip, or any catheter with one or multiple electrodes for mapping purposes. Measurements of time intervals are then used to characterize one or more of the intrinsic activation, tissue properties and vein properties. The coronary anatomy is then reconstructed in software, and measurements are assigned to positions in the heart model relative to the reconstructed coronary sinus vein.

This data may then be used, in a method performed outside of the body, to calculate parallelity in order to highlight the electrode positions with the highest value of parallelity. Based on these measurements, the surgeon is advised to position the left ventricular (LV) lead with electrodes in a desired position/vein. Similar advice can be given also to reposition the right ventricular (RV) lead. Based on the acquired measurements and the processing thereof, advice can also be provided to include other and/or further electrodes to achieve a higher degree of parallelity. Other electrodes refer to other electrode positions than those available (endocardial, surgical access), and further electrodes refers to the use of multiple electrodes (more than two).

As a result of the above, the coronary vein branches are now seen in two planes and a suitable vein is selected for placement of a left ventricular lead.

When the LV electrodes are in position, the sensors may be used to determine the delay to onset of myocardial synergy, when pacing both the RV and the LV. Different electrodes may be analyzed by repositioning the LV lead at different positions. Measurements of the delay to myocardial synergy may occur using one or more of a pressure sensor, piezo-resistive sensor, fibreoptic sensor, an accelerometer, an ultrasound or by measured bioimpedance (when connected to the RV and LV leads). If the delay to myocardial synergy is not shortened, at least to less than for example 100% of the intrinsic measured value or when the bioimpedance measurements indicate by paradoxical movements that resynchronization is not taking place, the proposed lead positions should be abandoned. The intrinsic value measured from the QRS onset does not include the time from the onset of pacing to ventricular capture, and hence is by definition shorter than that measured from the stimulus. 110% would therefore approximate the time interval measured with intrinsic activation. In this way, the intrinsic delay to onset of synergy measured from the QRS complex can be calibrated by adding, for example, 15 ms to the value reflecting the time from pacing spike onset to electrical tissue capture that occur when artificially pacing.

When pacing the RV, the LV or both, a VCG can be reconstructed and the time to fusion can be calculated. The time to fusion may further be used in order to confirm the already measured parallelity. Surface electrodes can be used for inverse modelling to measure time to fusion. If the measured time to fusion, and the measured parallelity does not concur, the causes of such a discrepancy should be further reviewed.

It is possible that LV leads with multiple electrodes can be used on the discretion of the physician. The use of multiple electrodes can be used in measuring parallelity, and when found to increase parallelity, such an increase in parallelity can be confirmed using time to fusion, and by measuring the delay to onset of myocardial synergy.

Once the lead is in desired position, wherein the delay to onset of myocardial synergy is less than (for example) 110% of initial intrinsic value and less than (for example) 100% of the biventricularly paced QRS complex and, the CRT may be implanted and the device generator connected and implanted in a subcutaneous pocket. If the lead is found not to capture the myocardium or if the location is determined suboptimal based on scientific empiric data or measured intervals (QLV), the lead is repositioned and retested before the device generator is connected. The skin incision is then sutured and closed.

The systems described above may be embodied in an overall system that contains a signal amplifier or analogue digital converter (ECG, electrograms and sensor signals), a digital converter (sensor signals), processor (computer), software, connector to x-ray (either by direct communication with a dicom server or PACS server, or indirect with a framegrabber and an anglesensor). It is possible to use the system with different sensors at user discretion. Further, the system may also be used to solve other problems as well. For example, the systems may be utilized for identification of His region and placement of a pacing lead in the His bundle, with additional measurement of the delay to onset of myocardial synergy.

CLAUSES

1. A method of treating reversible cardiac dyssynchrony in a heart of a patient, the method comprising:
    determining a first onset of synergy by measuring a first time delay between a first reference time and a rapid increase in a pressure within a left ventricle of the heart;
    measuring a duration of electrical activation in the heart;
    determining the duration of electrical activation is longer than the first time delay;
    applying a pacing to the heart;
    determining a second onset of synergy after the pacing of the heart by measuring a second time delay between a second reference time and a rapid increase in the pressure within the left ventricle of the heart;
    determining the second time delay is shorter than the first time delay; and
    applying a treatment pacing to the heart according to a pacing rhythm based on the second onset of synergy, to treat a cardiac dyssynchrony in the patient.
2. The method of clause 1, wherein measuring the first time delay comprises: receiving data from one or more sensors indicative of an event relating to the rapid increase in a rate of pressure increase within the left ventricle identified in each contract of the heart;

identifying, at a first measured time, a characteristic response in the data received from the one or more sensors; and processing signals from the one or more sensors to determine the first time delay between the first measured time and the first reference time.

3. The method of clause 2, wherein measuring the second time delay comprises:

identifying, at a second measured time, with the one or more sensors and after the pacing of the heart, the characteristic response relating to the rapid increase in the rate of pressure increase within the left ventricle; and processing signals from the one or more sensors to determine the second time delay between the second measured time and the second reference time following the pacing.

4. The method of clause 3, further comprising:

applying modified pacing to the heart of the patient;

measuring a third time delay between the characteristic response following the modified pacing and a third reference time following the modified pacing by:

identifying, at a third measured time, with the one or more sensors and after the modified pacing of the heart, the characteristic response relating to the rapid increase in the rate of pressure increase within the left ventricle; and processing signals from the one or more sensors to determine the third time delay between the third measured time and the third reference time following the modified pacing;

identifying the modified pacing results in reversible and less dyssynchrony than the pacing by determining the third time delay is shorter than the second time delay; and applying the treatment pacing according to a pacing rhythm based on the third time delay.

5. The method of clause 2, wherein the characteristic response relating to the rapid increase in the rate of pressure increase within the left ventricle is a peak pressure rise in the time domain, trajectory advancement or delay compared to any trajectory in either the time derivative of a pressure curve trajectory or in the pressure curve trajectory itself.

6. The method of clause 2, wherein the characteristic response relating to the rapid increase in the rate of pressure increase within the left ventricle is the beginning of a pressure rise above the pressure floor in a pressure signal filtered above the first harmonic of the pressure signal.

7. The method of clause 2, wherein the characteristic response relating to the rapid increase in the rate of pressure increase within the left ventricle includes one of the onset of S-wave velocity, peak systolic acceleration (pSac), onset of S-wave strain rate, onset of global ejection, aortic valve opening, the onset of aortic flow, myocardial wall velocity, strain or any other measure to measure onset of synergy based on ultrasound measurements of the heart.

8. The method of clause 2, wherein the one or more sensors comprise an accelerometer, the method comprising:

receiving data from the accelerometer, which is within, or connected to the surface of, the patient; and determining the first reference time and the second reference time from a point of onset, offset, the full duration and/or a template match of the acceleration data.

9. The method of clause 2, wherein the one or more sensors comprise an accelerometer, a piezo-resistive sensor, a fiberoptic sensor, a sensor that senses vibrations, a sensor that senses pressure waves, an ultrasound sensor, or a magnetic sensor, or any combination thereof.

10. The method of clause 2, wherein the one or more sensors is configured to detect heart sounds corresponding to the identified characteristic response relating to the rapid increase in the rate of pressure increase within the left ventricle.

11. The method of clause 2, wherein the one or more sensors comprise a pressure sensor located in the left ventricle.

12. The method of clause 2, further comprising:

injecting current through surface skin electrodes;

measuring impedance between the electrodes; and producing a complex impedance waveform and an amplitude waveform, wherein the identified characteristic response relating to rapid increase in the rate of pressure increase within the left ventricle is the time at which the heart muscle shortens and blood is ejected from the heart, and wherein the time of the identified characteristic response relating to the rapid increase in the rate of pressure increase within the left ventricle is determined where the complex impedance and the amplitude waveform meet and deviate.

13. The method of clause 1, wherein measuring the duration of electrical activation in the heart comprises measuring biopotentials representing electrical activation of the heart.

14. The method of clause 13, wherein measuring biopotentials representing electrical activation of the heart further comprises:

measuring surface biopotentials of the patient to produce an electrocardiogram (ECG);

determining the reference time from a point of onset, offset or the full duration of a QRS signal measured from the ECG; and determining the duration of the QRS complex.

15. The method of clause 1, wherein determining the duration of electrical activation is longer than the first time delay comprises comparing the first time delay with the duration of electrical activation of the heart; and determining the first time delay is longer than a set fraction of electrical activation of the heart.

16. The method of clause 1, wherein the rapid increase of the rate of pressure change relates to the final peak in the second order derivative of the pressure within the left ventricle prior to opening of the aortic valve and/or maximum pressure.

17. The method of clause 1, wherein the first reference time and the second reference time relate to different marker points, wherein the step of comparing the first time delay and the second time delay further comprises:

compensating for a time delay between the first reference time and the second reference time.

18. The method of clause 1, wherein the treatment pacing comprises a number of electrodes and a placement of the electrodes based on the second onset of synergy.

19. The method of clause 18, wherein the number of electrodes and the placement of the electrodes is determined by:
  generating a 3D mesh of at least part of the heart from a 3D model of at least part of the heart of the patient, or using a generic 3D model of the heart to obtain a 3D mesh of at least a part of the heart, the 3D mesh of at least a part of the heart comprising a plurality of nodes;
  aligning the 3D mesh of at least part of a heart to images of the heart of the patient;
  placing additional nodes onto the 3d mesh corresponding to a location of at least two electrodes on the patient;
  calculating a propagation velocity of the electrical activation between the nodes of the 3D mesh corresponding to the location of the at least two electrodes;
  extrapolating the propagation velocity to all of the nodes of the 3D mesh;
  calculating a degree of parallel activation of the myocardium for each node of the 3D mesh; and
  determining the optimal electrode number and position on the heart of the patient based on the node(s) of the 3D mesh with a calculated degree of parallel activation of the myocardium above a predetermined threshold.
20. The method of clause 19, wherein determining the degree of parallel activation of a heart undergoing pacing, via a method comprising:
  calculating a vectorcadiogram, VCG, or electrocardiogram, ECG, waveforms from right ventricular pacing, RVp, and left ventricular pacing, LVp;
  generating a synthetic biventricular pacing, BIVP, waveform pacing by summing the VCG of the RVp and the LVp, or by summing the ECG of the RVp and the LVp;
  calculating a corresponding ECG or VCG waveform from real BIVP;
  comparing the synthetic BIVP waveform and the real BIVP waveform; and
  calculating time to fusion by determining the point in time in which the activation from RVp and LVp meets and the synthetic and the real BIVP curves start to deviate,
  wherein a delay in time to fusion indicates that a larger amount of tissue is activated before wave fronts for electrical activation meet, thereby indicating a higher degree of parallel activation.
21. The method of clause 1, wherein an AV-delay of the pacing is calculated so that AP-VP is shorter than the shortest of AP-RVs and AP-QRS.
22. The method of clause 21, wherein the AV-delay of the pacing is 0.7*(AP*RVs) or 0.8*(AP-QRS).

The invention claimed is:
1. A method of treating reversible cardiac dyssynchrony in a heart of a patient, the method comprising:
  determining a first onset of synergy by measuring a first time delay between a first reference time and a rapid increase in a pressure within a left ventricle of the heart;
  measuring a duration of electrical activation in the heart;
  determining the duration of electrical activation is longer than the first time delay;
  applying a pacing to the heart;
  determining a second onset of synergy after the pacing of the heart by measuring a second time delay between a second reference time and a rapid increase in the pressure within the left ventricle of the heart;
  determining the second time delay is shorter than the first time delay; and
  applying a treatment pacing to the heart according to a pacing rhythm based on the second onset of synergy, to treat a cardiac dyssynchrony in the patient.
2. The method of claim 1, wherein measuring the first time delay comprises:
  receiving data from one or more sensors indicative of an event relating to the rapid increase in a rate of pressure increase within the left ventricle identified in each contract of the heart;
  identifying, at a first measured time, a characteristic response in the data received from the one or more sensors; and
  processing signals from the one or more sensors to determine the first time delay between the first measured time and the first reference time.
3. The method of claim 2, wherein measuring the second time delay comprises:
  identifying, at a second measured time, with the one or more sensors and after the pacing of the heart, the characteristic response relating to the rapid increase in the rate of pressure increase within the left ventricle; and
  processing signals from the one or more sensors to determine the second time delay between the second measured time and the second reference time following the pacing.
4. The method of claim 3, further comprising:
  applying a modified treatment pacing to the heart of the patient;
  measuring a third time delay between the characteristic response following the modified pacing and a third reference time following the modified pacing by:
  identifying, at a third measured time, with the one or more sensors and after the modified pacing of the heart, the characteristic response relating to the rapid increase in the rate of pressure increase within the left ventricle; and
  processing signals from the one or more sensors to determine the third time delay between the third measured time and the third reference time following the modified pacing;
  identifying the modified pacing results in reversible and less dyssynchrony than the pacing by determining the third time delay is shorter than the second time delay; and
  applying the treatment pacing according to a pacing rhythm based on the third time delay.
5. The method of claim 2, wherein the characteristic response relating to the rapid increase in the rate of pressure increase within the left ventricle is a peak pressure rise in the time domain, trajectory advancement or delay compared to any trajectory in either the time derivative of a pressure curve trajectory or in the pressure curve trajectory itself.
6. The method of claim 2, wherein the characteristic response relating to the rapid increase in the rate of pressure increase within the left ventricle is the beginning of a pressure rise above the pressure floor in a pressure signal filtered above the first harmonic of the pressure signal.
7. The method of claim 2, wherein the characteristic response relating to the rapid increase in the rate of pressure increase within the left ventricle includes one of the onset of S-wave velocity, peak systolic acceleration (pSac), onset of S-wave strain rate, onset of global ejection, aortic valve opening, the onset of aortic flow, myocardial wall velocity, strain or any other measure to measure onset of synergy based on ultrasound measurements of the heart.

8. The method of claim 2, wherein the one or more sensors comprise an accelerometer, the method comprising:
receiving data from the accelerometer, which is within, connected to the surface of, the patient; and
determining the first reference time and the second reference time from a point of onset, offset, the full duration and/or a template match of the acceleration data.

9. The method of claim 2, wherein the one or more sensors comprise an accelerometer, a piezo-resistive sensor, a fiberoptic sensor, a sensor that senses vibrations, a sensor that senses pressure waves, an ultrasound sensor, or a magnetic sensor, or any combination thereof.

10. The method of claim 2, wherein the one or more sensors is configured to detect heart sounds corresponding to the identified characteristic response relating to the rapid increase in the rate of pressure increase within the left ventricle.

11. The method of claim 2, wherein the one or more sensors comprise a pressure sensor located in the left ventricle.

12. The method of claim 2, further comprising:
injecting current through surface skin electrodes;
measuring impedance between the electrodes; and
producing a complex impedance waveform and an amplitude waveform,
wherein the identified characteristic response relating to rapid increase in the rate of pressure increase within the left ventricle is the time at which the heart muscle shortens and blood is ejected from the heart, and wherein the time of the identified characteristic response relating to the rapid increase in the rate of pressure increase within the left ventricle is determined where the complex impedance and the amplitude waveform meet and deviate.

13. The method of claim 1, wherein measuring the duration of electrical activation in the heart comprises measuring biopotentials representing electrical activation of the heart.

14. The method of claim 13, wherein measuring biopotentials representing electrical activation of the heart further comprises:
measuring surface biopotentials of the patient to produce an electrocardiogram (ECG);
determining the reference time from a point of onset, offset or the full duration of a QRS signal measured from the ECG; and
determining the duration of the QRS complex.

15. The method of claim 1, wherein determining the duration of electrical activation is longer than the first time delay comprises comparing the first time delay with the duration of electrical activation of the heart; and determining the first time delay is longer than a set fraction of electrical activation of the heart.

16. The method of claim 1, wherein the rapid increase of the rate of pressure change relates to the final peak in the second order derivative of the pressure within the left ventricle prior to opening of the aortic valve and/or maximum pressure.

17. The method of claim 1, wherein the first reference time and the second reference time relate to different marker points, wherein the step of comparing the first time delay and the second time delay further comprises:
compensating for a time delay between the first reference time and the second reference time.

18. The method of claim 1, wherein the treatment pacing comprises a number of electrodes and a placement of the electrodes based on the second onset of synergy.

19. The method of claim 18, wherein the number of electrodes and the placement of the electrodes is determined by:
generating a 3D mesh of at least part of the heart from a 3D model of at least part of the heart of the patient, or using a generic 3D model of the heart to obtain a 3D mesh of at least a part of the heart, the 3D mesh of at least a part of the heart comprising a plurality of nodes;
aligning the 3D mesh of at least part of a heart to images of the heart of the patient;
placing additional nodes onto the 3D mesh corresponding to a location of at least two electrodes on the patient;
calculating a propagation velocity of the electrical activation between the nodes of the 3D mesh corresponding to the location of the at least two electrodes;
extrapolating the propagation velocity to all of the nodes of the 3D mesh;
calculating a degree of parallel activation of the myocardium for each node of the 3D mesh; and
determining the optimal electrode number and position on the heart of the patient based on the node(s) of the 3D mesh with a calculated degree of parallel activation of the myocardium above a predetermined threshold.

20. The method of claim 19, wherein determining the degree of parallel activation of a heart undergoing pacing, via a method comprising:
calculating a vectorcadiogram, VCG, or electrocardiogram, ECG, waveforms from right ventricular pacing, RVp, and left ventricular pacing, LVp;
generating a synthetic biventricular pacing, BIVP, waveform pacing by summing the VCG of the RVp and the LVp, or by summing the ECG of the RVp and the LVp;
calculating a corresponding ECG or VCG waveform from real BIVP;
comparing the synthetic BIVP waveform and the real BIVP waveform; and
calculating time to fusion by determining the point in time in which the activation from RVp and LVp meets and the synthetic and the real BIVP curves start to deviate,
wherein a delay in time to fusion indicates that a larger amount of tissue is activated before wave fronts for electrical activation meet, thereby indicating a higher degree of parallel activation.

21. The method of claim 1, wherein an AV-delay of the pacing is calculated so that AP-VP is shorter than the shortest of AP-RVs and AP-QRS.

22. The method of claim 21, wherein the AV-delay of the pacing is 0.7*(AP*RVs) or 0.8*(AP-QRS).

* * * * *